US010888550B2

United States Patent
Lu et al.

(10) Patent No.: US 10,888,550 B2
(45) Date of Patent: Jan. 12, 2021

(54) PYRAZOLE DERIVATIVES AS MALT1 INHIBITORS

(71) Applicant: Janssen Pharmaceutica NV, Beerse (BE)

(72) Inventors: Tianbao Lu, Churchville, PA (US); Peter J. Connolly, New Providence, NJ (US); Maxwell David Cummings, Ambler, PA (US); Gaston Stanislas Marcella Diels, Turnhout (BE); Jan Willem Thuring, Antwerp (BE); Ulrike Philippar, Antwerp (BE); James Patrick Edwards, Ambler, PA (US); Didier Jean-Claude Berthelot, La Neuville Chang d'Oisel (FR); Tongfei Wu, Hever (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/440,356

(22) Filed: Jun. 13, 2019

(65) Prior Publication Data

US 2019/0381012 A1    Dec. 19, 2019

Related U.S. Application Data

(60) Provisional application No. 62/686,451, filed on Jun. 18, 2018.

(51) Int. Cl.
| | |
|---|---|
| *A61K 31/437* | (2006.01) |
| *A61P 35/00* | (2006.01) |
| *A61K 31/519* | (2006.01) |
| *C07D 471/04* | (2006.01) |
| *C07K 16/28* | (2006.01) |

(52) U.S. Cl.
CPC .......... *A61K 31/437* (2013.01); *A61K 31/519* (2013.01); *A61P 35/00* (2018.01); *C07D 471/04* (2013.01); *C07K 16/2887* (2013.01); *C07K 16/2896* (2013.01)

(58) Field of Classification Search
CPC .................................................. A61K 31/437
USPC ........................................................ 514/300
See application file for complete search history.

(56) References Cited

U.S. PATENT DOCUMENTS

| | | |
|---|---|---|
| 6,339,099 B1 | 1/2002 | Lam et al. |
| 7,151,113 B2 | 12/2006 | Dyckman et al. |
| 7,223,782 B2 | 5/2007 | Atkinson et al. |
| 7,253,170 B2 | 8/2007 | Dyckman et al. |
| 7,390,810 B2 | 6/2008 | Dyckman et al. |
| 7,396,935 B2 | 7/2008 | Dyckman et al. |
| 7,414,056 B2 | 8/2008 | Dyckman et al. |
| 7,592,338 B2 | 9/2009 | Dyckman et al. |
| 7,605,273 B2 | 10/2009 | Dyckman et al. |
| 9,375,008 B2 | 6/2016 | Gross et al. |

FOREIGN PATENT DOCUMENTS

| | | |
|---|---|---|
| WO | WO 2001/002385 A1 | 1/2001 |
| WO | WO 2003/037274 A2 | 5/2003 |
| WO | WO 2003/037274 A3 | 5/2003 |
| WO | WO 2004/098518 A2 | 11/2004 |
| WO | WO 2004/098518 A3 | 11/2004 |
| WO | WO 2008/008286 A2 | 1/2008 |
| WO | WO 2008/008286 A3 | 1/2008 |
| WO | WO 2015/181747 A1 | 12/2015 |
| WO | WO 2018/119036 A1 | 6/2018 |

OTHER PUBLICATIONS

Bornancin, F., et al., "Deficiency of MALT1 Paracaspase Activity Results in Unbalanced Regulatory and Effector T and B Cell Responses Leading to Multiorgan Inflammation", J. Immunology, (2015), vol. 194, No. 8, pp. 3723-3734.
Demeyer, A., et al., "Targeting MALT1 Proteolytic Activity in Immunity, Inflammation and Disease: Good or Bad?", Trends Mol Med, (2016), vol. 22, No. 2, pp. 135-150.
Fontan, L., et al., "MALT1 Small Molecule Inhibitors Specifically Suppress ABC-DLBCL In Vitro and In Vivo", Cancer Cell, (2012), vol. 22, No. 6, pp. 812-824.
Gewies, A., et al., "Uncoupling Malt1 Threshold Function from Paracaspase Activity Results in Destructive Autoimmune Inflammation", Cell Reports, (2014), vol. 9, pp. 1292-1305.
Jabara, H.H., et al., "A homozygous mucosa-associated lymphoid tissue 1 (MALT1) mutation in a family with combined immunodeficiency", J. Allergy Clin. Immunol., (2013), vol. 132, pp. 151-158.
Jaworski, M., et al., "Malt1 protease inactivation efficiently dampens immune responses but causes spontaneous autoimmunity", The EMBO Journal, (2014), vol. 33, No. 23, pp. 2765-2781.
Jaworski, M., et al., "The paracaspase MALT1: biological function and potential for therapeutic inhibition", Cell. Mol. Life Sci., (2016), vol. 73, pp. 459-473.
Lim, K., et al., "Pathogentic importance and therapeutica implications of NF-Kβ in lymphoid malignancies", Immunological Reviews, (2012), vol. 246, pp. 359-378.

(Continued)

*Primary Examiner* — Taofiq A Solola

(57) ABSTRACT

Disclosed are compounds, compositions and methods for treating of diseases, syndromes, conditions, and disorders that are affected by the modulation of MALT1. Such compounds are represented by Formula (I) as follows:

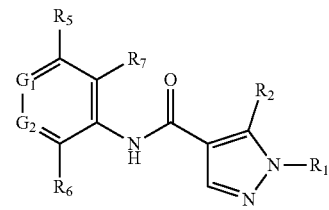

Formula (I)

wherein $R_1$, $R_2$, $R_3$, $R_4$, $R_5$, $R_6$, $R_7$, $G_1$ and $G_2$, are defined herein.

10 Claims, No Drawings

(56) References Cited

OTHER PUBLICATIONS

McGuire, C., et al., "Pharmacological inhibition of MALT1 protease activity protects mice in a mouse model of multiple sclerosis", Journal of Neuroinflammation, (2014), vol. 11, No. 124, pp. 1-12.
McKinnon et al., "Combined immunodeficiency associated with homozygous MALT1 mutations", J. Allergy Clin. Immunol. (2014), vol. 133, No. 5, pp. 1458-1462.e7.
Nagel, D., et al., "Pharmacologic Inhibition of MALT1 Protease by Phenothiazines as a Therapeutic Approach for the Treatment of Aggressive ABC-DLBCL", Cancer Cell, (2012), vol. 22, pp. 825-837.
Punwani, D., et al., "Combined Immunodeficiency Due to MALT1 Mutations, Treated by Hematopoietic Cell Transplantation", J Clin Immunol, (2015), vol. 35, pp. 135-146.
Rosebeck, S., et al., "Cleavage of NIK by the API2-MALT1 Fusion Oncoprotein Leads to Noncanonical NF-kB Activation", Science, (2011), vol. 331, pp. 468-472.
Rosebeck, S., et al., "API2-MALT1 oncoprotein promotes lymphomagenesis via unique program of substrate ubiquitination and proteolysis", World J Biol Chem, (2016), vol. 7, No. 1, pp. 128-137.
Yu, J.W., et al., "MALT1 Protease Activity Is Required for Innate and Adaptive Immune Responses", PLOS One, (2015), pp. 1-20.
Bundgaard, H., "Design of Prodrugs", (1985), Table of Contents.
McOmie, J., "Protective Groups in Organic Chemistry", (1973), Title Page and Table of Contents.
T.W. Greene & P.G.M. Wutz (eds.), Protective Groups in Organic Synthesis, $2^{nd}$ edition, John Wiley & Sons, Inc., (1991), Table of Contents.
T.W. Greene & P.G.M. Wutz (eds.), Protective Groups in Organic Synthesis, $3^{rd}$ edition, John Wiley & Sons, Inc., (1999), Table of Contents.

PYRAZOLE DERIVATIVES AS MALT1 INHIBITORS

CROSS-REFERENCE TO RELATED APPLICATIONS

This application claims priority from U.S. Application No. 62/686,451, filed on Jun. 18, 2018, which is incorporated herein by reference.

FIELD OF THE INVENTION

The present invention relates to novel compounds that are MALT1 (mucosa-associated lymphoid tissue lymphoma translocation protein 1) inhibitors. These compounds may be useful for the treatment of a disease, syndrome, condition, or disorder, particularly a MALT1-related disease, syndrome, condition, or disorder, including but not limited to, cancer and immunological diseases. The invention also relates to pharmaceutical compositions comprising one or more of such compounds, to processes to prepare such compounds and compositions, and to the use of such compounds or pharmaceutical compositions for the treatment of cancer and autoimmunological diseases, syndromes, disorders, or conditions associated with MALT1 inhibitors.

BACKGROUND OF THE INVENTION

MALT1 (mucosa-associated lymphoid tissue lymphoma translocation 1) is a key mediator of the classical $NF_KB$ signaling pathway. MALT1 is the only human paracaspase and transduces signals from the B cell receptor (BCR) and T cell receptor (TCR). MALT1 is the active subunit of the CBM complex which is formed upon receptor activation. The CBM complex consists of multiple subunits of three proteins: CARD11 (caspase recruitment domain family member 11), BCL10 (B-cell CLL/Lymphoma 10) and MALT1. MALT1 affects $NF_KB$ signaling by two mechanisms: firstly, MALT1 functions as a scaffolding protein and recruits $NF_KB$ signaling proteins such as TRAF6, TAB-TAK1 or NEMO-IKKα/β; and secondly, MALT1, as a cysteine protease, cleaves and thereby deactivates negative regulators of $NF_KB$ signaling, such as RelB, A20 or CYLD. The ultimate endpoint of MALT1 activity is the nuclear translocation of the $NF_KB$ transcription factor complex and activation of $NF_KB$ signaling (Jaworski et al., Cell Mol Life Science 2016. 73, 459-473).

Constitutive activation of $NF_KB$ signaling is the hallmark of ABC-DLBCL (Diffuse Large B cell Lymphoma of the Activated B Cell-like subtype), the more aggressive form of DLBCL. DLBCL is the most common form of non-Hodgkin's lymphoma (NHL), accounting for approximately 25% of lymphoma cases while ABC-DLBCL comprises approximately 40% of DLBCL. $NF_KB$ pathway activation is driven by mutations of signaling components, such as CD79A/B, CARD11, MYD88 or A20, in ABC-DLBCL patients (Staudt, Cold Spring Harb Perspect Biol 2010, 2; Lim et al, Immunol Rev 2012, 246, 359-378).

The use of BTK inhibitors, for example Ibrutinib, provides clinical proof-of-concept that inhibiting $NF_KB$ signaling in ABC-DLBCL is efficacious. MALT1 is downstream of BTK in the $NF_KB$ signaling pathway and a MALT1 inhibitor could target ABC-DLBCL patients not responding to Ibrutinib, mainly patients with CARD11 mutations, as well as treat patients that acquired resistance to Ibrutinib.

Small molecule tool compound inhibitors of MALT1 protease have demonstrated efficacy in preclinical models of ABC-DLBCL (Fontan et al., Cancer Cell 2012, 22, 812-824; Nagel et al., Cancer Cell 2012, 22, 825-837). Interestingly, covalent catalytic site and allosteric inhibitors of MALT1 protease function have been described, suggesting that inhibitors of this protease may be useful as pharmaceutical agents (Demeyer et al., Trends Mol Med 2016, 22, 135-150).

The chromosomal translocation creating the API2-MALT1 fusion oncoprotein is the most common mutation identified in MALT (mucosa-associated lymphoid tissue) lymphoma. API2-MALT1 is a potent activator of the $NF_KB$ pathway (Rosebeck et al., World J Biol Chem 2016, 7, 128-137). API2-MALT1 mimics ligand-bound TNF receptor, promotes TRAF2-dependent ubiquitination of RIP1 which acts as a scaffold for activating canonical $NF_KB$ signaling. Furthermore, API2-MALT1 has been shown to cleave and generate a stable, constitutively active fragment of $NF_KB$-inducing kinase (NIK) thereby activating the non-canonical $NF_KB$ pathway (Rosebeck et al., Science, 2011, 331, 468-472).

In addition to lymphomas, MALT1 has been shown to play a critical role in innate and adaptive immunity (Jaworski M, et al., Cell Mol Life Sci. 2016). MALT1 protease inhibitor can attenuate disease onset and progression of mouse experimental allergic encephalomyelitis, a mouse model of multiple sclerosis (Mc Guire et al., J. Neuroinflammation 2014, 11, 124). Mice expressing catalytically inactive MALT1 mutant showed loss of marginal zone B cells and B1 B cells and general immune deficiency characterized as decreased T and B cell activation and proliferation. However, those mice also developed spontaneous multi-organ autoimmune inflammation at the age of 9 to 10 weeks. It is still poorly understood why MALT1 protease dead knock-in mice show a break of tolerance while conventional MALT1 KO mice do not. One hypothesis suggests the unbalanced immune homeostasis in MALT1 protease dead knock-in mice may be caused by incomplete deficiency in T and B cell but severe deficiency of immunoregulatory cells (Jaworski et al., EMBO J. 2014; Gewies et al., Cell Reports 2014; Bornancin et al., J. Immunology 2015; Yu et al., PLOS One 2015). Similarly, MALT deficiency in humans has been associated with combined immunodeficiency disorder (McKinnon et al., J. Allergy Clin. Immunol. 2014, 133, 1458-1462; Jabara et al., J. Allergy Clin. Immunol. 2013, 132, 151-158; Punwani et al., J. Clin. Immunol. 2015, 35, 135-146). Given the difference between genetic mutation and pharmacological inhibition, a phenotype of MALT1 protease dead knock-in mice might not resemble that of patients treated with MALT1 protease inhibitors. A reduction of immunosuppressive T cells by MALT1 protease inhibition may be beneficial to cancer patients by potentially increasing antitumor immunity.

Thus, MALT1 inhibitors of the present invention may provide a therapeutic benefit to patients suffering from cancer and/or immunological diseases.

SUMMARY OF THE INVENTION

The present invention is directed to compounds of Formula (I)

Formula (I)

wherein

R₁ is a heteroaryl independently selected from the group consisting of pyrazolo[1,5-a]pyridinyl and imidazo[1,2-a]pyridinyl; wherein R₁ is optionally independently substituted with one or two substituents selected from methyl, ethyl, fluoro, chloro, cyano, or aminocarbonyl;

R₂ is independently selected from the group consisting of $C_{1-4}$alkyl, 1-methoxy-ethyl, difluoromethyl, fluoro, chloro, bromo, cyano, methylsulfonyl and trifluoromethyl;

G₁ is N or C(R₄);

G₂ is N or C(R₃); such that only one of G₁ and G₂ are N in any instance;

R₃ is independently selected from the group consisting of trifluoromethyl, cyano, $C_{1-4}$alkyl, fluoro, chloro, bromo, methylcarbonyl, methylthio, methylsulfinyl, and methanesulfonyl;

R₄ is independently selected from the group consisting of triazolyl, 1-(methoxy)ethyl, oxazolyl, isoxazolyl, pyrazolyl, pyrrolyl, thiazolyl, tetrazolyl, oxadiazolyl, and imidazolyl; wherein R₄ other than 1-methoxyethyl is optionally independently substituted with one or two substituents selected from oxo, $C_{1-4}$alkyl, carboxy, methoxycarbonyl, aminocarbonyl, hydroxymethyl, aminomethyl, (dimethylamino)methyl, amino, methoxymethyl, trifluoromethyl, amino($C_{2-4}$alkyl)amino, or cyano; or R₄ is independently selected from the group consisting of tetrahydrofuran-2-yl, CH₃SO₂—, (CH₃)₂S(=O)(=N)—, and CH₃(NH=)(O=)S—;

R₅ is independently selected from the group consisting of hydrogen, methyl, ethyl, fluoro, chloro, bromo, trifluoromethyl, methylthio, methylsulfonyl, methoxy, and cyano;

R₆ is hydrogen, $C_{1-4}$alkyl, fluoro, 2-methoxy-ethoxy, chloro, cyano, or trifluoromethyl;

R₇ is hydrogen, methyl, ethyl, or fluoro;

or an enantiomer, diastereomer, or pharmaceutically acceptable salt form thereof.

The present invention also provides a pharmaceutical composition comprising, consisting of and/or consisting essentially of a pharmaceutically acceptable carrier, a pharmaceutically acceptable excipient, and/or a pharmaceutically acceptable diluent and a compound of Formula (I), or a pharmaceutically acceptable salt form thereof.

Also provided are processes for making a pharmaceutical composition comprising, consisting of, and/or consisting essentially of admixing a compound of Formula (I), and a pharmaceutically acceptable carrier, a pharmaceutically acceptable excipient, and/or a pharmaceutically acceptable diluent.

The present invention further provides methods for treating or ameliorating a disease, syndrome, condition, or disorder in a subject, including a mammal and/or human in which the disease, syndrome, or condition is affected by the inhibition of MALT1, including but not limited to, cancer and/or immunological diseases, using a compound of Formula (I).

The present invention also is directed to the use of any of the compounds described herein in the preparation of a medicament wherein the medicament is prepared for treating a disease, syndrome, condition, or disorder that is affected by the inhibition of MALT1, such as cancer and/or immunological diseases.

The present invention is also directed to the preparation of substituted pyrazole derivatives that act as an inhibitor of MALT1.

Exemplifying the invention are methods of treating a disease, syndrome, condition, or disorder mediated by MALT1, selected from the group consisting of lymphomas, leukemias, carcinomas, and sarcomas, e.g. non-Hodgkin's lymphoma (NHL), B-cell NHL, diffuse large B-cell lymphoma (DLBCL), mantle cell lymphoma (MCL), follicular lymphoma (FL), mucosa-associated lymphoid tissue (MALT) lymphoma, marginal zone lymphoma, T-cell lymphoma, Hodgkin's lymphoma, Burkitt's lymphoma, multiple myeloma, chonic lymphocytic leukemia (CLL), small lymphocytic lymphoma (SLL), Waldenström macroglobulinemia, lymphoblastic T cell leukemia, chonic myelogenous leukemia (CIVIL), hairy-cell leukemia, acute lymphoblastic T cell leukemia, plasmacytoma, immunoblastic large cell leukemia, megakaryoblastic leukemia, acute megakaryocytic leukemia, promyelocytic leukemia, erytholeukemia, brain (gliomas), glioblastomas, breast cancer, colorectal/colon cancer, prostate cancer, lung cancer including non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head and neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, and GIST (gastrointestinal stromal tumor), comprising, consisting of, and/or consisting essentially of, administering to a subject in need thereof a therapeutically effective amount of any of the compounds or pharmaceutical compositions described in the present invention.

In another embodiment, the present invention is directed to a compound of Formula (I) for use in the treatment of a disease, syndrome, condition, or disorder affected by the inhibition of MALT1, selected from the group consisting of lymphomas, leukemias, carcinomas, and sarcomas, e.g. non-Hodgkin's lymphoma (NHL), B-cell NHL, diffuse large B-cell lymphoma (DLBCL), mantle cell lymphoma (MCL), follicular lymphoma (FL), mucosa-associated lymphoid tissue (MALT) lymphoma, marginal zone lymphoma, T-cell lymphoma, Hodgkin's lymphoma, Burkitt's lymphoma, multiple myeloma, chonic lymphocytic leukemia (CLL), small lymphocytic lymphoma (SLL), Waldenström macroglobulinemia, lymphoblastic T cell leukemia, chonic myelogenous leukemia (CIVIL), hairy-cell leukemia, acute lymphoblastic T cell leukemia, plasmacytoma, immunoblastic large cell leukemia, megakaryoblastic leukemia, acute megakaryocytic leukemia, promyelocytic leukemia, erytholeukemia, brain (gliomas), glioblastomas, breast cancer, colorectal/colon cancer, prostate cancer, lung cancer including non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head and neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, and GIST (gastrointestinal stromal tumor).

In another embodiment, the present invention is directed to a composition comprising a compound of Formula (I) for the treatment of a disease, syndrome, condition, or disorder affected by inhibition of MALT1, selected from the group consisting of lymphomas, leukemias, carcinomas, and sarcomas, e.g. non-Hodgkin's lymphoma (NHL), B-cell NHL, diffuse large B-cell lymphoma (DLBCL), mantle cell lymphoma (MCL), follicular lymphoma (FL), mucosa-associated lymphoid tissue (MALT) lymphoma, marginal zone lymphoma, T-cell lymphoma, Hodgkin's lymphoma, Burkitt's lymphoma, multiple myeloma, chonic lymphocytic leukemia (CLL), small lymphocytic lymphoma (SLL), Waldenström macroglobulinemia, lymphoblastic T cell leukemia, chonic myelogenous leukemia (CIVIL), hairy-cell leukemia, acute lymphoblastic T cell leukemia, plasmacytoma, immunoblastic large cell leukemia, megakaryoblastic leukemia, acute megakaryocytic leukemia, promyelocytic leukemia, erytholeukemia, brain (gliomas), glioblastomas, breast cancer, colorectal/colon cancer, prostate cancer, lung cancer including non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head and neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, and GIST (gastrointestinal stromal tumor).

In another embodiment, the present invention is directed to a composition comprising a compound of Formula (I) for the treatment of a disease, syndrome, condition, or disorder affected by inhibition of MALT1, selected from the group consisting of diffuse large B-cell lymphoma (DLBCL), mantle cell lymphoma (MCL), follicular lymphoma (FL), and mucosa-associated lymphoid tissue (MALT) lymphoma.

An embodiment of the present invention is directed to a composition comprising a compound of Formula (I) for the treatment of immunological diseases that are affected by the inhibition of MALT1, including but not limited to, autoimmune and inflammatory disorders, e.g. arthritis, inflammatory bowel disease, gastritis, ankylosing spondylitis, ulcerative colitis, pancreatits, Crohn's disease, celiac disease, multiple sclerosis, systemic lupus erythematosus, lupus nephritis, rheumatic fever, gout, organ or transplact rejection, chronic allograft rejection, acute or chronic graft-versus-host disease, dermatitis including atopic, dermatomyositis, psoriasis, Behcet's diseases, uveitis, myasthenia gravis, Grave's disease, Hashimoto thyroiditis, Sjoergen's syndrome, blistering disorders, antibody-mediated vasculitis syndromes, immune-complex vasculitides, allergic disorders, asthma, bronchitis, chronic obstructive pulmonary disease (COPD), cystic fibrosis, pneumonia, pulmonary diseases including oedema, embolism, fibrosis, sarcoidosis, hypertension and emphysema, silicosis, respiratory failure, acute respiratory distress syndrome, BENTA disease, berylliosis, and polymyositis.

In another embodiment, the present invention is directed to a composition comprising a compound of Formula (I) for the treatment of a disease, syndrome, condition, or disorder affected by inhibition of MALT1, selected from the group consisting of rheumatoid arthritis (RA), psoritic arthritis (PsA), psorisis (Pso), ulcerative colitis (UC), Crohn's disease, systemic lupus erythematosus (SLE), asthma, and chronic obstructive pulmonary disease (COPD).

Another embodiment of the present invention is directed to a pharmaceutical composition comprising a compound of Formula (I).

DETAILED DESCRIPTION OF THE INVENTION

Embodiments of the present invention include a compound of Formula (I)

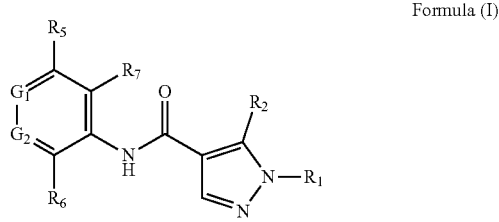

Formula (I)

wherein

AA) $R_1$ is a heteroaryl independently selected from the group consisting of pyrazolo[1,5-a]pyridin-4-yl and imidazo[1,2-a]pyridin-5-yl; wherein $R_1$ is optionally independently substituted with a substituent selected from the group consisting of chloro, aminocarbonyl, and cyano;

BB) $R_1$ is a heteroaryl independently selected from the group consisting of (7-aminocarbonyl)pyrazolo[1,5-a]pyridin-4-yl, (7-chloro)pyrazolo[1,5-a]pyridin-4-yl, (7-cyano)pyrazolo[1,5-a]pyridin-4-yl, (8-aminocarbonyl)imidazo[1,2-a]pyridin-5-yl, (8-chloro)imidazo[1,2-a]pyridin-5-yl, (8-cyano)imidazo[1,2-a]pyridin-5-yl, (8-fluoro)imidazo[1,2-a]pyridin-5-yl;

CC) $R_2$ is trifluoromethyl or methylsulfonyl;

DD) $R_3$ is independently selected from the group consisting of trifluoromethyl, cyano, and chloro;

EE) $R_3$ is trifluoromethyl;

FF) $G_2$ is N;

GG) $R_4$ is independently selected from the group consisting of 2H-1,2,3-triazol-2-yl, oxazol-2-yl, 4-methyloxazol-2-yl, 5-methyloxazolyl-2-yl, 1H-pyrazol-1-yl and tetrahydrofuran-2-yl;

HH) $R_4$ is independently selected from the group consisting 1(*R)-methoxyethyl, 1(*S)-methoxyethyl, (*R)-tetrahydrofuran-2-yl, and (*S)-tetrahydrofuran-2-yl;

II) $R_5$ is hydrogen, fluoro, chloro, bromo or trifluoromethyl;

and any combination of embodiments AA) through II) above, provided it is understood that combinations in which different embodiments of the same substituent would be combined are excluded; such that only one of $G_1$ and $G_2$ are N in any instance;

or an enantiomer, diastereomer, or pharmaceutically acceptable salt form thereof.

Embodiments of the present invention include a compound of Formula (I)

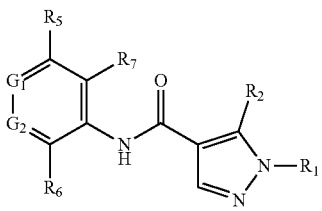

Formula (I)

wherein
R₁ is a heteroaryl independently selected from the group consisting of pyrazolo[1,5-a]pyridinyl and imidazo[1,2-a]pyridinyl; wherein R₁ is optionally independently substituted with one or two substituents selected from methyl, ethyl, fluoro, chloro, cyano, or aminocarbonyl;
R₂ is trifluoromethyl or methyl sulfonyl;
G₁ is N or C(R₄);
G₂ is N or C(R₃); such that only one of G₁ and G₂ are N in any instance;
R₃ is trifluoromethyl;
R₄ is independently selected from the group consisting of triazolyl, 1-(methoxy)ethyl, oxazol-2-yl, 4-methyloxazol-2-yl, 5-methyloxazolyl-2-yl, 1H-pyrazol-1-yl, tetrahydrofuran-2-yl, CH₃SO₂—, (CH₃)₂S(=O)(=N)—, and CH₃(NH=)(O=)S—;
R₅ is independently selected from the group consisting of hydrogen, methyl, ethyl, fluoro, chloro, bromo, trifluoromethyl, methoxy, and cyano;
R₆ is hydrogen, methyl, or trifluoromethyl;
R₇ is hydrogen, methyl, ethyl, or fluoro;
or an enantiomer, diastereomer, or pharmaceutically acceptable salt form thereof.

Another embodiment of the present invention includes a compound of Formula (I)
wherein
R₁ is a heteroaryl independently selected from the group consisting of (7-aminocarbonyl)pyrazolo[1,5-a]pyridin-4-yl, (7-chloro)pyrazolo[1,5-a]pyridin-4-yl, (7-cyano)pyrazolo[1,5-a]pyridin-4-yl, (8-methyl)imidazo[1,2-a]pyridinyl, (8-aminocarbonyl)imidazo[1,2-a]pyridin-5-yl, (8-chloro)imidazo[1,2-a]pyridin-5-yl, (8-cyano)imidazo[1,2-a]pyridin-5-yl, (8-fluoro)imidazo[1,2-a]pyridin-5-yl;
R₂ is trifluoromethyl or methyl sulfonyl;
G₁ is N or C(R₄);
G₂ is N or C(R₃); such that only one of G₁ and G₂ are N in any instance;
R₃ is trifluoromethyl;
R₄ is independently selected from the group consisting of traizol-2-yl, pyrazol-1-yl, oxazol-2-yl, 4-methyloxazol-2-yl, 5-methyloxazol-2-yl, 1(*R)-methoxyethyl, 1(*S)-methoxyethyl, (*R)-tetrahydrofuran-2-yl, (*S)-tetrahydrofuran-2-yl, CH₃SO₂—, (CH₃)₂S(=O)(=N)—, and CH₃(NH=)(O=)S—;
R₅ is independently selected from the group consisting of hydrogen, methyl, fluoro, chloro, trifluoromethyl, and methoxy;
R₆ is hydrogen;
R₇ is hydrogen;
or an enantiomer, diastereomer, or pharmaceutically acceptable salt form thereof Additional embodiments of the present invention include compounds of Formula (I) as herein defined, or an enantiomer, diastereomer, solvate, or a pharmaceutically acceptable salt form thereof, as exemplified in the listing in Table 1, below.

TABLE 1

| Structure | Cpd No. | Cpd Name |
|---|---|---|
| 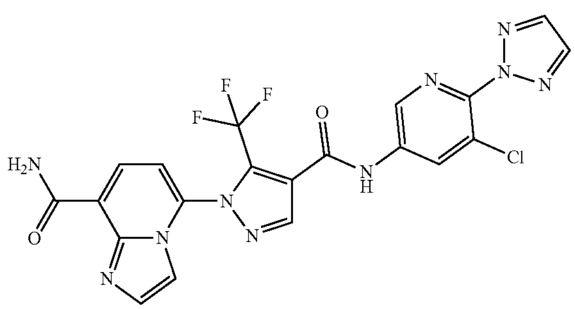 [SMILES: NC(=O)c1ccc(-n2ncc(C(=O)Nc3cnc(-n4nccn4)c(Cl)c3)c2C(F)(F)F)n2ccnc12] | 1 | 5-(4-((5-chloro-6-(2H-1,2,3-triazol-2-yl)pyridin-3-yl)carbamoyl)-5-(trifluoromethyl)-1H-pyrazol-1-yl)imidazo[1,2-a]pyridine-8-carboxamide |
| 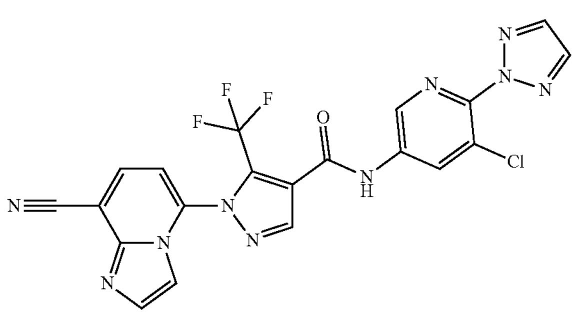 [SMILES: N#Cc1ccc(-n2ncc(C(=O)Nc3cnc(-n4nccn4)c(Cl)c3)c2C(F)(F)F)n2ccnc12] | 2 | N-(5-chloro-6-(2H-1,2,3-triazol-2-yl)pyridin-3-yl)-1-(8-cyanoimidazo[1,2-a]pyridin-5-yl)-5-(trifluoromethyl)-1H-pyrazole-4-carboxamide |

TABLE 1-continued

| Structure | Cpd No. | Cpd Name |
|---|---|---|
| 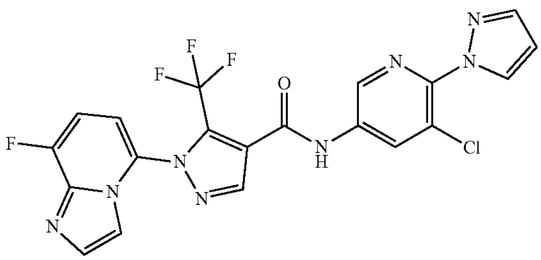 [SMILES: O=C(Nc1cnc(-n2cccn2)c(Cl)c1)c1cnn(-c2ccc(F)c3nccn23)c1C(F)(F)F] | 3 | N-(5-chloro-6-(1H-pyrazol-1-yl)pyridin-3-yl)-1-(8-fluoroimidazo[1,2-a]pyridin-5-yl)-5-(trifluoromethyl)-1H-pyrazole-4-carboxamide |
| 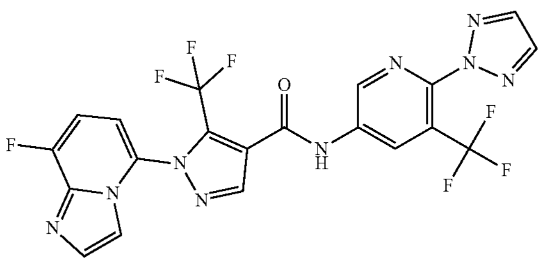 [SMILES: O=C(Nc1cnc(-n2nccn2)c(C(F)(F)F)c1)c1cnn(-c2ccc(F)c3nccn23)c1C(F)(F)F] | 4 | N-(6-(2H-1,2,3-triazol-2-yl)-5-(trifluoromethyl)pyridin-3-yl)-1-(8-fluoroimidazo[1,2-a]pyridin-5-yl)-5-(trifluoromethyl)-1H-pyrazole-4-carboxamide |
| 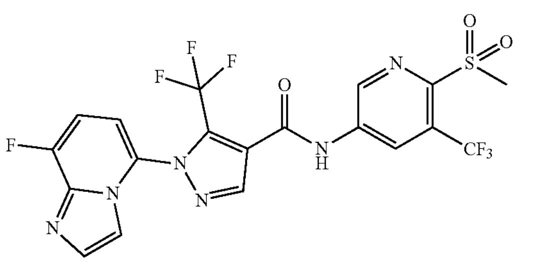 [SMILES: CS(=O)(=O)c1ncc(NC(=O)c2cnn(-c3ccc(F)c4nccn34)c2C(F)(F)F)cc1C(F)(F)F] | 5 | 1-(8-fluoroimidazo[1,2-a]pyridin-5-yl)-N-(6-(methylsulfonyl)-5-(trifluoromethyl)pyridin-3-yl)-5-(trifluoromethyl)-1H-pyrazole-4-carboxamide |
| 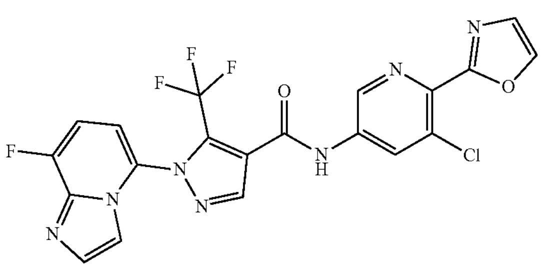 [SMILES: O=C(Nc1cnc(-c2ncco2)c(Cl)c1)c1cnn(-c2ccc(F)c3nccn23)c1C(F)(F)F] | 6 | N-(5-chloro-6-(oxazol-2-yl)pyridin-3-yl)-1-(8-fluoroimidazo[1,2-a]pyridin-5-yl)-5-(trifluoromethyl)-1H-pyrazole-4-carboxamide |
| 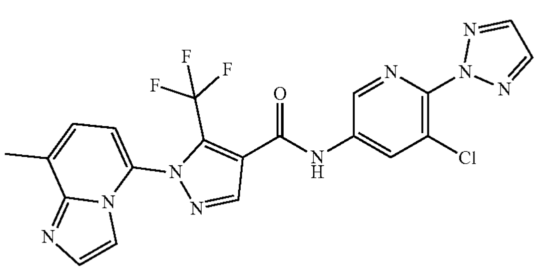 [SMILES: Cc1ccc(-n2ncc(C(=O)Nc3cnc(-n4nccn4)c(Cl)c3)c2C(F)(F)F)n2ccnc12] | 7 | N-(5-chloro-6-(2H-1,2,3-triazol-2-yl)pyridin-3-yl)-1-(8-methylimidazo[1,2-a]pyridin-5-yl)-5-(trifluoromethyl)-1H-pyrazole-4-carboxamide |

TABLE 1-continued

| Structure | Cpd No. | Cpd Name |
|---|---|---|
| 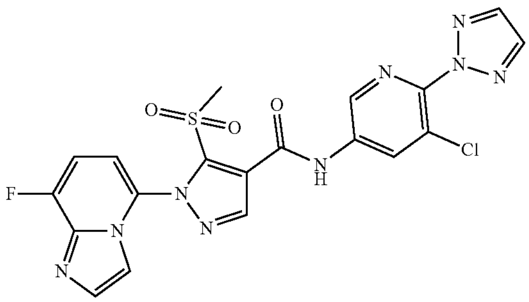 [SMILES: CS(=O)(=O)c1c(C(=O)Nc2cnc(-n3nccn3)c(Cl)c2)cnn1-c1ccc(F)c2nccn12] | 8 | N-(5-chloro-6-(2H-1,2,3-triazol-2-yl)pyridin-3-yl)-1-(8-fluoroimidazo[1,2-a]pyridin-5-yl)-5-(methylsulfonyl)-1H-pyrazole-4-carboxamide |
| 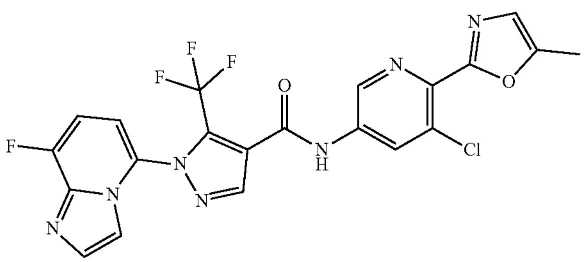 [SMILES: Cc1cnc(-c2ncc(NC(=O)c3cnn(-c4ccc(F)c5nccn45)c3C(F)(F)F)cc2Cl)o1] | 9 | N-(5-chloro-6-(5-methyloxazol-2-yl)pyridin-3-yl)-1-(8-fluoroimidazo[1,2-a]pyridin-5-yl)-5-(trifluoromethyl)-1H-pyrazole-4-carboxamide |
| 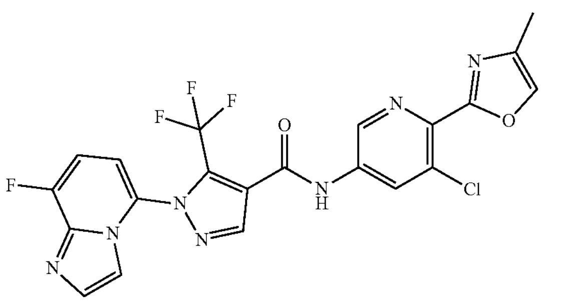 [SMILES: Cc1coc(-c2ncc(NC(=O)c3cnn(-c4ccc(F)c5nccn45)c3C(F)(F)F)cc2Cl)n1] | 10 | N-(5-chloro-6-(4-methyloxazol-2-yl)pyridin-3-yl)-1-(8-fluoroimidazo[1,2-a]pyridin-5-yl)-5-(trifluoromethyl)-1H-pyrazole-4-carboxamide |
| 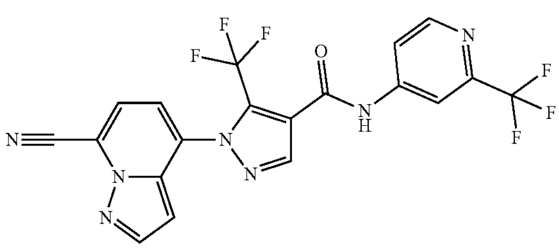 [SMILES: N#Cc1ccc(-n2ncc(C(=O)Nc3ccnc(C(F)(F)F)c3)c2C(F)(F)F)c2ccnn12] | 11 | 1-(7-cyanopyrazolo[1,5-a]pyridin-4-yl)-5-(trifluoromethyl)-N-(2-(trifluoromethyl)pyridin-4-yl)-1H-pyrazole-4-carboxamide |
| 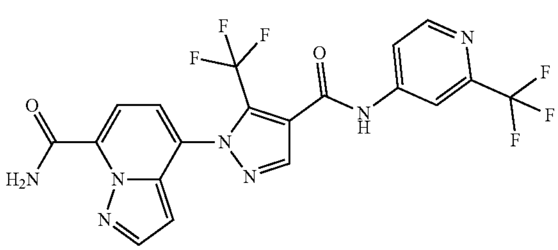 [SMILES: NC(=O)c1ccc(-n2ncc(C(=O)Nc3ccnc(C(F)(F)F)c3)c2C(F)(F)F)c2ccnn12] | 12 | 4-(5-(trifluoromethyl)-4-((2-(trifluoromethyl)pyridin-4-yl)carbamoyl)-1H-pyrazol-1-yl)pyrazolo[1,5-a]pyridine-7-carboxamide |

TABLE 1-continued

| Structure | Cpd No. | Cpd Name |
|---|---|---|
| 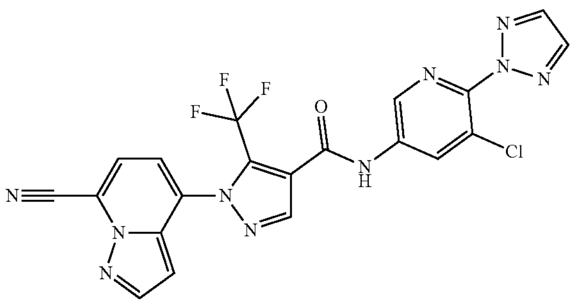 [SMILES: N#Cc1ccc(-n2ncc(C(=O)Nc3cnc(-n4nccn4)c(Cl)c3)c2C(F)(F)F)c2ccnn12] | 13 | N-(5-chloro-6-(2H-1,2,3-triazol-2-yl)pyridin-3-yl)-1-(7-cyanopyrazolo[1,5-a]pyridin-4-yl)-5-(trifluoromethyl)-1H-pyrazole-4-carboxamide |
| 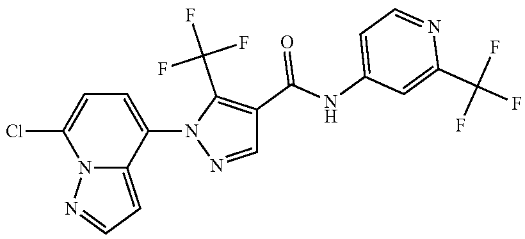 [SMILES: O=C(Nc1ccnc(C(F)(F)F)c1)c1cnn(-c2ccc(Cl)n3nccc23)c1C(F)(F)F] | 14 | 1-(7-chloropyrazolo[1,5-a]pyridin-4-yl)-5-(trifluoromethyl)-N-(2-(trifluoromethyl)pyridin-4-yl)-1H-pyrazole-4-carboxamide |
| 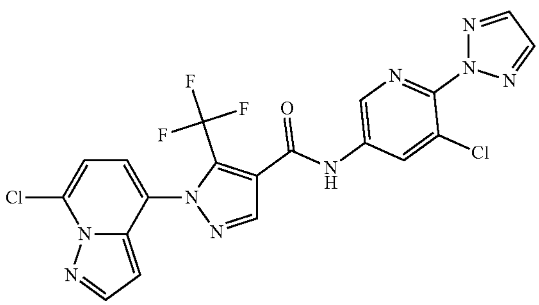 [SMILES: O=C(Nc1cnc(-n2nccn2)c(Cl)c1)c1cnn(-c2ccc(Cl)n3nccc23)c1C(F)(F)F] | 15 | N-(5-chloro-6-(2H-1,2,3-triazol-2-yl)pyridin-3-yl)-1-(7-chloropyrazolo[1,5-a]pyridin-4-yl)-5-(trifluoromethyl)-1H-pyrazole-4-carboxamide |
| 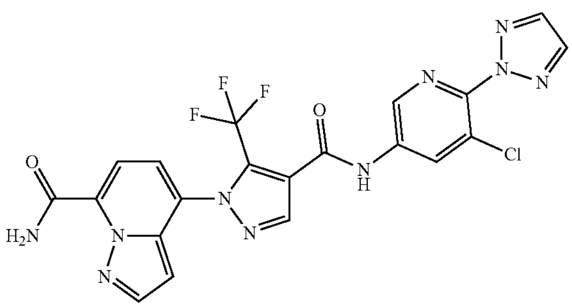 [SMILES: NC(=O)c1ccc(-n2ncc(C(=O)Nc3cnc(-n4nccn4)c(Cl)c3)c2C(F)(F)F)c2ccnn12] | 16 | 4-(4-((5-chloro-6-(2H-1,2,3-triazol-2-yl)pyridin-3-yl)carbamoyl)-5-(trifluoromethyl)-1H-pyrazol-1-yl)pyrazolo[1,5-a]pyridine-7-carboxamide |
| 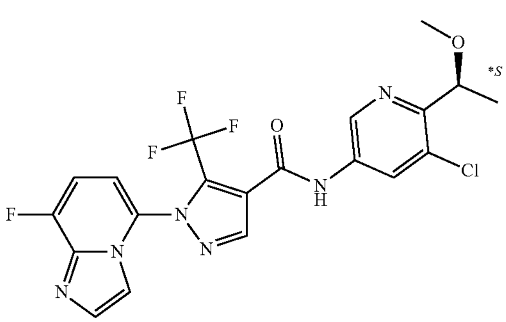 [SMILES: CO[C@@H](C)c1ncc(NC(=O)c2cnn(-c3ccc(F)c4nccn34)c2C(F)(F)F)cc1Cl] | 17 | (*S)-N-(5-chloro-6-(1-methoxyethyl)pyridin-3-yl)-1-(8-fluoroimidazo[1,2-a]pyridin-5-yl)-5-(trifluoromethyl)-1H-pyrazole-4-carboxamide |

TABLE 1-continued

| Structure | Cpd No. | Cpd Name |
|---|---|---|
| 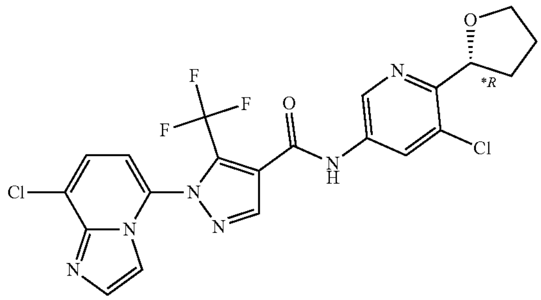 [SMILES: O=C(Nc1cnc([C@H]2CCCO2)c(Cl)c1)c1cnn(-c2ccc(Cl)c3nccn23)c1C(F)(F)F] | 18 | (*R)-N-(5-chloro-6-(tetrahydrofuran-2-yl)pyridin-3-yl)-1-(8-chloroimidazo[1,2-a]pyridin-5-yl)-5-(trifluoromethyl)-1H-pyrazole-4-carboxamide |
| 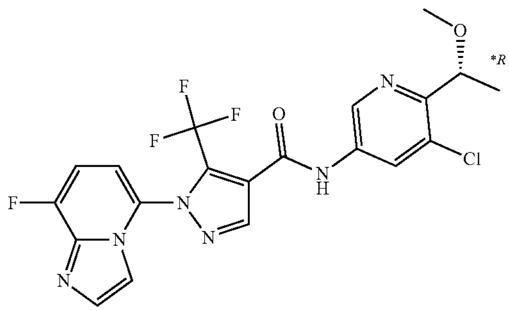 [SMILES: CO[C@H](C)c1ncc(NC(=O)c2cnn(-c3ccc(F)c4nccn34)c2C(F)(F)F)cc1Cl] | 19 | (*R)-N-(5-chloro-6-(1-methoxyethyl)pyridin-3-yl)-1-(8-fluoroimidazo[1,2-a]pyridin-5-yl)-5-(trifluoromethyl)-1H-pyrazole-4-carboxamide |
| 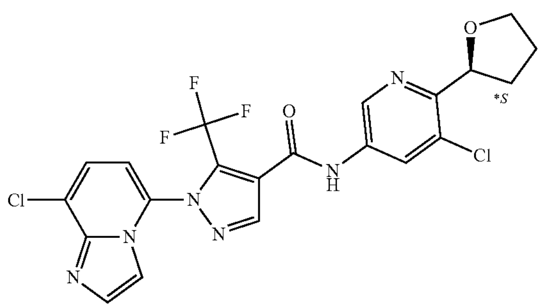 [SMILES: O=C(Nc1cnc([C@@H]2CCCO2)c(Cl)c1)c1cnn(-c2ccc(Cl)c3nccn23)c1C(F)(F)F] | 20 | (*S)-N-(5-chloro-6-(tetrahydrofuran-2-yl)pyridin-3-yl)-1-(8-chloroimidazo[1,2-a]pyridin-5-yl)-5-(trifluoromethyl)-1H-pyrazole-4-carboxamide |
| 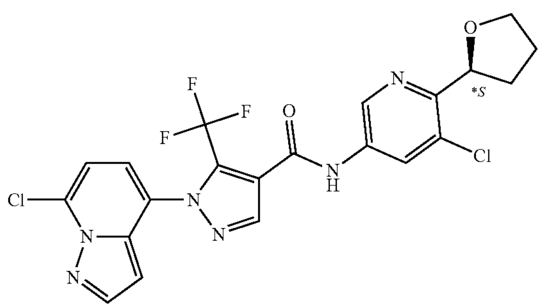 [SMILES: O=C(Nc1cnc([C@@H]2CCCO2)c(Cl)c1)c1cnn(-c2ccc(Cl)n3nccc23)c1C(F)(F)F] | 21 | (*S)-N-(5-chloro-6-(tetrahydrofuran-2-yl)pyridin-3-yl)-1-(7-chloropyrazolo[1,5-a]pyridin-4-yl)-5-(trifluoromethyl)-1H-pyrazole-4-carboxamide |
| 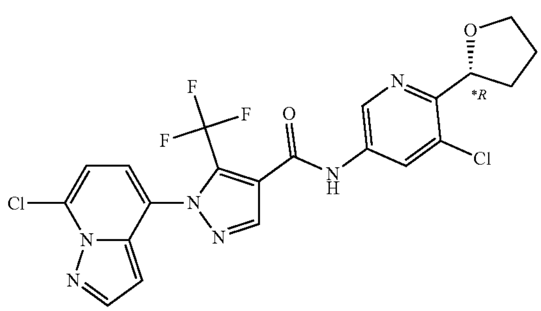 [SMILES: O=C(Nc1cnc([C@H]2CCCO2)c(Cl)c1)c1cnn(-c2ccc(Cl)n3nccc23)c1C(F)(F)F] | 22 | (*R)-N-(5-chloro-6-(tetrahydrofuran-2-yl)pyridin-3-yl)-1-(7-chloropyrazolo[1,5-a]pyridin-4-yl)-5-(trifluoromethyl)-1H-pyrazole-4-carboxamide |

TABLE 1-continued

| Structure | Cpd No. | Cpd Name |
|---|---|---|
| 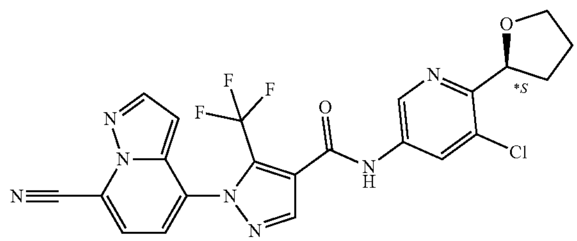 [SMILES: N#Cc1ccc(-n2ncc(C(=O)Nc3cnc([C@@H]4CCCO4)c(Cl)c3)c2C(F)(F)F)c2ccnn12] | 23 | (*S)-N-(5-chloro-6-(tetrahydrofuran-2-yl)pyridin-3-yl)-1-(7-cyanopyrazolo[1,5-a]pyridin-4-yl)-5-(trifluoromethyl)-1H-pyrazole-4-carboxamide |
| 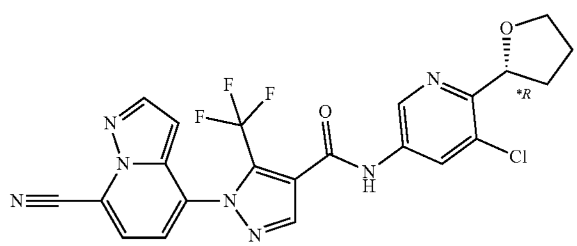 [SMILES: N#Cc1ccc(-n2ncc(C(=O)Nc3cnc([C@H]4CCCO4)c(Cl)c3)c2C(F)(F)F)c2ccnn12] | 24 | (*R)-N-(5-chloro-6-(tetrahydrofuran-2-yl)pyridin-3-yl)-1-(7-cyanopyrazolo[1,5-a]pyridin-4-yl)-5-(trifluoromethyl)-1H-pyrazole-4-carboxamide |
| 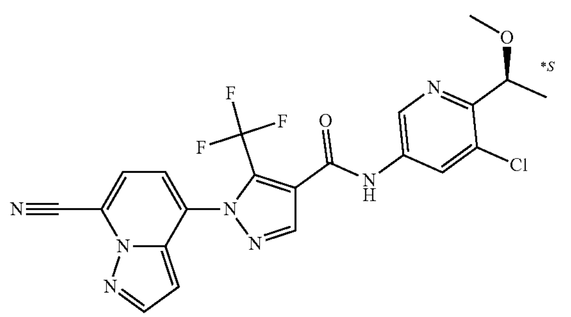 [SMILES: CO[C@@H](C)c1ncc(NC(=O)c2cnn(-c3ccc(C#N)n4nccc34)c2C(F)(F)F)cc1Cl] | 25 | (*S)-N-(5-chloro-6-(1-methoxyethyl)pyridin-3-yl)-1-(7-cyanopyrazolo[1,5-a]pyridin-4-yl)-5-(trifluoromethyl)-1H-pyrazole-4-carboxamide |
| 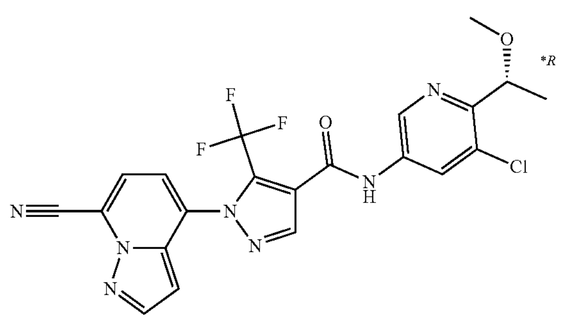 [SMILES: CO[C@H](C)c1ncc(NC(=O)c2cnn(-c3ccc(C#N)n4nccc34)c2C(F)(F)F)cc1Cl] | 26 | (*R)-N-(5-chloro-6-(1-methoxyethyl)pyridin-3-yl)-1-(7-cyanopyrazolo[1,5-a]pyridin-4-yl)-5-(trifluoromethyl)-1H-pyrazole-4-carboxamide |
| 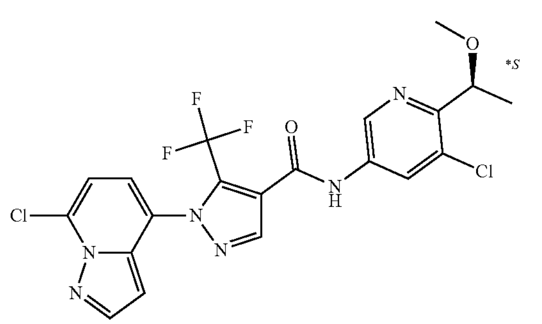 [SMILES: CO[C@@H](C)c1ncc(NC(=O)c2cnn(-c3ccc(Cl)n4nccc34)c2C(F)(F)F)cc1Cl] | 27 | (*S)-N-(5-chloro-6-(1-methoxyethyl)pyridin-3-yl)-1-(7-chloropyrazolo[1,5-a]pyridin-4-yl)-5-(trifluoromethyl)-1H-pyrazole-4-carboxamide |

TABLE 1-continued

| Structure | Cpd No. | Cpd Name |
|---|---|---|
| 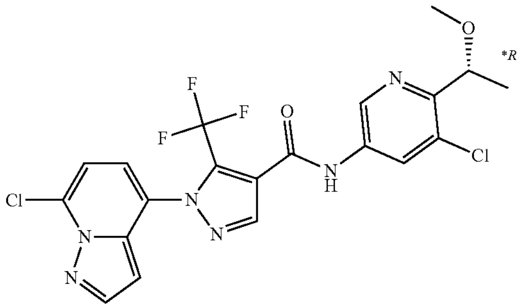 [SMILES: CO[C@H](C)c1ncc(NC(=O)c2cnn(-c3ccc(Cl)n4nccc34)c2C(F)(F)F)cc1Cl] | 28 | (*R)-N-(5-chloro-6-(1-methoxyethyl)pyridin-3-yl)-1-(7-chloropyrazolo[1,5-a]pyridin-4-yl)-5-(trifluoromethyl)-1H-pyrazole-4-carboxamide |
| 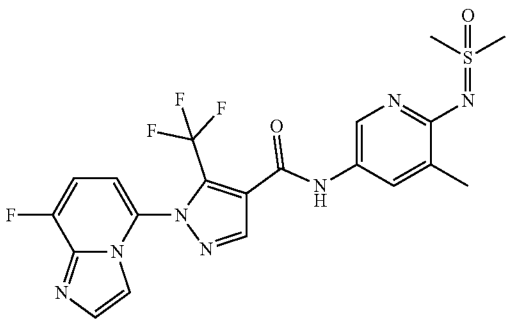 [SMILES: Cc1cc(NC(=O)c2cnn(-c3ccc(F)c4nccn34)c2C(F)(F)F)cnc1N=S(C)(C)=O] | 29 | N-(6-((dimethyl(oxo)-$\lambda^6$-sulfanylidene)amino)-5-methylpyridin-3-yl)-1-(8-fluoroimidazo[1,2-a]pyridin-5-yl)-5-(trifluoromethyl)-1H-pyrazole-4-carboxamide |
| 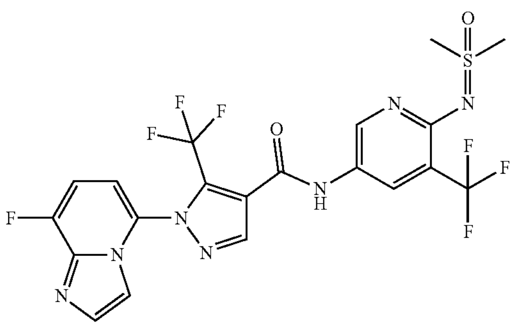 [SMILES: CS(C)(=O)=Nc1ncc(NC(=O)c2cnn(-c3ccc(F)c4nccn34)c2C(F)(F)F)cc1C(F)(F)F] | 30 | N-(6-((dimethyl(oxo)-$\lambda^6$-sulfanylidene)amino)-5-(trifluoromethyl)pyridin-3-yl)-1-(8-fluoroimidazo[1,2-a]pyridin-5-yl)-5-(trifluoromethyl)-1H-pyrazole-4-carboxamide |
| 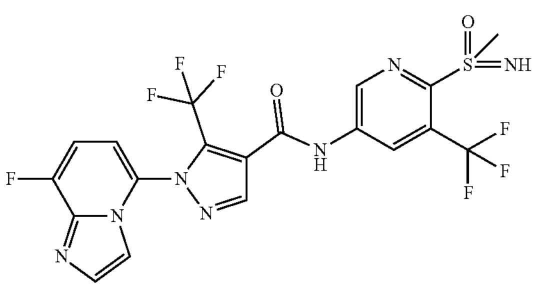 [SMILES: CS(=N)(=O)c1ncc(NC(=O)c2cnn(-c3ccc(F)c4nccn34)c2C(F)(F)F)cc1C(F)(F)F] | 31 | 1-(8-fluoroimidazo[1,2-a]pyridin-5-yl)-N-(6-(S-methylsulfonimidoyl)-5-(trifluoromethyl)pyridin-3-yl)-5-(trifluoromethyl)-1H-pyrazole-4-carboxamide |
| 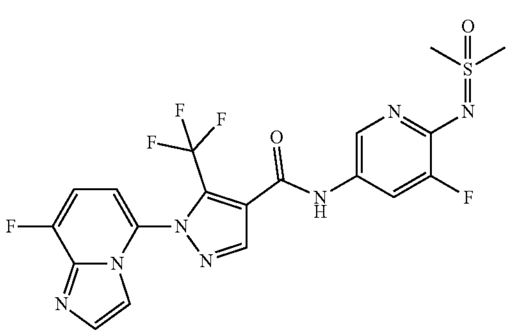 | 32 | N-(6-((dimethyl(oxo)-$\lambda^6$-sulfanylidene)amino)-5-fluoropyridin-3-yl)-1-(8-fluoroimidazo[1,2-a]pyridin-5-yl)-5-(trifluoromethyl)-1H-pyrazole-4-carboxamide |

TABLE 1-continued

| Structure | Cpd No. | Cpd Name |
|---|---|---|
| 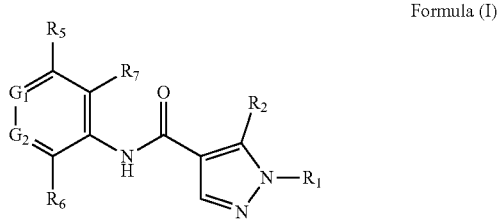 | 33 | N-(5-chloro-6-((dimethyl(oxo)-λ⁶-sulfanylidene)amino)pyridin-3-yl)-1-(8-fluoroimidazo[1,2-a]pyridin-5-yl)-5-(trifluoromethyl)-1H-pyrazole-4-carboxamide |

In a further embodiment, the invention is directed to a compound of Formula (I)

Formula (I)

selected from the group consisting of:

5-(4-((5-chloro-6-(2H-1,2,3-triazol-2-yl)pyridin-3-yl)carbamoyl)-5-(trifluoromethyl)-1H-pyrazol-1-yl)imidazo[1,2-a]pyridine-8-carboxamide;

N-(5-chloro-6-(2H-1,2,3-triazol-2-yl)pyridin-3-yl)-1-(8-cyanoimidazo[1,2-a]pyridin-5-yl)-5-(trifluoromethyl)-1H-pyrazole-4-carboxamide;

N-(5-chloro-6-(1H-pyrazol-1-yl)pyridin-3-yl)-1-(8-fluoroimidazo[1,2-a]pyridin-5-yl)-5-(trifluoromethyl)-1H-pyrazole-4-carboxamide;

N-(6-(2H-1,2,3-triazol-2-yl)-5-(trifluoromethyl)pyridin-3-yl)-1-(8-fluoroimidazo[1,2-c]pyridin-5-yl)-5-(trifluoromethyl)-1H-pyrazole-4-carboxamide;

1-(8-fluoroimidazo[1,2-a]pyridin-5-yl)-N-(6-(methylsulfonyl)-5-(trifluoromethyl)pyridin-3-yl)-5-(trifluoromethyl)-1H-pyrazole-4-carboxamide;

N-(5-chloro-6-(oxazol-2-yl)pyridin-3-yl)-1-(8-fluoroimidazo[1,2-a]pyridin-5-yl)-5-(trifluoromethyl)-1H-pyrazole-4-carboxamide;

N-(5-chloro-6-(2H-1,2,3-triazol-2-yl)pyridin-3-yl)-1-(8-methylimidazo[1,2-a]pyridin-5-yl)-5-(trifluoromethyl)-1H-pyrazole-4-carboxamide;

N-(5-chloro-6-(2H-1,2,3-triazol-2-yl)pyridin-3-yl)-1-(8-fluoroimidazo[1,2-a]pyridin-5-yl)-5-(methylsulfonyl)-1H-pyrazole-4-carboxamide;

N-(5-chloro-6-(5-methyloxazol-2-yl)pyridin-3-yl)-1-(8-fluoroimidazo[1,2-a]pyridin-5-yl)-5-(trifluoromethyl)-1H-pyrazole-4-carboxamide;

N-(5-chloro-6-(4-methyloxazol-2-yl)pyridin-3-yl)-1-(8-fluoroimidazo[1,2-a]pyridin-5-yl)-5-(trifluoromethyl)-1H-pyrazole-4-carboxamide;

1-(7-cyanopyrazolo[1,5-a]pyridin-4-yl)-5-(trifluoromethyl)-N-(2-(trifluoromethyl)pyridin-4-yl)-1H-pyrazole-4-carboxamide;

4-(5-(trifluoromethyl)-4-((2-(trifluoromethyl)pyridin-4-yl)carbamoyl)-1H-pyrazol-1-yl)pyrazolo[1,5-a]pyridine-7-carboxamide;

N-(5-chloro-6-(2H-1,2,3-triazol-2-yl)pyridin-3-yl)-1-(7-cyanopyrazolo[1,5-a]pyridin-4-yl)-5-(trifluoromethyl)-1H-pyrazole-4-carboxamide;

1-(7-chloropyrazolo[1,5-a]pyridin-4-yl)-5-(trifluoromethyl)-N-(2-(trifluoromethyl)pyridin-4-yl)-1H-pyrazole-4-carboxamide;

N-(5-chloro-6-(2H-1,2,3-triazol-2-yl)pyridin-3-yl)-1-(7-chloropyrazolo[1,5-a]pyridin-4-yl)-5-(trifluoromethyl)-1H-pyrazole-4-carboxamide 4-(4-((5-chloro-6-(2H-1,2,3-triazol-2-yl)pyridin-3-yl)carbamoyl)-5-(trifluoromethyl)-1H-pyrazol-1-yl)pyrazolo[1,5-a]pyridine-7-carboxamide;

(*S)—N-(5-chloro-6-(1-methoxyethyl)pyridin-3-yl)-1-(8-fluoroimidazo[1,2-a]pyridin-5-yl)-5-(trifluoromethyl)-1H-pyrazole-4-carboxamide;

(*R)—N-(5-chloro-6-(tetrahydrofuran-2-yl)pyridin-3-yl)-1-(8-chloroimidazo[1,2-a]pyridin-5-yl)-5-(trifluoromethyl)-1H-pyrazole-4-carboxamide;

(*R)—N-(5-chloro-6-(1-methoxyethyl)pyridin-3-yl)-1-(8-fluoroimidazo[1,2-a]pyridin-5-yl)-5-(trifluoromethyl)-1H-pyrazole-4-carboxamide;

(*S)—N-(5-chloro-6-(tetrahydrofuran-2-yl)pyridin-3-yl)-1-(8-chloroimidazo[1,2-a]pyridin-5-yl)-5-(trifluoromethyl)-1H-pyrazole-4-carboxamide;

(*S)—N-(5-chloro-6-(tetrahydrofuran-2-yl)pyridin-3-yl)-1-(7-chloropyrazolo[1,5-a]pyridin-4-yl)-5-(trifluoromethyl)-1H-pyrazole-4-carboxamide;

(*R)—N-(5-chloro-6-(tetrahydrofuran-2-yl)pyridin-3-yl)-1-(7-chloropyrazolo[1,5-a]pyridin-4-yl)-5-(trifluoromethyl)-1H-pyrazole-4-carboxamide;

(*S)—N-(5-chloro-6-(tetrahydrofuran-2-yl)pyridin-3-yl)-1-(7-cyanopyrazolo[1,5-a]pyridin-4-yl)-5-(trifluoromethyl)-1H-pyrazole-4-carboxamide;

(*R)—N-(5-chloro-6-(tetrahydrofuran-2-yl)pyridin-3-yl)-1-(7-cyanopyrazolo[1,5-a]pyridin-4-yl)-5-(trifluoromethyl)-1H-pyrazole-4-carboxamide;

(*S)—N-(5-chloro-6-(1-methoxyethyl)pyridin-3-yl)-1-(7-cyanopyrazolo[1,5-a]pyridin-4-yl)-5-(trifluoromethyl)-1H-pyrazole-4-carboxamide;

(*R)—N-(5-chloro-6-(1-methoxyethyl)pyridin-3-yl)-1-(7-cyanopyrazolo[1,5-a]pyridin-4-yl)-5-(trifluoromethyl)-1H-pyrazole-4-carboxamide;

(*S)—N-(5-chloro-6-(1-methoxyethyl)pyridin-3-yl)-1-(7-chloropyrazolo[1,5-a]pyridin-4-yl)-5-(trifluoromethyl)-1H-pyrazole-4-carboxamide;

(*R)—N-(5-chloro-6-(1-methoxyethyl)pyridin-3-yl)-1-(7-chloropyrazolo[1,5-a]pyridin-4-yl)-5-(trifluoromethyl)-1H-pyrazole-4-carboxamide;

N-(6-((dimethyl(oxo)-$\lambda^6$-sulfanylidene)amino)-5-methylpyridin-3-yl)-1-(8-fluoroimidazo[1,2-a]pyridin-5-yl)-5-(trifluoromethyl)-1H-pyrazole-4-carboxamide;

N-(6-((dimethyl(oxo)-$\lambda^6$-sulfanylidene)amino)-5-(trifluoromethyl)pyridin-3-yl)-1-(8-fluoroimidazo[1,2-a]pyridin-5-yl)-5-(trifluoromethyl)-1H-pyrazole-4-carboxamide;

1-(8-fluoroimidazo[1,2-a]pyridin-5-yl)-N-(6-(S-methylsulfonimidoyl)-5-(trifluoromethyl)pyridin-3-yl)-5-(trifluoromethyl)-1H-pyrazole-4-carboxamide;

N-(6-((dimethyl(oxo)-$\lambda^6$-sulfanylidene)amino)-5-fluoropyridin-3-yl)-1-(8-fluoroimidazo[1,2-a]pyridin-5-yl)-5-(trifluoromethyl)-1H-pyrazole-4-carboxamide; and N-(5-chloro-6-((dimethyl(oxo)-$\lambda^6$-sulfanylidene)amino)pyridin-3-yl)-1-(8-fluoroimidazo[1,2-a]pyridin-5-yl)-5-(trifluoromethyl)-1H-pyrazole-4-carboxamide or a pharmaceutically acceptable salt form thereof.

With reference to substituents, the term "independently" refers to the situation where when more than one substituent is possible, the substituents may be the same or different from each other.

The term "alkyl" whether used alone or as part of a substituent group, refers to straight and branched carbon chains having 1 to 8 carbon atoms. Therefore, designated numbers of carbon atoms (e.g., $C_{1-8}$) refer independently to the number of carbon atoms in an alkyl moiety or to the alkyl portion of a larger alkyl-containing substituent. In substituent groups with multiple alkyl groups such as, $(C_{1-6}alkyl)_2amino-$, the $C_{1-6}alkyl$ groups of the dialkylamino may be the same or different.

The term "alkoxy" refers to an —O-alkyl group, wherein the term "alkyl" is as defined above.

The terms "alkenyl" and "alkynyl" refer to straight and branched carbon chains having 2 to 8 carbon atoms, wherein an alkenyl chain contains at least one double bond and an alkynyl chain contains at least one triple bond.

The term "cycloalkyl" refers to saturated or partially saturated, monocyclic or polycyclic hydrocarbon rings of 3 to 14 carbon atoms. Examples of such rings include cyclopropyl, cyclobutyl, cyclopentyl, cyclohexyl, cycloheptyl, and adamantyl.

The term "heterocyclyl" refers to a nonaromatic monocyclic or bicyclic ring system having 3 to 10 ring members that include at least 1 carbon atom and from 1 to 4 heteroatoms independently selected from N, O, and S. Included within the term heterocyclyl is a nonaromatic cyclic ring of 5 to 7 members in which 1 to 2 members are N, or a nonaromatic cyclic ring of 5 to 7 members in which 0, 1 or 2 members are N and up to 2 members are O or S and at least one member must be either N, O, or S; wherein, optionally, the ring contains 0 to 1 unsaturated bonds, and, optionally, when the ring is of 6 or 7 members, it contains up to 2 unsaturated bonds. The carbon atom ring members that form a heterocycle ring may be fully saturated or partially saturated. The term "heterocyclyl" also includes two 5 membered monocyclic heterocycloalkyl groups bridged to form a bicyclic ring. Such groups are not considered to be fully aromatic and are not referred to as heteroaryl groups. When a heterocycle is bicyclic, both rings of the heterocycle are non-aromatic and at least one of the rings contains a heteroatom ring member. Examples of heterocycle groups include, and are not limited to, pyrrolinyl (including 2H-pyrrole, 2-pyrrolinyl or 3-pyrrolinyl), pyrrolidinyl, imidazolinyl, imidazolidinyl, pyrazolinyl, pyrazolidinyl, piperidinyl, morpholinyl, thiomorpholinyl, and piperazinyl. Unless otherwise noted, the heterocycle is attached to its pendant group at any heteroatom or carbon atom that results in a stable structure.

The term "aryl" refers to an unsaturated, aromatic monocyclic or bicyclic ring of 6 to 10 carbon members. Examples of aryl rings include phenyl and naphthalenyl.

The term "heteroaryl" refers to an aromatic monocyclic or bicyclic aromatic ring system having 5 to 10 ring members and which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen or sulfur and, in addition, up to 3 additional nitrogens. In the case of 6 membered rings, the heteroaryl ring preferably contains from 1 to 3 nitrogen atoms. For the case wherein the 6 membered ring has 3 nitrogens, at most 2 nitrogen atoms are adjacent. Examples of heteroaryl groups include furyl, thienyl, pyrrolyl, oxazolyl, thiazolyl, imidazolyl, pyrazolyl, oxazolyl, thiazolyl, oxadiazolyl, triazolyl, thiadiazolyl, pyridinyl, pyridazinyl, pyrimidinyl, pyrazinyl, indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the heteroaryl is attached to its pendant group at any heteroatom or carbon atom that results in a stable structure.

The term "halogen" or "halo" refers to fluorine, chlorine, bromine and iodine atoms.

The term "carboxy" refers to the group —C(=O)OH.

The term "formyl" refers to the group —C(=O)H.

The term "oxo" or "oxido" refers to the group (=O).

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as sub-combinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used thoughout this disclosure, the terminal portion of the designated side chain is described first followed by the adjacent functionality toward the point of attachment. Thus, for example, a "$C_1$-$C_6$ alkylcarbonyl" substituent refers to a group of the formula:

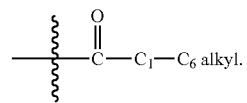

The label "R" at a stereocenter designates that the stereocenter is purely of the R-configuration as defined in the art; likewise, the label "S" means that the stereocenter is purely of the S-configuration. As used herein, the labels "*R" or "*S" at a stereocenter are used to designate that the stereocenter is of pure but unknown absolute configuration.

As used herein, the label "RS" refers to a stereocenter that exists as a mixture of the R- and S-configurations.

A compound containing one stereocenter drawn without a stereo bond designation is a mixture of two enantiomers. A compound containing two stereocenters both drawn without stereo bond designations is a mixture of four diastereomers. A compound with two stereocenters both labeled "RS" and drawn with stereo bond designations is a mixture of two enantiomers with relative stereochemistry as drawn. A compound with two stereocenters both labeled "*RS" and drawn with stereo bond designations is a mixture of two enantiomers with a single, but unknown, relative stereochemistry.

Unlabeled stereocenters drawn without stereo bond designations are mixtures of the R- and S-configurations. For unlabeled stereocenters drawn with stereo bond designations, the relative and absolute stereochemistry is as depicted.

Unless otherwise noted, it is intended that the definition of any substituent or variable at a particular location in a molecule be independent of its definitions elsewhere in that molecule. It is understood that substituents and substitution patterns on the compounds of the present invention can be selected by one of ordinary skill in the art to provide compounds that are chemically stable and that can be readily synthesized by techniques known in the art as well as those methods set forth herein.

The term "subject" refers to an animal, preferably a mammal, most preferably a human, who has been the object of treatment, observation or experiment.

The term "therapeutically effective amount" refers to an amount of an active compound or pharmaceutical agent, including a compound of the present invention, which elicits the biological or medicinal response in a tissue system, animal or human that is being sought by a researcher, veterinarian, medical doctor or other clinician, including reduction or inhibition of an enzyme or a protein activity, or ameliorating symptoms, alleviating conditions, slowing or delaying disease progression, or preventing a disease.

In one embodiment, the term "therapeutically effective amount" refers to the amount of a compound of the present invention that, when administered to a subject, is effective to (1) at least partially alleviate, inhibit, prevent, and/or ameliorate a condition, or a disorder or a disease (i) mediated by MALT1; or (ii) associated with MALT1 activity; or (iii) characterized by activity (normal or abnormal) of MALT1; or (2) reduce or inhibit the activity of MALT1; or (3) reduce or inhibit the expression of MALT1; or (4) modify the protein levels of MALT1.

The term "composition" refers to a product that includes the specified ingredients in therapeutically effective amounts, as well as any product that results, directly, or indirectly, from combinations of the specified ingredients in the specified amounts.

The term "MALT1-mediated" refers to any disease, syndrome, condition, or disorder that might occur in the absence of MALT1 but can occur in the presence of MALT1. Suitable examples of a disease, syndrome, condition, or disorder mediated by MALT1 include, but are not limited to, lymphomas, leukemias, carcinomas, and sarcomas, e.g. non-Hodgkin's lymphoma (NHL), B-cell NHL, diffuse large B-cell lymphoma (DLBCL), mantle cell lymphoma (MCL), follicular lymphoma (FL), mucosa-associated lymphoid tissue (MALT) lymphoma, marginal zone lymphoma, T-cell lymphoma, Hodgkin's lymphoma, Burkitt's lymphoma, multiple myeloma, chonic lymphocytic leukemia (CLL), small lymphocytic lymphoma (SLL), Waldenström macroglobulinemia, lymphoblastic T cell leukemia, chonic myelogenous leukemia (CML), hairy-cell leukemia, acute lymphoblastic T cell leukemia, plasmacytoma, immunoblastic large cell leukemia, megakaryoblastic leukemia, acute megakaryocytic leukemia, promyelocytic leukemia, erytholeukemia, brain (gliomas), glioblastomas, breast cancer, colorectal/colon cancer, prostate cancer, lung cancer including non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head and neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, and GIST (gastrointestinal stromal tumor).

As used herein, the term "MALT1 inhibitor" refers to an agent that inhibits or reduces at least one condition, symptom, disorder, and/or disease of MALT1.

As used herein, unless otherwise noted, the term "affect" or "affected" (when referring to a disease, syndrome, condition or disorder that is affected by the inhibition of MALT1) includes a reduction in the frequency and/or severity of one or more symptoms or manifestations of said disease, syndrome, condition or disorder; and/or includes the prevention of the development of one or more symptoms or manifestations of said disease, syndrome, condition or disorder or the development of the disease, condition, syndrome or disorder.

As used herein, the term "treat", "treating", or "treatment" of any disease, condition, syndrome or disorder refers, in one embodiment, to ameliorating the disease, condition, syndrome or disorder (i.e. slowing or arresting or reducing the development of the disease or at least one of the clinical symptoms thereof). In another embodiment, "treat", "treating", or "treatment" refers to alleviating or ameliorating at lease one physical parameter including those which may not be discernible by the patient. In a further embodiment, "treat", "treating", or "treatment" refers to modulating the disease, condition, syndrome or disorder either physically (e.g. stabilization of a discernible symptom), physiologically, (e.g. stabilization of a physical parameter), or both. In yet another embodiment, "treat", "treating", or "treatment" refers to preventing or delaying the onset or development or progression of the disease, condition, syndrome or disorder.

The compounds of the instant invention are useful in methods for treating or ameliorating a disease, a syndrome, a condition or a disorder that is affected by the inhibition of MALT1. Such methods comprise, consist of and/or consist essentially of administering to a subject, including an animal, a mammal, and a human in need of such treatment, amelioration and/or prevention, a therapeutically effective amount of a compound of Formula (I), or an enantiomer, diastereomer, solvate or pharmaceutically acceptable salt thereof.

One embodiment of the present invention is directed to a method of treating a MALT1-dependent or MALT1-mediated disease or condition in a subject in need thereof, including an animal, a mammal, and a human in need of such treatment, comprising administering to the subject a therapeutically effective amount of a compound of Formula (I).

In another embodiment, the MALT1-dependent or MALT1-mediated disease or condition is selected from cancers of hematopoietic origin or solid tumors such as chonic myelogenous leukemia, myeloid leukemia, non-Hodgkin lymphoma, and other B cell lymphomas.

In particular, the compounds of Formula (I), or an enantiomer, diastereomer, solvate or pharmaceutically acceptable salt form thereof are useful for treating or ameliorating diseases, syndromes, conditions, or disorders such as diffuse large B-cell lymphoma (DLBCL), mantle cell lymphoma (MCL), follicular lymphoma (FL), and mucosa-associated lymphoid tissue (MALT) lymphoma.

More particularly, the compounds of Formula (I), or an enantiomer, diastereomer, solvate or pharmaceutically acceptable salt form thereof, are useful for treating or ameliorating diffuse large B-cell lymphoma (DLBCL), mantle cell lymphoma (MCL), follicular lymphoma (FL), and mucosa-associated lymphoid tissue (MALT) lymphoma, comprising administering to a subject in need thereof a therapeutically effective amount of a compound of Formula (I), or an enantiomer, diastereomer, solvate or pharmaceutically acceptable salt form thereof as herein defined.

Further, the compounds of Formula (I), or an enantiomer, diastereomer, solvate or pharmaceutically acceptable salt form thereof, are useful for treating or ameliorating an immunological disease, syndrome, disorder, or condition selected from the group consisting of rheumatoid arthritis (RA), psoritic arthritis (PsA), psorisis (Pso), ulcerative colitis (UC), Crohn's disease, systemic lupus erythematosus (SLE), asthma, and chronic obstructive pulmonary disease (COPD).

Another embodiment of the invention is directed to compounds of Formula (I)

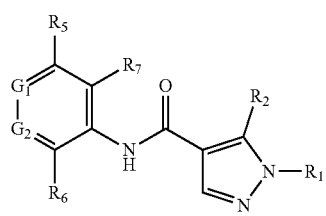

Formula (I)

wherein $R_1$ is a heteroaryl independently selected from the group consisting of pyrazolo[1,5-a]pyridinyl and imidazo[1,2-a]pyridinyl; wherein $R_1$ is optionally independently substituted with one or two substituents selected from methyl, ethyl, fluoro, chloro, cyano, or aminocarbonyl;

$R_2$ is independently selected from the group consisting of $C_{1-4}$alkyl, 1-methoxy-ethyl, difluoromethyl, fluoro, chloro, bromo, cyano, methylsulfonyl and trifluoromethyl;

$G_1$ is N or $C(R_4)$;

$G_2$ is N or $C(R_3)$; such that only one of $G_1$ and $G_2$ are N in any instance;

$R_3$ is independently selected from the group consisting of trifluoromethyl, cyano, $C_{1-4}$alkyl, fluoro, chloro, bromo, methylcarbonyl, methylthio, methylsulfinyl, and methanesulfonyl;

$R_4$ is independently selected from the group consisting of triazolyl, 1-(methoxy)ethyl, oxazolyl, isoxazolyl, pyrazolyl, pyrrolyl, thiazolyl, tetrazolyl, oxadiazolyl, and imidazolyl; wherein $R_4$ other than 1-methoxyethyl is optionally independently substituted with one or two substituents selected from oxo, $C_{1-4}$alkyl, carboxy, methoxycarbonyl, aminocarbonyl, hydroxymethyl, aminomethyl, (dimethylamino)methyl, amino, methoxymethyl, trifluoromethyl, amino($C_{2-4}$alkyl)amino, or cyano; or $R_4$ is independently selected from the group consisting of tetrahydrofuran-2-yl, $(CH_3)_2S(=O)(=N)-$, and $CH_3(NH=)(O=)S-$; or $R_4$ is hydrogen when $G_2$ is N;

$R_5$ is independently selected from the group consisting of hydrogen, methyl, ethyl, chloro, bromo, trifluoromethyl, methylthio, methylsulfonyl, methoxy, and cyano;

$R_6$ is hydrogen, $C_{1-4}$alkyl, fluoro, 2-methoxy-ethoxy, chloro, cyano, or trifluoromethyl;

$R_7$ is hydrogen, methyl, ethyl, or fluoro;

or an enantiomer, diastereomer, or pharmaceutically acceptable salt form thereof.

Additional embodiments of the present invention include a compound of Formula (I)

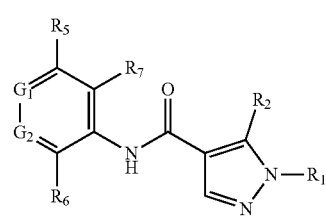

Formula (I)

wherein

AA) $R_1$ is a heteroaryl independently selected from the group consisting of pyrazolo[1,5-a]pyridin-4-yl and imidazo[1,2-a]pyridin-5-yl; wherein $R_1$ is optionally independently substituted with a substituent selected from the group consisting of chloro, aminocarbonyl, and cyano;

BB) $R_1$ is a heteroaryl independently selected from the group consisting of (7-aminocarbonyl)pyrazolo[1,5-a]pyridin-4-yl, (7-chloro)pyrazolo[1,5-a]pyridin-4-yl, (7-cyano)pyrazolo[1,5-a]pyridin-4-yl, (8-aminocarbonyl)imidazo[1,2-a]pyridin-5-yl, (8-chloro)imidazo[1,2-a]pyridin-5-yl, (8-cyano)imidazo[1,2-a]pyridin-5-yl, (8-fluoro)imidazo[1,2-a]pyridin-5-yl;

CC) $R_2$ is trifluoromethyl or methyl sulfonyl;

DD) $R_3$ is independently selected from the group consisting of trifluoromethyl, cyano, and chloro;

EE) $R_3$ is trifluoromethyl;

FF) $G_2$ is N;

GG) $R_4$ is independently selected from the group consisting of 2H-1,2,3-triazol-2-yl, oxazol-2-yl, 4-methyloxazol-2-yl, 5-methyloxazolyl-2-yl, 1H-pyrazol-1-yl and tetrahydrofuran-2-yl; or $R_4$ is hydrogen when $G_2$ is N;

HH) $R_4$ is independently selected from the group consisting 1(*R)-methoxyethyl, 1(*S)-methoxyethyl, (*R)-tetrahydrofuran-2-yl, and (*S)-tetrahydrofuran-2-yl;

II) $R_5$ is hydrogen, chloro, bromo or trifluoromethyl;

and any combination of embodiments AA) through II) above, provided it is understood that combinations in which different embodiments of the same substituent would be combined are excluded; such that only one of $G_1$ and $G_2$ are N in any instance; or an enantiomer, diastereomer, or pharmaceutically acceptable salt form thereof.

Embodiments of the present invention include a compound of Formula (I)

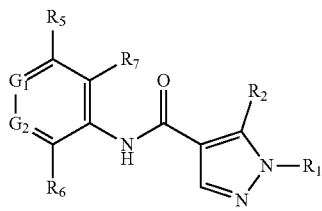

Formula (I)

wherein

R₁ is a heteroaryl independently selected from the group consisting of pyrazolo[1,5-a]pyridinyl and imidazo[1,2-a]pyridinyl; wherein R₁ is optionally independently substituted with one or two substituents selected from methyl, ethyl, fluoro, chloro, cyano, or aminocarbonyl;

R₂ is trifluoromethyl or methyl sulfonyl;

G₁ is N or C(R₄);

G₂ is N or C(R₃); such that only one of G₁ and G₂ are N in any instance;

R₃ is trifluoromethyl;

R₄ is independently selected from the group consisting of triazolyl, 1-(methoxy)ethyl, oxazol-2-yl, 4-methyloxazol-2-yl, 5-methyloxazolyl-2-yl, 1H-pyrazol-1-yl, tetrahydrofuran-2-yl, (CH₃)₂S(=O)(=N)—, and CH₃(NH=)(O=)S—; or R₄ is hydrogen when G₂ is N;

R₅ is independently selected from the group consisting of hydrogen, methyl, ethyl, chloro, bromo, trifluoromethyl, methoxy, and cyano;

R₆ is hydrogen, methyl, or trifluoromethyl;

R₇ is hydrogen, methyl, ethyl, or fluoro;

or an enantiomer, diastereomer, or pharmaceutically acceptable salt form thereof.

Another embodiment of the present invention includes a compound of Formula (I)

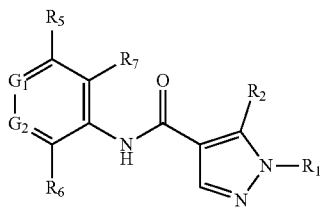

Formula (I)

wherein

R₁ is a heteroaryl independently selected from the group consisting of (7-aminocarbonyl)pyrazolo[1,5-a]pyridin-4-yl, (7-chloro)pyrazolo[1,5-a]pyridin-4-yl, (7-cyano)pyrazolo[1,5-a]pyridin-4-yl, (8-aminocarbonyl)imidazo[1,2-a]pyridin-5-yl, (8-chloro)imidazo[1,2-a]pyridin-5-yl, (8-cyano)imidazo[1,2-a]pyridin-5-yl, (8-fluoro)imidazo[1,2-a]pyridin-5-yl;

R₂ is trifluoromethyl or methyl sulfonyl;

G₁ is N or C(R₄);

G₂ is N or C(R₃); such that only one of G₁ and G₂ are N in any instance;

R₃ is trifluoromethyl;

R₄ is independently selected from the group consisting of 1(*R)-methoxyethyl, 1(*S)-methoxyethyl, (*R)-tetrahydrofuran-2-yl, and (S)-tetrahydrofuran-2-yl; or R₄ is hydrogen when G₂ is N;

R₅ is independently selected from the group consisting of hydrogen, methyl, ethyl, chloro, bromo, trifluoromethyl, methoxy, and cyano;

R₆ is hydrogen, methyl, or trifluoromethyl;

R₇ is hydrogen, methyl, ethyl, or fluoro;

or an enantiomer, diastereomer, or pharmaceutically acceptable salt form thereof.

Additional embodiments of the present invention include compounds of Formula (I) as herein defined, or an enantiomer, diastereomer, solvate, or a pharmaceutically acceptable salt form thereof, as exemplified in the listing in Table 1, below.

TABLE 1

| Structure | Cpd No. | Cpd Name |
|---|---|---|
| 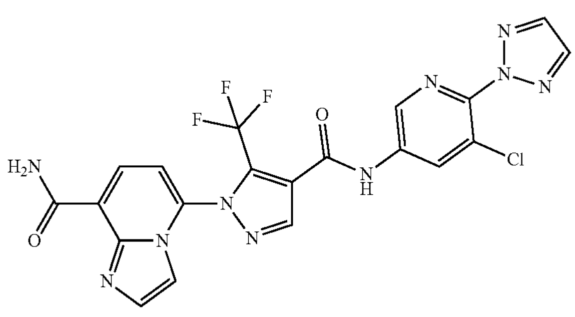 [SMILES: NC(=O)c1ccc(-n2ncc(C(=O)Nc3cnc(-n4nccn4)c(Cl)c3)c2C(F)(F)F)n2ccnc12] | 1 | 5-(4-((5-chloro-6-(2H-1,2,3-triazol-2-yl)pyridin-3-yl)carbamoyl)-5-(trifluoromethyl)-1H-pyrazol-1-yl)imidazo[1,2-a]pyridine-8-carboxamide |

TABLE 1-continued

| Structure | Cpd No. | Cpd Name |
|---|---|---|
| 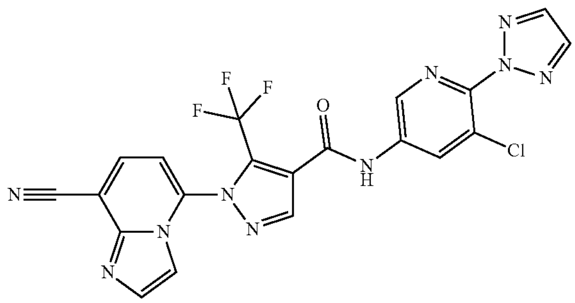 [SMILES: N#Cc1ccc(-n2ncc(C(=O)Nc3cnc(-n4nccn4)c(Cl)c3)c2C(F)(F)F)n2ccnc12] | 2 | N-(5-chloro-6-(2H-1,2,3-triazol-2-yl)pyridin-3-yl)-1-(8-cyanoimidazo[1,2-a]pyridin-5-yl)-5-(trifluoromethyl)-1H-pyrazole-4-carboxamide |
| 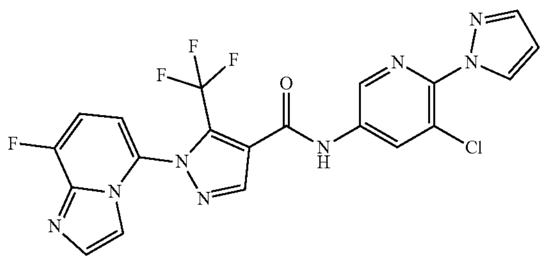 [SMILES: O=C(Nc1cnc(-n2cccn2)c(Cl)c1)c1cnn(-c2ccc(F)c3nccn23)c1C(F)(F)F] | 3 | N-(5-chloro-6-(1H-pyrazol-1-yl)pyridin-3-yl)-1-(8-fluoroimidazo[1,2-a]pyridin-5-yl)-5-(trifluoromethyl)-1H-pyrazole-4-carboxamide |
| 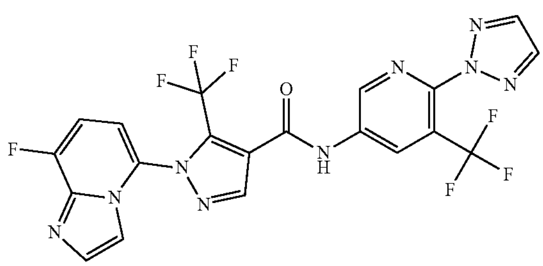 [SMILES: O=C(Nc1cnc(-n2nccn2)c(C(F)(F)F)c1)c1cnn(-c2ccc(F)c3nccn23)c1C(F)(F)F] | 4 | N-(6-(2H-1,2,3-triazol-2-yl)-5-(trifluoromethyl)pyridin-3-yl)-1-(8-fluoroimidazo[1,2-a]pyridin-5-yl)-5-(trifluoromethyl)-1H-pyrazole-4-carboxamide |
| 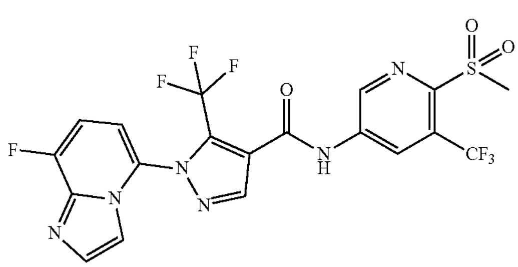 [SMILES: CS(=O)(=O)c1ncc(NC(=O)c2cnn(-c3ccc(F)c4nccn34)c2C(F)(F)F)cc1C(F)(F)F] | 5 | 1-(8-fluoroimidazo[1,2-a]pyridin-5-yl)-N-(6-(methylsulfonyl)-5-(trifluoromethyl)pyridin-3-yl)-5-(trifluoromethyl)-1H-pyrazole-4-carboxamide |
| 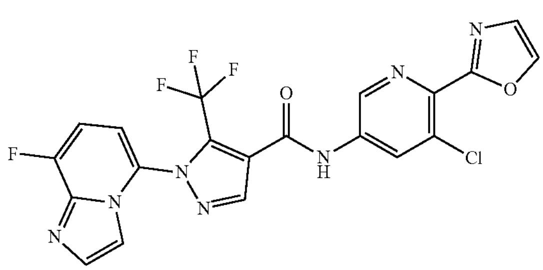 [SMILES: O=C(Nc1cnc(-c2ncco2)c(Cl)c1)c1cnn(-c2ccc(F)c3nccn23)c1C(F)(F)F] | 6 | N-(5-chloro-6-(oxazol-2-yl)pyridin-3-yl)-1-(8-fluoroimidazo[1,2-a]pyridin-5-yl)-5-(trifluoromethyl)-1H-pyrazole-4-carboxamide |

TABLE 1-continued

| Structure | Cpd No. | Cpd Name |
|---|---|---|
| 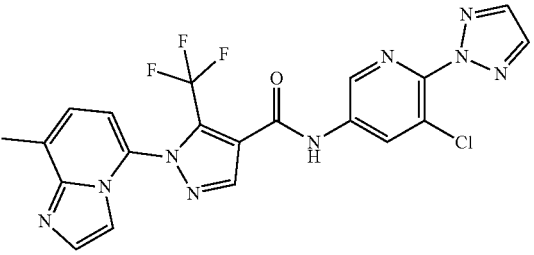 [SMILES: Cc1ccc(-n2ncc(C(=O)Nc3cnc(-n4nccn4)c(Cl)c3)c2C(F)(F)F)n2ccnc12] | 7 | N-(5-chloro-6-(2H-1,2,3-triazol-2-yl)pyridin-3-yl)-1-(8-methylimidazo[1,2-a]pyridin-5-yl)-5-(trifluoromethyl)-1H-pyrazole-4-carboxamide |
| 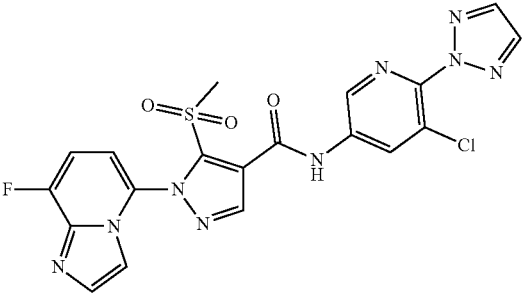 [SMILES: CS(=O)(=O)c1c(C(=O)Nc2cnc(-n3nccn3)c(Cl)c2)cnn1-c1ccc(F)c2nccn12] | 8 | N-(5-chloro-6-(2H-1,2,3-triazol-2-yl)pyridin-3-yl)-1-(8-fluoroimidazo[1,2-a]pyridin-5-yl)-5-(methylsulfonyl)-1H-pyrazole-4-carboxamide |
| 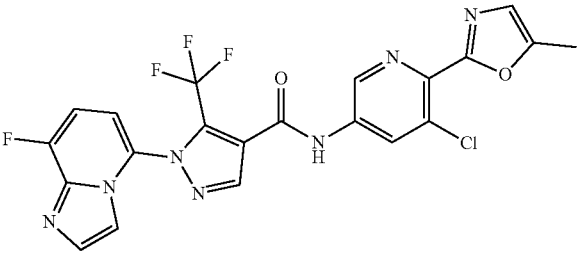 [SMILES: Cc1cnc(-c2ncc(NC(=O)c3cnn(-c4ccc(F)c5nccn45)c3C(F)(F)F)cc2Cl)o1] | 9 | N-(5-chloro-6-(5-methyloxazol-2-yl)pyridin-3-yl)-1-(8-fluoroimidazo[1,2-a]pyridin-5-yl)-5-(trifluoromethyl)-1H-pyrazole-4-carboxamide |
| 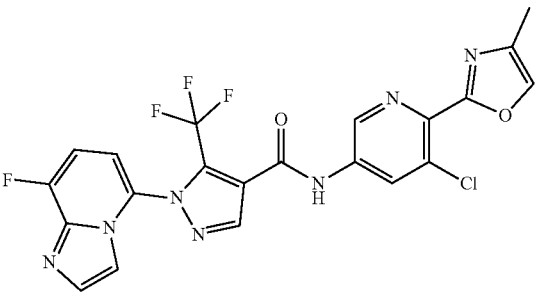 [SMILES: Cc1coc(-c2ncc(NC(=O)c3cnn(-c4ccc(F)c5nccn45)c3C(F)(F)F)cc2Cl)n1] | 10 | N-(5-chloro-6-(4-methyloxazol-2-yl)pyridin-3-yl)-1-(8-fluoroimidazo[1,2-a]pyridin-5-yl)-5-(trifluoromethyl)-1H-pyrazole-4-carboxamide |
| 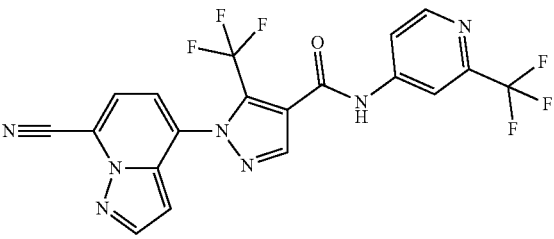 [SMILES: N#Cc1ccc(-n2ncc(C(=O)Nc3ccnc(C(F)(F)F)c3)c2C(F)(F)F)c2ccnn12] | 11 | 1-(7-cyanopyrazolo[1,5-a]pyridin-4-yl)-5-(trifluoromethyl)-N-(2-(trifluoromethyl)pyridin-4-yl)-1H-pyrazole-4-carboxamide |

TABLE 1-continued

| Structure | Cpd No. | Cpd Name |
|---|---|---|
| 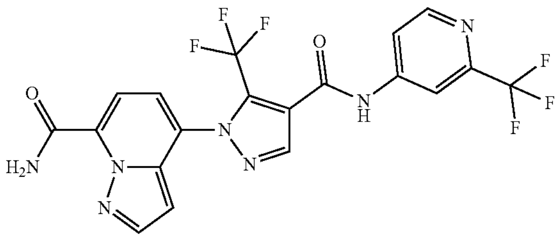 [SMILES: NC(=O)c1ccc(-n2ncc(C(=O)Nc3ccnc(C(F)(F)F)c3)c2C(F)(F)F)c2ccnn12] | 12 | 4-(5-(trifluoromethyl)-4-((2-(trifluoromethyl)pyridin-4-yl)carbamoyl)-1H-pyrazol-1-yl)pyrazolo[1,5-a]pyridine-7-carboxamide |
| 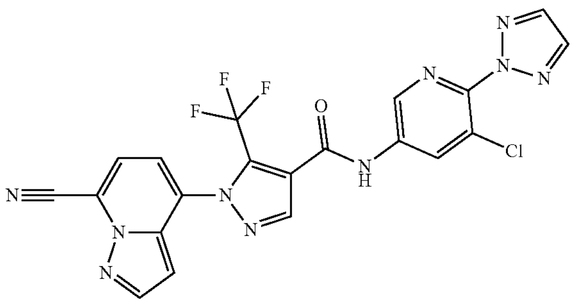 [SMILES: N#Cc1ccc(-n2ncc(C(=O)Nc3cnc(-n4nccn4)c(Cl)c3)c2C(F)(F)F)c2ccnn12] | 13 | N-(5-chloro-6-(2H-1,2,3-triazol-2-yl)pyridin-3-yl)-1-(7-cyanopyrazolo[1,5-a]pyridin-4-yl)-5-(trifluoromethyl)-1H-pyrazole-4-carboxamide |
| 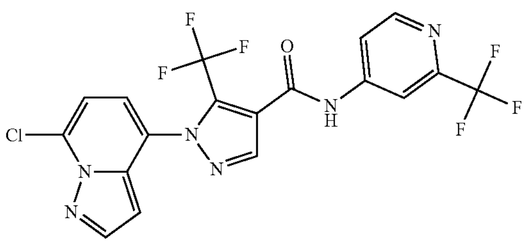 [SMILES: O=C(Nc1ccnc(C(F)(F)F)c1)c1cnn(-c2ccc(Cl)n3nccc23)c1C(F)(F)F] | 14 | 1-(7-chloropyrazolo[1,5-a]pyridin-4-yl)-5-(trifluoromethyl)-N-(2-(trifluoromethyl)pyridin-4-yl)-1H-pyrazole-4-carboxamide |
| 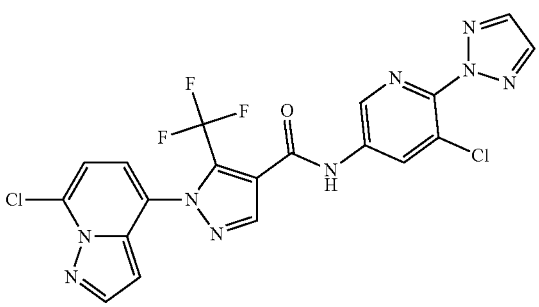 [SMILES: O=C(Nc1cnc(-n2nccn2)c(Cl)c1)c1cnn(-c2ccc(Cl)n3nccc23)c1C(F)(F)F] | 15 | N-(5-chloro-6-(2H-1,2,3-triazol-2-yl)pyridin-3-yl)-1-(7-chloropyrazolo[1,5-a]pyridin-4-yl)-5-(trifluoromethyl)-1H-pyrazole-4-carboxamide |
| 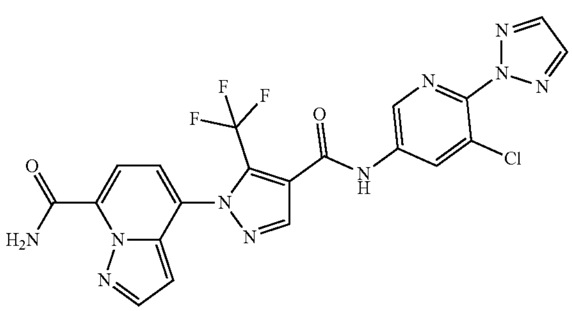 [SMILES: NC(=O)c1ccc(-n2ncc(C(=O)Nc3cnc(-n4nccn4)c(Cl)c3)c2C(F)(F)F)c2ccnn12] | 16 | 4-(4-((5-chloro-6-(2H-1,2,3-triazol-2-yl)pyridin-3-yl)carbamoyl)-5-(trifluoromethyl)-1H-pyrazol-1-yl)pyrazolo[1,5-a]pyridine-7-carboxamide |

TABLE 1-continued

| Structure | Cpd No. | Cpd Name |
|---|---|---|
| 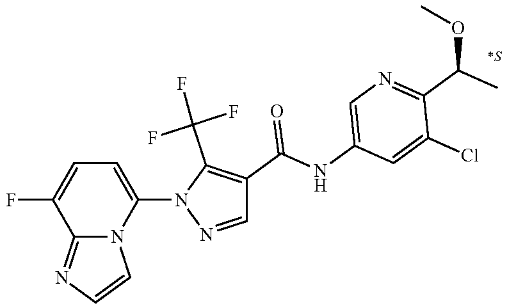 [SMILES: CO[C@@H](C)c1ncc(NC(=O)c2cnn(-c3ccc(F)c4nccn34)c2C(F)(F)F)cc1Cl] | 17 | (*S)-N-(5-chloro-6-(1-methoxyethyl)pyridin-3-yl)-1-(8-fluoroimidazo[1,2-a]pyridin-5-yl)-5-(trifluoromethyl)-1H-pyrazole-4-carboxamide |
| 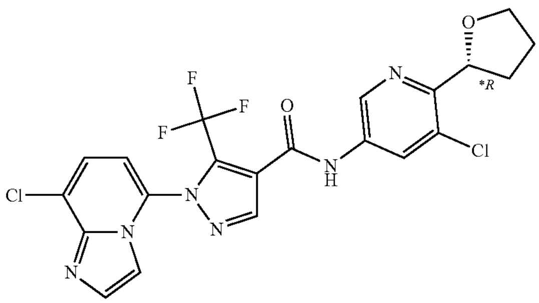 [SMILES: O=C(Nc1cnc([C@H]2CCCO2)c(Cl)c1)c1cnn(-c2ccc(Cl)c3nccn23)c1C(F)(F)F] | 18 | (*R)-N-(5-chloro-6-(tetrahydrofuran-2-yl)pyridin-3-yl)-1-(8-chloroimidazo[1,2-a]pyridin-5-yl)-5-(trifluoromethyl)-1H-pyrazole-4-carboxamide |
| 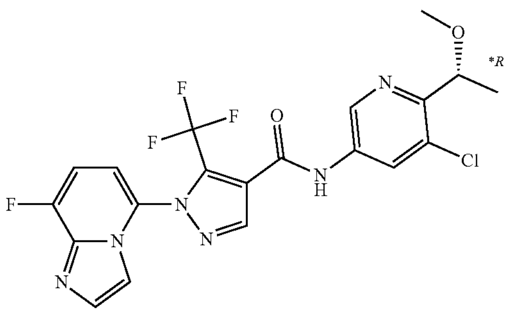 [SMILES: CO[C@H](C)c1ncc(NC(=O)c2cnn(-c3ccc(F)c4nccn34)c2C(F)(F)F)cc1Cl] | 19 | (*R)-N-(5-chloro-6-(1-methoxyethyl)pyridin-3-yl)-1-(8-fluoroimidazo[1,2-a]pyridin-5-yl)-5-(trifluoromethyl)-1H-pyrazole-4-carboxamide |
| 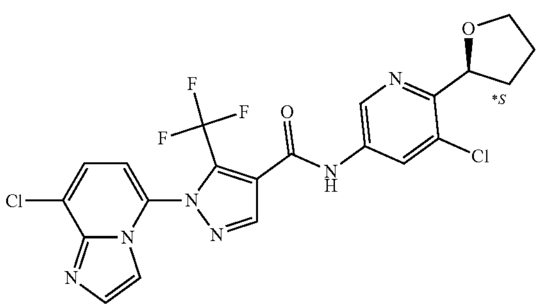 [SMILES: O=C(Nc1cnc([C@@H]2CCCO2)c(Cl)c1)c1cnn(-c2ccc(Cl)c3nccn23)c1C(F)(F)F] | 20 | (*S)-N-(5-chloro-6-(tetrahydrofuran-2-yl)pyridin-3-yl)-1-(8-chloroimidazo[1,2-a]pyridin-5-yl)-5-(trifluoromethyl)-1H-pyrazole-4-carboxamide |
| 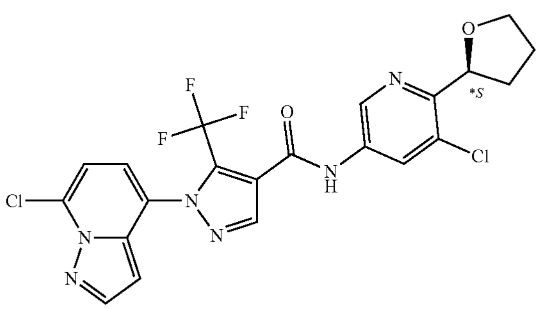 [SMILES: O=C(Nc1cnc([C@@H]2CCCO2)c(Cl)c1)c1cnn(-c2ccc(Cl)n3nccc23)c1C(F)(F)F] | 21 | (*S)-N-(5-chloro-6-(tetrahydrofuran-2-yl)pyridin-3-yl)-1-(7-chloropyrazolo[1,5-a]pyridin-4-yl)-5-(trifluoromethyl)-1H-pyrazole-4-carboxamide |

TABLE 1-continued

| Structure | Cpd No. | Cpd Name |
|---|---|---|
| 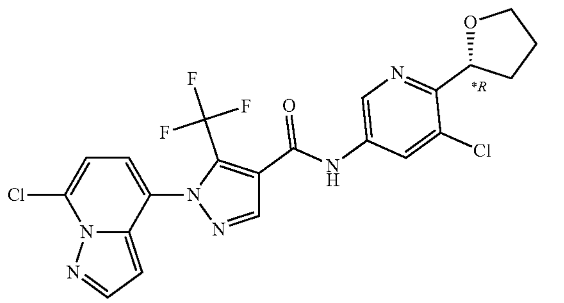 [SMILES: O=C(Nc1cnc([C@H]2CCCO2)c(Cl)c1)c1cnn(-c2ccc(Cl)n3nccc23)c1C(F)(F)F] | 22 | (*R)-N-(5-chloro-6-(tetrahydrofuran-2-yl)pyridin-3-yl)-1-(7-chloropyrazolo[1,5-a]pyridin-4-yl)-5-(trifluoromethyl)-1H-pyrazole-4-carboxamide |
| 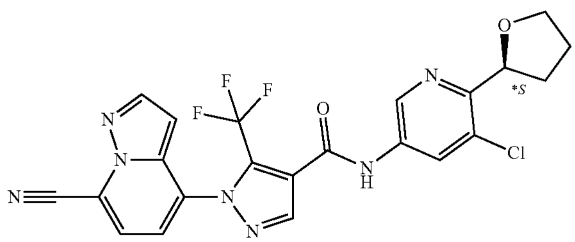 [SMILES: N#Cc1ccc(-n2ncc(C(=O)Nc3cnc([C@@H]4CCCO4)c(Cl)c3)c2C(F)(F)F)c2ccnn12] | 23 | (*S)-N-(5-chloro-6-(tetrahydrofuran-2-yl)pyridin-3-yl)-1-(7-cyanopyrazolo[1,5-a]pyridin-4-yl)-5-(trifluoromethyl)-1H-pyrazole-4-carboxamide |
| 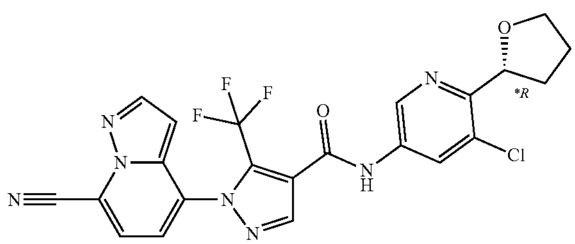 [SMILES: N#Cc1ccc(-n2ncc(C(=O)Nc3cnc([C@H]4CCCO4)c(Cl)c3)c2C(F)(F)F)c2ccnn12] | 24 | (*R)-N-(5-chloro-6-(tetrahydrofuran-2-yl)pyridin-3-yl)-1-(7-cyanopyrazolo[1,5-a]pyridin-4-yl)-5-(trifluoromethyl)-1H-pyrazole-4-carboxamide |
| 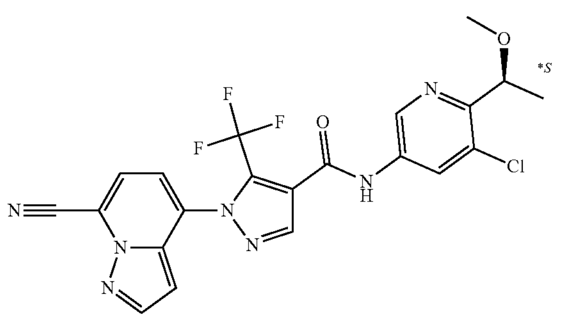 [SMILES: CO[C@@H](C)c1ncc(NC(=O)c2cnn(-c3ccc(C#N)n4nccc34)c2C(F)(F)F)cc1Cl] | 25 | (*S)-N-(5-chloro-6-(1-methoxyethyl)pyridin-3-yl)-1-(7-cyanopyrazolo[1,5-a]pyridin-4-yl)-5-(trifluoromethyl)-1H-pyrazole-4-carboxamide |
| 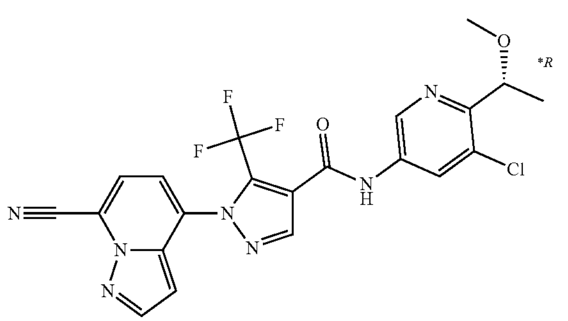 [SMILES: CO[C@H](C)c1ncc(NC(=O)c2cnn(-c3ccc(C#N)n4nccc34)c2C(F)(F)F)cc1Cl] | 26 | (*R)-N-(5-chloro-6-(1-methoxyethyl)pyridin-3-yl)-1-(7-cyanopyrazolo[1,5-a]pyridin-4-yl)-5-(trifluoromethyl)-1H-pyrazole-4-carboxamide |

TABLE 1-continued

| Structure | Cpd No. | Cpd Name |
|---|---|---|
| 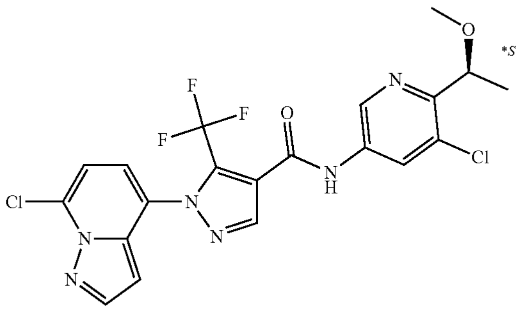 [SMILES: CO[C@@H](C)c1ncc(NC(=O)c2cnn(-c3ccc(Cl)n4nccc34)c2C(F)(F)F)cc1Cl] | 27 | (*S)-N-(5-chloro-6-(1-methoxyethyl)pyridin-3-yl)-1-(7-chloropyrazolo[1,5-a]pyridin-4-yl)-5-(trifluoromethyl)-1H-pyrazole-4-carboxamide |
| 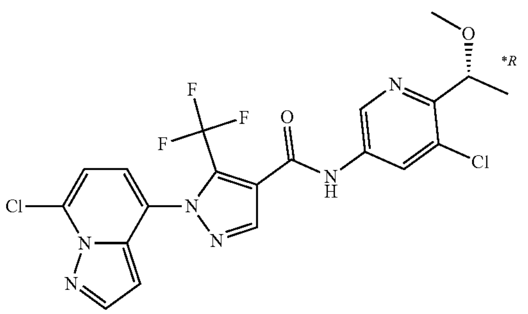 [SMILES: CO[C@H](C)c1ncc(NC(=O)c2cnn(-c3ccc(Cl)n4nccc34)c2C(F)(F)F)cc1Cl] | 28 | (*R)-N-(5-chloro-6-(1-methoxyethyl)pyridin-3-yl)-1-(7-chloropyrazolo[1,5-a]pyridin-4-yl)-5-(trifluoromethyl)-1H-pyrazole-4-carboxamide |
| 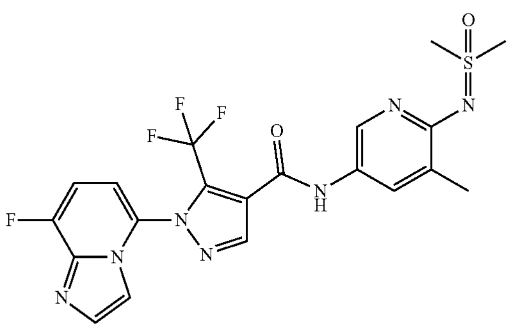 [SMILES: Cc1cc(NC(=O)c2cnn(-c3ccc(F)c4nccn34)c2C(F)(F)F)cnc1N=S(C)(C)=O] | 29 | N-(6-((dimethyl(oxo)-$\lambda^6$-sulfanylidene)amino)-5-methylpyridin-3-yl)-1-(8-fluoroimidazo[1,2-a]pyridin-5-yl)-5-(trifluoromethyl)-1H-pyrazole-4-carboxamide |
| 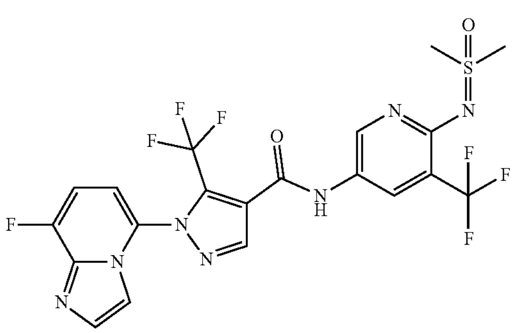 [SMILES: CS(C)(=O)=Nc1ncc(NC(=O)c2cnn(-c3ccc(F)c4nccn34)c2C(F)(F)F)cc1C(F)(F)F] | 30 | N-(6-((dimethyl(oxo)-$\lambda^6$-sulfanylidene)amino)-5-(trifluoromethyl)pyridin-3-yl)-1-(8-fluoroimidazo[1,2-a]pyridin-5-yl)-5-(trifluoromethyl)-1H-pyrazole-4-carboxamide |
| 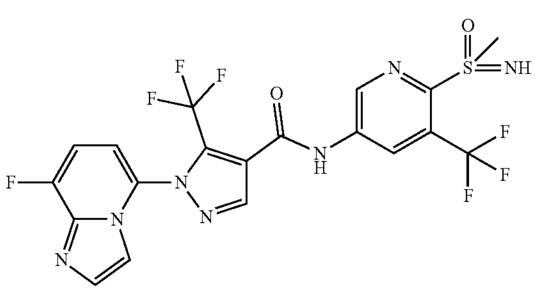 [SMILES: CS(=N)(=O)c1ncc(NC(=O)c2cnn(-c3ccc(F)c4nccn34)c2C(F)(F)F)cc1C(F)(F)F] | 31 | 1-(8-fluoroimidazo[1,2-a]pyridin-5-yl)-N-(6-(S-methylsulfonimidoyl)-5-(trifluoromethyl)pyridin-3-yl)-5-(trifluoromethyl)-1H-pyrazole-4-carboxamide |

TABLE 1-continued

| Structure | Cpd No. | Cpd Name |
|---|---|---|
| 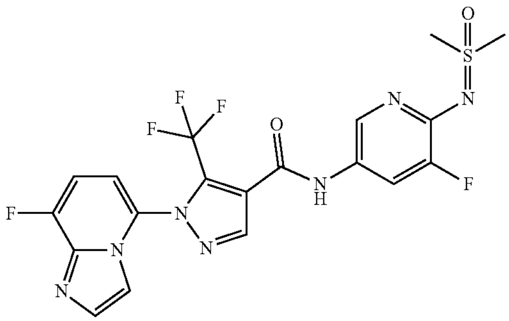 | 32 | N-(6-((dimethyl(oxo)-λ⁶-sulfanylidene)amino)-5-fluoropyridin-3-yl)-1-(8-fluoroimidazo[1,2-a]pyridin-5-yl)-5-(trifluoromethyl)-1H-pyrazole-4-carboxamide |
| 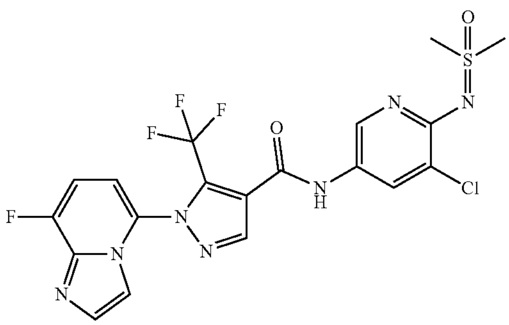 | 33 | N-(5-chloro-6-((dimethyl(oxo)-λ⁶-sulfanylidene)amino)pyridin-3-yl)-1-(8-fluoroimidazo[1,2-a]pyridin-5-yl)-5-(trifluoromethyl)-1H-pyrazole-4-carboxamide |

In a further embodiment, the invention is directed to a compound of Formula (I)

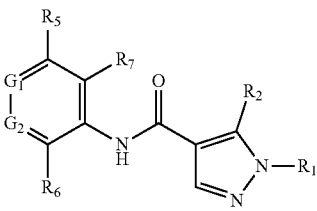

Formula (I)

selected from the group consisting of 5-(4-((5-chloro-6-(2H-1,2,3-triazol-2-yl)pyridin-3-yl)carbamoyl)-5-(trifluoromethyl)-1H-pyrazol-1-yl)imidazo[1,2-a]pyridine-8-carboxamide;

N-(5-chloro-6-(2H-1,2,3-triazol-2-yl)pyridin-3-yl)-1-(8-cyanoimidazo[1,2-a]pyridin-5-yl)-5-(trifluoromethyl)-1H-pyrazole-4-carboxamide;

N-(5-chloro-6-(1H-pyrazol-1-yl)pyridin-3-yl)-1-(8-fluoroimidazo[1,2-a]pyridin-5-yl)-5-(trifluoromethyl)-1H-pyrazole-4-carboxamide;

N-(6-(2H-1,2,3-triazol-2-yl)-5-(trifluoromethyl)pyridin-3-yl)-1-(8-fluoroimidazo[1,2-c]pyridin-5-yl)-5-(trifluoromethyl)-1H-pyrazole-4-carboxamide;

1-(8-fluoroimidazo[1,2-a]pyridin-5-yl)-N-(6-(methylsulfonyl)-5-(trifluoromethyl)pyridin-3-yl)-5-(trifluoromethyl)-1H-pyrazole-4-carboxamide;

N-(5-chloro-6-(oxazol-2-yl)pyridin-3-yl)-1-(8-fluoroimidazo[1,2-a]pyridin-5-yl)-5-(trifluoromethyl)-1H-pyrazole-4-carboxamide;

N-(5-chloro-6-(2H-1,2,3-triazol-2-yl)pyridin-3-yl)-1-(8-methylimidazo[1,2-a]pyridin-5-yl)-5-(trifluoromethyl)-1H-pyrazole-4-carboxamide;

N-(5-chloro-6-(2H-1,2,3-triazol-2-yl)pyridin-3-yl)-1-(8-fluoroimidazo[1,2-a]pyridin-5-yl)-5-(methylsulfonyl)-1H-pyrazole-4-carboxamide;

N-(5-chloro-6-(5-methyloxazol-2-yl)pyridin-3-yl)-1-(8-fluoroimidazo[1,2-a]pyridin-5-yl)-5-(trifluoromethyl)-1H-pyrazole-4-carboxamide;

N-(5-chloro-6-(4-methyloxazol-2-yl)pyridin-3-yl)-1-(8-fluoroimidazo[1,2-a]pyridin-5-yl)-5-(trifluoromethyl)-1H-pyrazole-4-carboxamide;

1-(7-cyanopyrazolo[1,5-a]pyridin-4-yl)-5-(trifluoromethyl)-N-(2-(trifluoromethyl)pyridin-4-yl)-1H-pyrazole-4-carboxamide;

4-(5-(trifluoromethyl)-4-((2-(trifluoromethyl)pyridin-4-yl)carbamoyl)-1H-pyrazol-1-yl)pyrazolo[1,5-a]pyridine-7-carboxamide;

N-(5-chloro-6-(2H-1,2,3-triazol-2-yl)pyridin-3-yl)-1-(7-cyanopyrazolo[1,5-a]pyridin-4-yl)-5-(trifluoromethyl)-1H-pyrazole-4-carboxamide;

1-(7-chloropyrazolo[1,5-a]pyridin-4-yl)-5-(trifluoromethyl)-N-(2-(trifluoromethyl)pyridin-4-yl)-1H-pyrazole-4-carboxamide;

4-(4-((5-chloro-6-(2H-1,2,3-triazol-2-yl)pyridin-3-yl)carbamoyl)-5-(trifluoromethyl)-1H-pyrazol-1-yl)pyrazolo[1,5-a]pyridine-7-carboxamide;

S)—N-(5-chloro-6-(1-methoxyethyl)pyridin-3-yl)-1-(8-fluoroimidazo[1,2-a]pyridin-5-yl)-5-(trifluoromethyl)-1H-pyrazole-4-carboxamide;

(*R)—N-(5-chloro-6-(tetrahydrofuran-2-yl)pyridin-3-yl)-1-(8-chloroimidazo[1,2-a]pyridin-5-yl)-5-(trifluoromethyl)-1H-pyrazole-4-carboxamide;

(*R)—N-(5-chloro-6-(tetrahydrofuran-2-yl)pyridin-3-yl)-1-(8-chloroimidazo[1,2-a]pyridin-5-yl)-5-(trifluoromethyl)-1H-pyrazole-4-carboxamide;

(*R)—N-(5-chloro-6-(1-methoxyethyl)pyridin-3-yl)-1-(8-fluoroimidazo[1,2-a]pyridin-5-yl)-5-(trifluoromethyl)-1H-pyrazole-4-carboxamide;

(*S)—N-(5-chloro-6-(tetrahydrofuran-2-yl)pyridin-3-yl)-1-(8-chloroimidazo[1,2-a]pyridin-5-yl)-5-(trifluoromethyl)-1H-pyrazole-4-carboxamide;
(*S)—N-(5-chloro-6-(tetrahydrofuran-2-yl)pyridin-3-yl)-1-(7-chloropyrazolo[1,5-a]pyridin-4-yl)-5-(trifluoromethyl)-1H-pyrazole-4-carboxamide;
(*R)—N-(5-chloro-6-(tetrahydrofuran-2-yl)pyridin-3-yl)-1-(7-chloropyrazolo[1,5-a]pyridin-4-yl)-5-(trifluoromethyl)-1H-pyrazole-4-carboxamide;
(*S)—N-(5-chloro-6-(tetrahydrofuran-2-yl)pyridin-3-yl)-1-(7-cyanopyrazolo[1,5-a]pyridin-4-yl)-5-(trifluoromethyl)-1H-pyrazole-4-carboxamide;
(*R)—N-(5-chloro-6-(tetrahydrofuran-2-yl)pyridin-3-yl)-1-(7-cyanopyrazolo[1,5-a]pyridin-4-yl)-5-(trifluoromethyl)-1H-pyrazole-4-carboxamide;
(*S)—N-(5-chloro-6-(1-methoxyethyl)pyridin-3-yl)-1-(7-cyanopyrazolo[1,5-a]pyridin-4-yl)-5-(trifluoromethyl)-1H-pyrazole-4-carboxamide;
(*R)—N-(5-chloro-6-(1-methoxyethyl)pyridin-3-yl)-1-(7-cyanopyrazolo[1,5-a]pyridin-4-yl)-5-(trifluoromethyl)-1H-pyrazole-4-carboxamide;
(*S)—N-(5-chloro-6-(1-methoxyethyl)pyridin-3-yl)-1-(7-chloropyrazolo[1,5-a]pyridin-4-yl)-5-(trifluoromethyl)-1H-pyrazole-4-carboxamide;
(*R)—N-(5-chloro-6-(1-methoxyethyl)pyridin-3-yl)-1-(7-chloropyrazolo[1,5-a]pyridin-4-yl)-5-(trifluoromethyl)-1H-pyrazole-4-carboxamide;
N-(6-((dimethyl(oxo)-$\lambda^6$-sulfanylidene)amino)-5-(trifluoromethyl)pyridin-3-yl)-1-(8-fluoroimidazo[1,2-a]pyridin-5-yl)-5-(trifluoromethyl)-1H-pyrazole-4-carboxamide;
1-(8-fluoroimidazo[1,2-a]pyridin-5-yl)-N-(6-(S-methylsulfonimidoyl)-5-(trifluoromethyl)pyridin-3-yl)-5-(trifluoromethyl)-1H-pyrazole-4-carboxamide;
N-(6-((dimethyl(oxo)-$\lambda^6$-sulfanylidene)amino)-5-methylpyridin-3-yl)-1-(8-fluoroimidazo[1,2-a]pyridin-5-yl)-5-(trifluoromethyl)-1H-pyrazole-4-carboxamide;
N-(6-((dimethyl(oxo)-$\lambda^6$-sulfanylidene)amino)-5-fluoropyridin-3-yl)-1-(8-fluoroimidazo[1,2-a]pyridin-5-yl)-5-(trifluoromethyl)-1H-pyrazole-4-carboxamide;
N-(5-chloro-6-((dimethyl(oxo)-$\lambda^6$-sulfanylidene)amino)pyridin-3-yl)-1-(8-fluoroimidazo[1,2-a]pyridin-5-yl)-5-(trifluoromethyl)-1H-pyrazole-4-carboxamide;
N-(6-((dimethyl(oxo)-$\lambda^6$-sulfanylidene)amino)-5-methoxypyridin-3-yl)-1-(8-fluoroimidazo[1,2-a]pyridin-5-yl)-5-(trifluoromethyl)-1H-pyrazole-4-carboxamide;
N-(6-((dimethyl(oxo)-$\lambda^6$-sulfanylidene)amino)-5-(trifluoromethyl)pyridin-3-yl)-1-(8-fluoroimidazo[1,2-a]pyridin-5-yl)-5-(trifluoromethyl)-1H-pyrazole-4-carboxamide;
1-(8-fluoroimidazo[1,2-a]pyridin-5-yl)-N-(6-(S-methylsulfonimidoyl)-5-(trifluoromethyl)pyridin-3-yl)-5-(trifluoromethyl)-1H-pyrazole-4-carboxamide;
N-(6-((dimethyl(oxo)-$\lambda^6$-sulfanylidene)amino)-5-methylpyridin-3-yl)-1-(8-fluoroimidazo[1,2-a]pyridin-5-yl)-5-(trifluoromethyl)-1H-pyrazole-4-carboxamide;
N-(6-((dimethyl(oxo)-$\lambda^6$-sulfanylidene)amino)-5-fluoropyridin-3-yl)-1-(8-fluoroimidazo[1,2-a]pyridin-5-yl)-5-(trifluoromethyl)-1H-pyrazole-4-carboxamide; and
N-(5-chloro-6-((dimethyl(oxo)-$\lambda^6$-sulfanylidene)amino)pyridin-3-yl)-1-(8-fluoroimidazo[1,2-a]pyridin-5-yl)-5-(trifluoromethyl)-1H-pyrazole-4-carboxamide;
or a pharmaceutically acceptable salt form thereof.

For use in medicine, salts of compounds of Formula (I) refer to non-toxic "pharmaceutically acceptable salts." Other salts may, however, be useful in the preparation of compounds of Formula (I) or of their pharmaceutically acceptable salt forms thereof. Suitable pharmaceutically acceptable salts of compounds of Formula (I) include acid addition salts that can, for example, be formed by mixing a solution of the compound with a solution of a pharmaceutically acceptable acid such as, hydrochloric acid, sulfuric acid, fumaric acid, maleic acid, succinic acid, acetic acid, benzoic acid, citric acid, tartaric acid, carbonic acid or phosphoric acid. Furthermore, where the compounds of Formula (I) carry an acidic moiety, suitable pharmaceutically acceptable salts thereof may include alkali metal salts such as, sodium or potassium salts; alkaline earth metal salts such as, calcium or magnesium salts; and salts formed with suitable organic ligands such as, quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide, and valerate.

Representative acids and bases that may be used in the preparation of pharmaceutically acceptable salts include acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glutamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine, and zinc hydroxide.

Embodiments of the present invention include prodrugs of compounds of Formula (I). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorph and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula (I).

A person of ordinary skill in the art would recognize that the compounds described herein may exist as tautomers and that other tautomeric arrangements of the structures depicted herein are possible. It is understood that all tautomeric forms are encompassed by a structure where one possible tautomeric arrangement of the groups of the compound is described, even if not specifically indicated.

Where the processes for the preparation of the compounds according to certain embodiments of the invention give rise to mixture of stereoisomers, these isomers may be separated by conventional techniques such as, preparative chromatography. The compounds may be prepared in racemic form, or individual enantiomers may be prepared either by enantiospecific synthesis or by resolution. The compounds may, for example, be resolved into their component enantiomers by standard techniques such as, the formation of diastereomeric pairs by salt formation with an optically active acid such as, (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chomatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of Formula (I) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as $$\% \ (+)-\text{enantiomer} = \frac{(\text{mass} \ (+)-\text{enantiomer})}{(\text{mass} \ (+)-\text{enantiomer}) + (\text{mass} \ (-)-\text{enantiomer})} \times 100.$$

Another embodiment of the present invention is a composition, including a pharmaceutical composition, comprising, consisting of, and consisting essentially of the (−)-enantiomer of a compound of Formula (I) wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as $$\% \ (+)-\text{enantiomer} = \frac{(\text{mass} \ (+)-\text{enantiomer})}{(\text{mass} \ (+)-\text{enantiomer}) + (\text{mass} \ (-)-\text{enantiomer})} \times 100.$$

It is intended that within the scope of the present invention, any one or more element(s), in particular when mentioned in relation to a compound of Formula (I), shall comprise all isotopes and isotopic mixtures of said element(s), either naturally occurring or synthetically produced, either with natural abundance or in an isotopically enriched form. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. Radiolabelled compounds of formula (I) may comprise one or more radioactive isotope(s) selected from the group of 3H, HC, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^2H$, $^3H$, and $^{18}F$.

During any of the processes for preparation of the compounds of the various embodiments of the present invention, it may be necessary and/or desirable to protect sensitive or reactive groups on any of the molecules concerned. This may be achieved by means of conventional protecting groups such as those described in *Protective Groups in Organic Chemistry, Second Edition*, J. F. W. McOmie, Plenum Press, 1973; T. W. Greene & P. G. M. Wuts, *Protective Groups in Organic Synthesis*, John Wiley & Sons, 1991; and T. W. Greene & P. G. M. Wuts, *Protective Groups in Organic Synthesis, Third Edition*, John Wiley & Sons, 1999. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of Formula (I) and at least one pharmaceutically acceptable carrier, pharmaceutically acceptable excipient, and/or pharmaceutically acceptable diluent.

By way of example, in the pharmaceutical compositions of embodiments of the present invention, the compounds of Formula (I) may be admixed with any suitable binder(s), lubricant(s), suspending agent(s), coating agent(s), solubilizing agent(s), and combinations thereof.

Solid oral dosage forms such as, tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, compounds of Formula (I) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a wax or soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example, intracavernosally, intravenously, intramuscularly, subcutaneously, intradermally, or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of Formula (I) as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus, for liquid oral preparations such as, suspensions, syrups, elixirs and solutions, suitable carriers, excipients and diluents include water, glycols, oils, alcohols, flavoring agents, preservatives, stabilizers, coloring agents and the like; for solid oral preparations such as, powders, capsules, and tablets, suitable carriers, excipients and diluents include starches, sugars, diluents, granulating agents, lubricants, binders, disintegrating agents and the like. Solid oral preparations also may be optionally coated with substances such as, sugars, or be enterically coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives such as, solubilizers and preservatives.

A therapeutically effective amount of a compound of Formula (I) or a pharmaceutical composition thereof includes a dose range from about 0.1 mg to about 3000 mg, or any particular amount or range therein, in particular from about 1 mg to about 1000 mg, or any particular amount or range therein, or, more particularly, from about 10 mg to about 500 mg, or any particular amount or range therein, of active ingredient in a regimen of about 1 to about (4×) per day for an average (70 kg) human; although, it is apparent to one skilled in the art that the therapeutically effective amount for a compound of Formula (I) will vary as will the diseases, syndromes, conditions, and disorders being treated.

For oral administration, a pharmaceutical composition is preferably provided in the form of tablets containing about 1.0, about 10, about 50, about 100, about 150, about 200, about 250, and about 500 milligrams of a compound of Formula (I).

An embodiment of the present invention is directed to a pharmaceutical composition for oral administration, comprising a compound of Formula (I) in an amount of from about 25 mg to about 500 mg.

Advantageously, a compound of Formula (I) may be administered in a single daily dose, or the total daily dosage may be administered in divided doses of two, three and (4×) daily.

Optimal dosages of a compound of Formula (I) to be administered may be readily determined and will vary with the particular compound used, the mode of administration, the strength of the preparation, and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

Compounds of Formula (I) may be administered in any of the foregoing compositions and dosage regimens or by means of those compositions and dosage regimens established in the art whenever use of a compound of Formula (I) is required for a subject in need thereof.

In an embodiment, cancers that may benefit from a treatment with MALT1 inhibitors of the present invention include, but are not limited to, lymphomas, leukemias, carcinomas, and sarcomas, e.g. non-Hodgkin's lymphoma, diffuse large B-cell lymphoma (DLBCL), mantle cell lymphoma (MCL), follicular lymphoma (FL), mucosa-associated lymphoid tissue (MALT) lymphoma, marginal zone lymphoma, T-cell lymphoma, Hodgkin's lymphoma, Burkitt's lymphoma, multiple myeloma, chonic lymphocytic leukemia (CLL), lymphoblastic T cell leukemia, chonic myelogenous leukemia (CIVIL), hairy-cell leukemia, acute lymphoblastic T cell leukemia, plasmacytoma, immunoblastic large cell leukemia, megakaryoblastic leukemia, acute megakaryocytic leukemia, promyelocytic leukemia, erythroleukemia, brain (gliomas), glioblastomas, breast cancer, colorectal/colon cancer, prostate cancer, lung cancer including non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head&neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, and GIST (gastrointestinal stromal tumor).

In another embodiment, MALT1 inhibitors of the present invention may be used for the treatment of immunological diseases including, but not limited to, autoimmune and inflammatory disorders, e.g. arthritis, inflammatory bowel disease, gastritis, ankylosing spondylitis, ulcerative colitis, pancreatits, Crohn's disease, celiac disease, multiple sclerosis, systemic lupus erythematosus, lupus nephitis, rheumatic fever, gout, organ or transplact rejection, chonic allograft rejection, acute or chonic graft-versus-host disease, dermatitis including atopic, dermatomyositis, psoriasis, Behcet's diseases, uveitis, myasthenia gravis, Grave's disease, Hashimoto thyroiditis, Sjoergen's syndrome, blistering disorders, antibody-mediated vasculitis syndromes, immune-complex vasculitides, allergic disorders, asthma, bronchitis, chonic obstructive pulmonary disease (COPD), cystic fibrosis, pneumonia, pulmonary diseases including oedema, embolism, fibrosis, sarcoidosis, hypertension and emphysema, silicosis, respiratory failure, acute respiratory distress syndrome, BENTA disease, berylliosis, and polymyositis.

In another embodiment of the present invention, the compounds of the present invention may be employed in combination with one or more other medicinal agents, more particularly with other anti-cancer agents, e.g. chemotherapeutic, anti-proliferative or immunomodulating agents, or with adjuvants in cancer therapy, e.g. immunosuppressive or anti-inflammatory agents.

Possible combinations of the compounds of the present invention may include, but are not limited to, BTK (Bruton's tyrosine kinase) inhibitors such as ibrutinib, SYK inhibitors, PKC inhibitors, PI3K pathway inhibitors, BCL family inhibitors, JAK inhibitors, PIM kinase inhibitors, rituximab or other B cell antigen-binding antibodies, as well as immune cell redirection agents (e.g. blinatumomab or CAR T-cells) and immunomodulatory agents such as daratumumab, anti-PD1 antibodies, and anti-PD-L1 antibodies.

It has been found that the compounds of the present invention inhibit MALT1 activity.
In some embodiments, the inhibition of MALT1 by a provided compound may be useful in treating or preventing, in particular treating, the non-limiting list of cancers described herein.

The invention relates to compounds of Formula (I) or an enantiomer, diastereomer, solvate or pharmaceutically acceptable salt form thereof, for use as a medicament. The invention relates to compounds of Formula (I) or an enantiomer, diastereomer, solvate or pharmaceutically acceptable salt form thereof, for use in the inhibition of MALT1 activity.

The invention relates to compounds of Formula (I) or an enantiomer, diastereomer, solvate or pharmaceutically acceptable salt form thereof, for use in the treatment of diseases mentioned herein.

The invention relates to compounds of Formula (I) or an enantiomer, diastereomer, solvate or pharmaceutically acceptable salt form thereof, for the treatment or prevention, in particular for the treatment, of said diseases.

The invention relates to compounds of Formula (I) or an enantiomer, diastereomer, solvate or pharmaceutically acceptable salt form thereof, for the treatment or prevention, in particular in the treatment, of MALT1 mediated diseases or conditions.

The invention relates to compounds of Formula (I) or an enantiomer, diastereomer, solvate or pharmaceutically acceptable salt form thereof, for the manufacture of a medicament.

The invention relates to compounds of Formula (I) or an enantiomer, diastereomer, solvate or pharmaceutically acceptable salt form thereof, for the manufacture of a medicament for the inhibition of MALT1.

The invention relates to compounds of Formula (I) or an enantiomer, diastereomer, solvate or pharmaceutically acceptable salt form thereof, for the manufacture of a medicament for the treatment or prevention, in particular for the treatment, of any one of the disease conditions mentioned herein.

The invention relates to compounds of Formula (I) or an enantiomer, diastereomer, solvate or pharmaceutically acceptable salt form thereof, for the manufacture of a medicament for the treatment of any one of the disease conditions mentioned herein.

The invention relates to compounds of Formula (I) or an enantiomer, diastereomer, solvate or pharmaceutically acceptable salt form thereof, can be administered to mammals, preferably humans, for the treatment or prevention of any one of the diseases mentioned herein.

In view of the utility of the compounds of Formula (I) or an enantiomer, diastereomer, solvate or pharmaceutically acceptable salt form thereof, there is provided a method of treating warm-blooded animals, including humans, suffering from or a method of preventing warm-blooded animals, including humans, to suffer from any one of the diseases mentioned herein.

General Synthetic Methods

Representative compounds of the present invention can be synthesized in accordance with the general synthetic methods described below and illustrated in the schemes and examples that follow. Since the schemes are an illustration, the invention should not be construed as being limited by the chemical reactions and conditions described in the schemes and examples. Compounds analogous to the target compounds of these examples can be made according to similar routes. The disclosed compounds are useful as pharmaceutical agents as described herein. The various starting materials used in the schemes and examples are commercially available or may be prepared by methods well within the skill of persons versed in the art.

Abbreviations used in the instant specification, particularly the schemes and examples, are as follows:
ACN acetonitrile
AcOH acetic acid
BINAP 2,2'-bis(diphenylphosphino)-1,1'-binaphthalene
Boc tert-butyl carbamate
BuLi butyllithium
Cbz benzyl carbamate
DCM dichloromethane
DMA dimethylacetamide
DME ethylene glycol dimethyl ether
DMF dimethylformamide
DMSO dimethyl sulfoxide
EA ethyl acetate
Et ethyl
Et$_2$O diethyl ether
EtOAc ethyl acetate
EtOH ethyl alcohol
FCC flash column chromatography
h hour(s)
HATU O-(7-azabenzotriazol-1-yl)-N,N,N',N'-tetramethyluronium hexafluorophosphate
HCHO formaldehyde
HCl hydrochloric acid
HPLC high performance liquid chromatography
KCN potassium cyanide
LCMS high pressure liquid choatography with mass spectrometer
LDA lithium diisopropylamide
LiOH lithium hydroxyde
Me methyl MeCN acetonitrile
MeOH methyl alcohol
mg milligram
min minute
NaCN sodium cyanide
NaOH sodium hydroxide
NaOtBu sodium tert-butoxide
NH₄Cl ammonium chloride
Pd/C palladium on charcoal
Pd₂(dba)₃ tris(dibenzylideneacetone)dipalladium
Pd(dppf)Cl₂ [1,1'-bis(diphenylphosphino)ferrocene]dichloropalladium
Pd(OAc)₂ palladium diacetate
Pd(PPh₃)₄ tetrakis(triphenylphosphine)palladium
PPh₃ triphenyl phosphine
p-TsOH para-toluenesulfonic acid
rt or RT room temperature
TBAF tetrabutyl ammonium fluoride
TMSI iodotrimethylsilane
t-Bu tert-butyl
TFA trifluoroacetic acid
TFAA trifluoroacetic anhydride
THF tetrahydrofuran
TLC thin layer chromatography
Xantphos 4,5-Bis(diphenylphosphino)-9,9-dimethylxanthene
Xphos 2-dicyclohexylphosphino-2',4',6'-triisopropylbiphenyl Compounds of Formula (Ia) wherein $R_7$ is hydrogen, may be prepared according to the process outlined in Scheme 1.

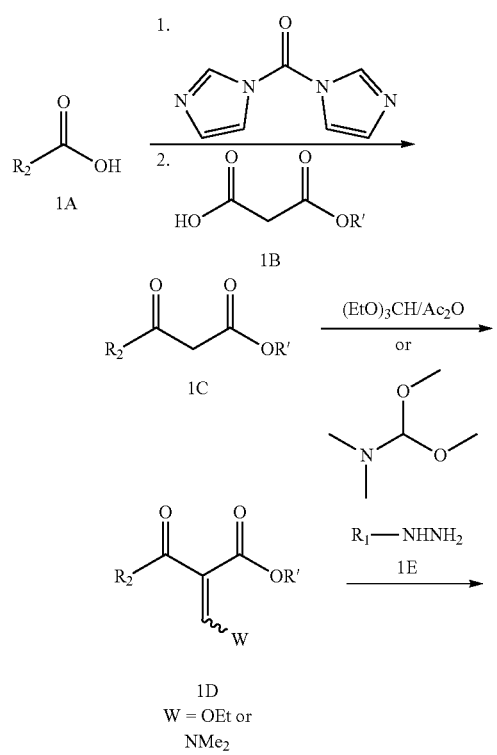

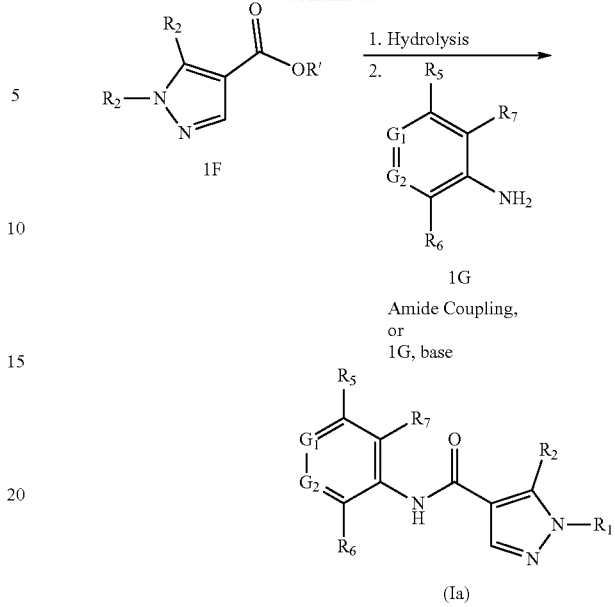

A carboxylic acid of formula (1A) may be treated with carbonyldiimidazole followed by addition of a mono-ester of malonic acid of formula (1B), wherein R' is $C_{1-4}$alkyl, and a base, such as isopropylmagesium chloride, to yield a ketoester of formula (1C). Condensation with triethyl orthoformate in acetic anhydride or with 1,1-dimethoxy-N,N-dimethylmethanamine may yield a 2-ethoxymethylidene-3-oxo ester (or 2-((dimethylamino)methylidene-3-oxo ester) of formula (1D). A compound of formula (1D) may be reacted with a hydrazine of formula (1E) to provide a pyrazole of formula (1F). Hydrolysis of the ester group may be effected via by treatment with aqueous sodium hydroxide in the presence of an alcohol co-solvent, to provide the corresponding carboxylic acid intermediate, which, subsequently, may be converted to a compound of Formula (I) upon amide coupling with a compound of formula (1G). The amide coupling may be carried out, for example, in the presence of phosphorus oxychloride in pyridine to afford the corresponding acid chloride, followed by treatment with a compound of formula (1G), in the presence of a base. In one embodiment, the amide coupling reaction is carried out in the presence of a suitable amide coupling reagent such as HATU, in the presence of a base such as, but not limited to, diisopropylethyl amine.

Alternatively, the pyrazole ester of formula (1F) may be directly converted to a compound of Formula (I) via treatment with a compound of formula (1G) and a base, such as potassium tert-butoxide.

An alternate route to compounds of Formula (Ia) wherein $R_7$ is hydrogen, is illustrated in Scheme 2.

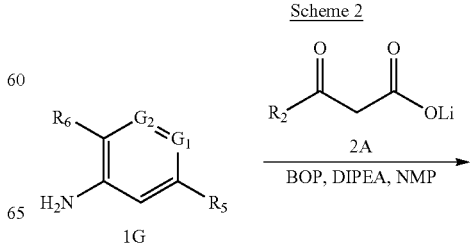

55
-continued

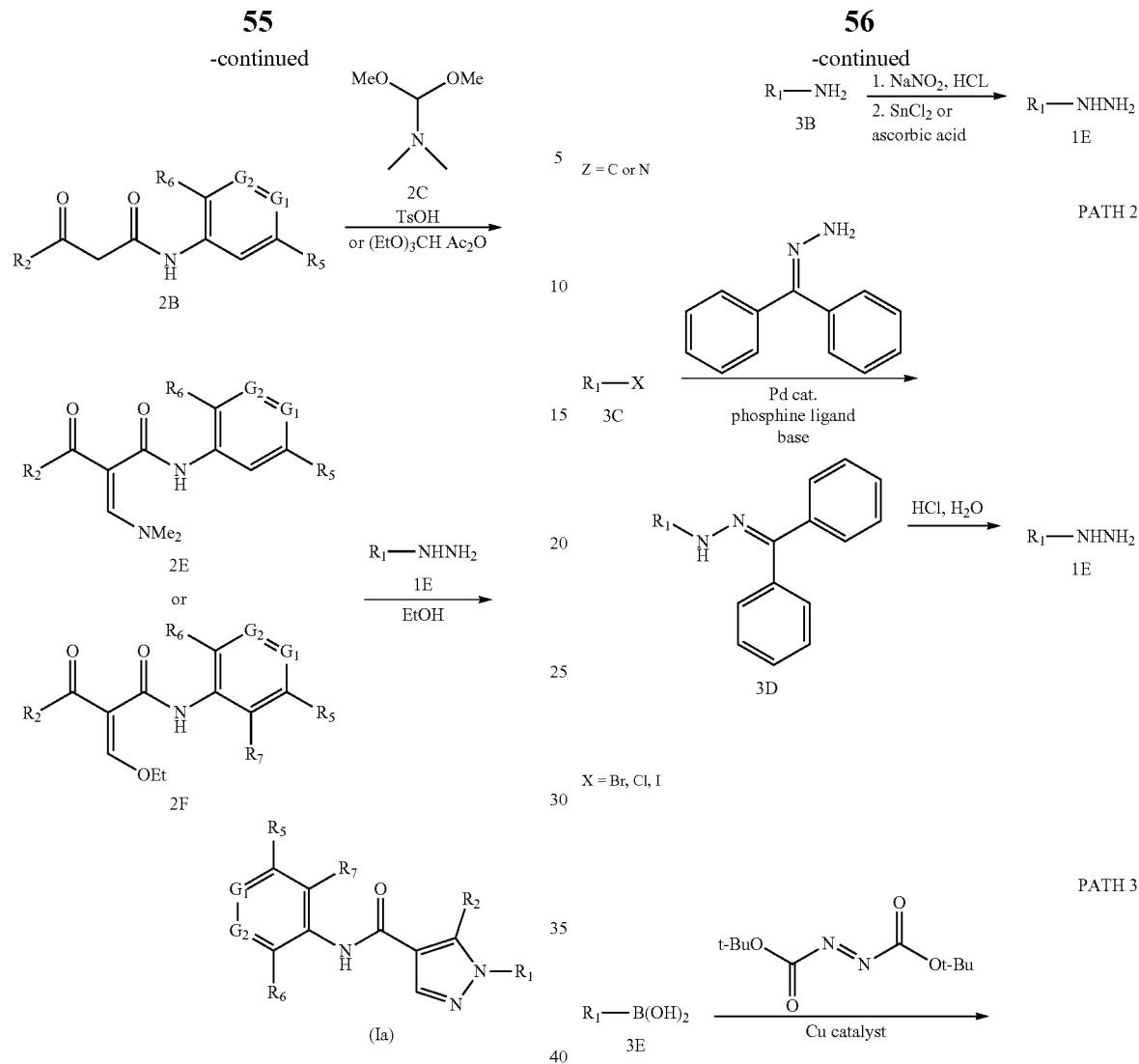

Aniline (1G) may be coupled with a lithium acetoacetate of formula (2A) in the presence of coupling reagent such as BOP, a base such as DIPEA, and a solvent such as NMP, to provide a compound of formula (2B). A compound of formula (2B) may then be reacted with DMF-DMA (2C) in the presence of an acid, such as TsOH, or reacted with triethoxymethane (2D) in AcOH to afford a compound of formula (2E) or (2F), respectively. A compound of formula (2E) or (2F) may then be treated with a hydrazine of formula (1E) to afford a compound of Formula (I).

Scheme 3 illustrates the preparation of certain hydrazine intermediates of formula (1E), useful for the preparation of compounds of Formula (I) of the present invention.

Scheme 3

56
-continued

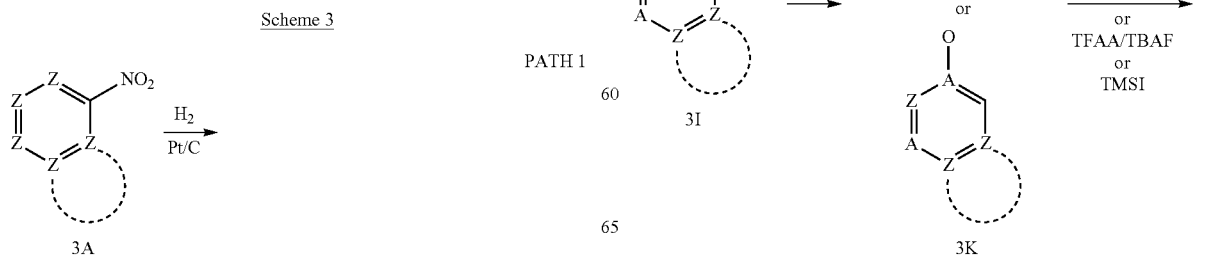

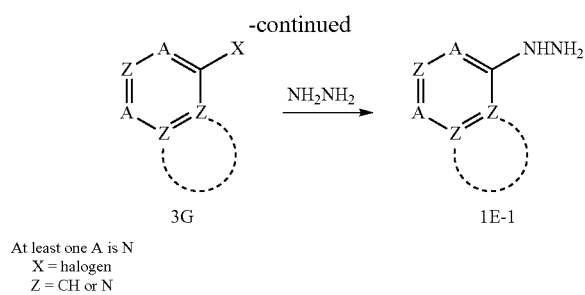

3G

At least one A is N
X = halogen
Z = CH or N 1E-1

PATH 5

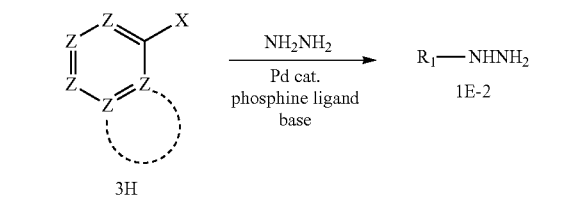

3H

X = Cl, Br, I
Z = C or N 1E-2

A heteroaryl amine of formula (3B) may be converted to a heteroaryl diazonium salt via treatment with sodium nitrite under acidic conditions. This intermediate may be reduced, using a reductant such as tin (II) chloride or ascorbic acid, to form the hydrazine of formula (1E). For heteroaryl amines of formula (3B) that are not commercially available, they may be accessed by reduction of the heteronitroarene (3A) using hydrogen and Pt/C or other conventional nitro-reducing conditions (path one).

$R_1$-substituted chlorides, bromides, and iodides may undergo a palladium catalyzed Buchwald Hartwig coupling with benzophenone hydrazine, in the presence of a ligand, such as Xantphos, and a base, such as sodium tert-butoxide, to form a hydrazine of formula (3D). Acidic hydrolysis may afford the hydrazine of formula (1E) (path two).

$R_1$-substituted boronic acids may also serve as a precursor to compounds of formula (1E) by the route shown in path three. A boronic acid of formula (3E) may undergo a $Cu^{2+}$-catalyzed (such as $Cu(OAc)_2$, TEA in $CH_2Cl_2$) addition to di-tert-butylazodicarboxylate to afford an intermediate of formula (3F), which may be deprotected under acidic conditions to yield the compound of formula (1E). Heteroaryl hydrazines of formula (1E-1), having a nitrogen atom in the ortho- or para-position with respect to the hydrazine functionality, may be prepared via direct displacement of a halogen with hydrazine or hydrazine hydrate. (Hetero) haloarenes of formula (3G) that are not commercially available may be prepared from their corresponding (hetero)arenes (3I), with an oxidant such as mCPBA, to form the N-oxide (3J) (or (3K)) that may then be converted to (hetero) haloarene 3G via treatment with $POCl_3$ and DMF, $POBr_3$/DMF, TFAA/TBAF, or TMSI (path four). Alternatively, halogenated (hetero)arenes of formula (3H) may undergo palladium-catalyzed cross-coupling with hydrazine to directly furnish intermediate (1E-2) (path five).

Scheme 4 illustrates multiple pathways available for the synthesis of intermediate (1G-1), wherein $G_1$ is $C(R_4)$.

Scheme 4

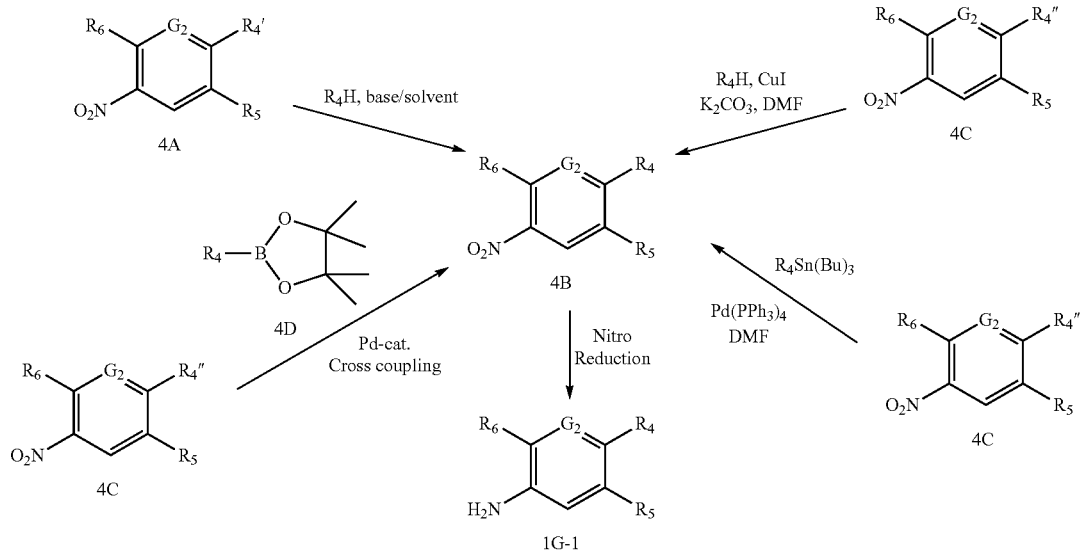

$R_4'$ = F, Cl, Br
$R_4''$ = Cl, Br, I

Compound (B-1) may be reacted with a compound of formula R$_4$H in the presence of a base, such as Cs$_2$CO$_3$, in a solvent, such as DMF, to yield a compound of formula (4B). Alternatively, a compound of formula (4C) may be treated with a crossing coupling reagent, such as a boron reagent of formula (4D) or a tin reagent of formula R$_4$Sn (Bu)$_3$; in the presence of a palladium catalyst, including but not limited to, Pd(dppf)Cl$_2$ or Pd(PPh$_3$)$_4$; in a suitable solvent or solvent system such as DMF, dioxane/water, or the like; to produce a compound of formula (4B). Another suitable pathway includes the reaction of a compound of formula (4C) with a compound of formula R$_4$H, in the presence of a coupling reagent such as CuI, with a base such as Cs$_2$CO$_3$, and in a solvent such as DMF, to afford a compound of formula (4B). A compound of formula (4B) may be reduced to a compound of formula (1G-1) using a reducing agent such as Zn or Fe in the presence of NH$_4$Cl, in a solvent such as MeOH.

Scheme 5 illustrates the preparation of certain compounds of Formula (I) wherein R$_6$ is other than hydrogen.

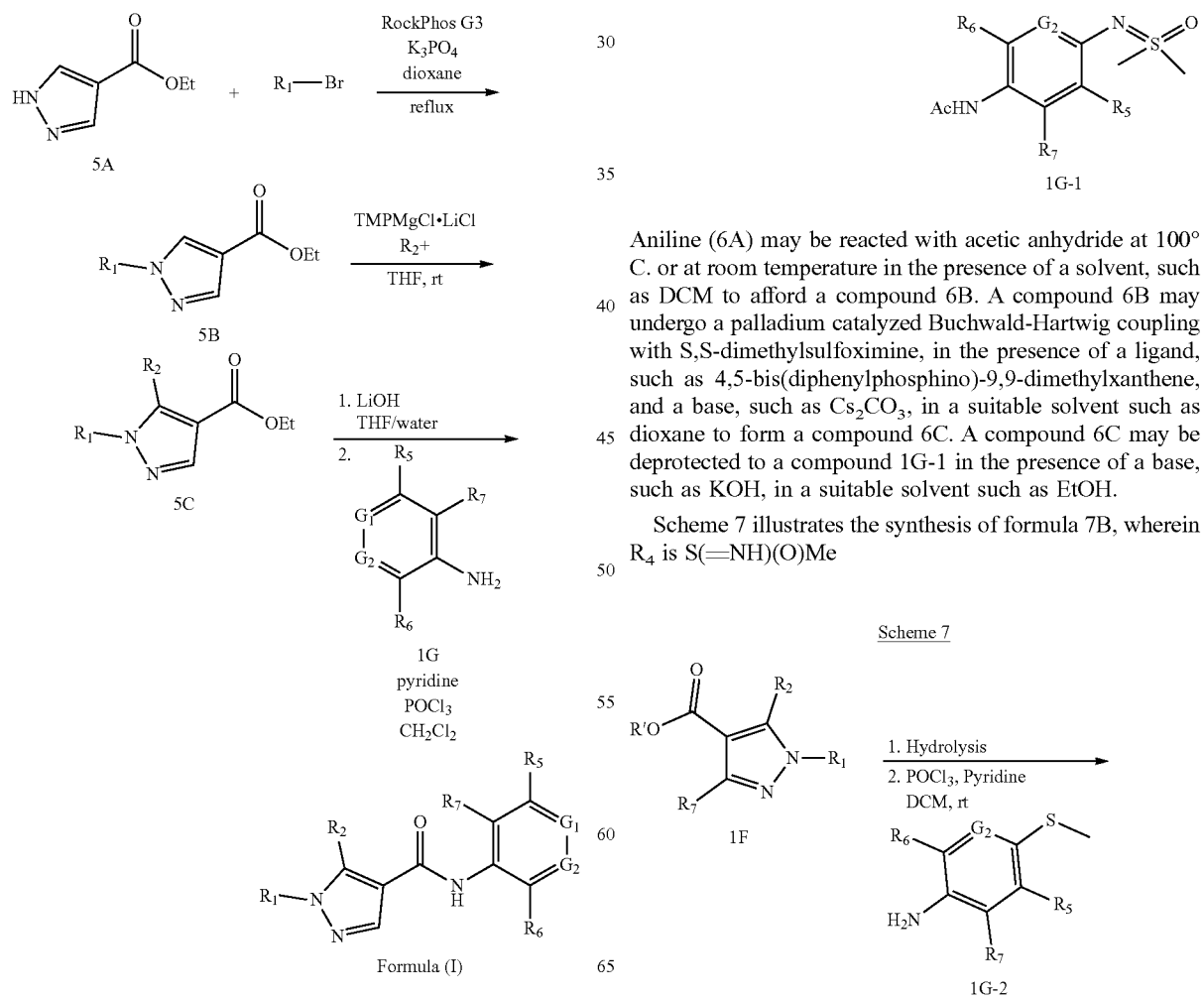

Scheme 5

Formula (I)

Scheme 6 illustrates the synthesis of intermediate (1G-1), wherein G$_1$ is C(R$_4$) and R$_4$=(CH$_3$)$_2$SONH, X is Cl, Br, I.

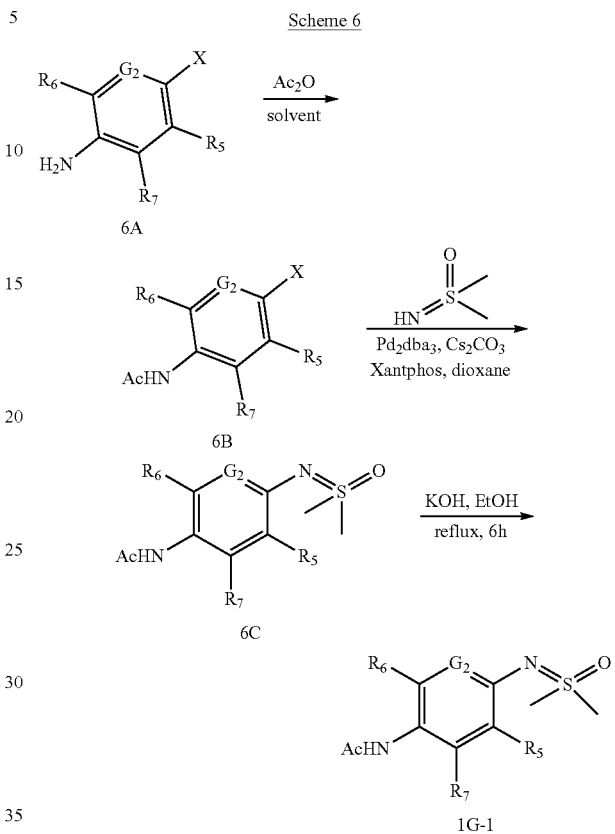

Scheme 6

Aniline (6A) may be reacted with acetic anhydride at 100° C. or at room temperature in the presence of a solvent, such as DCM to afford a compound 6B. A compound 6B may undergo a palladium catalyzed Buchwald-Hartwig coupling with S,S-dimethylsulfoximine, in the presence of a ligand, such as 4,5-bis(diphenylphosphino)-9,9-dimethylxanthene, and a base, such as Cs$_2$CO$_3$, in a suitable solvent such as dioxane to form a compound 6C. A compound 6C may be deprotected to a compound 1G-1 in the presence of a base, such as KOH, in a suitable solvent such as EtOH.

Scheme 7 illustrates the synthesis of formula 7B, wherein R$_4$ is S(=NH)(O)Me

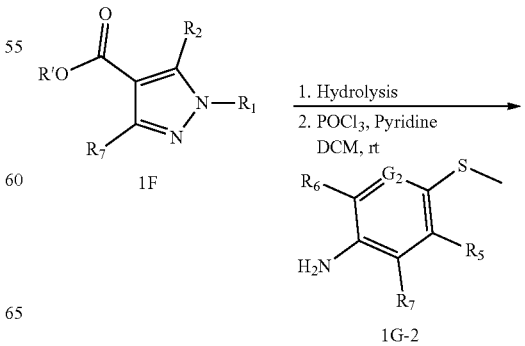

Scheme 7

-continued

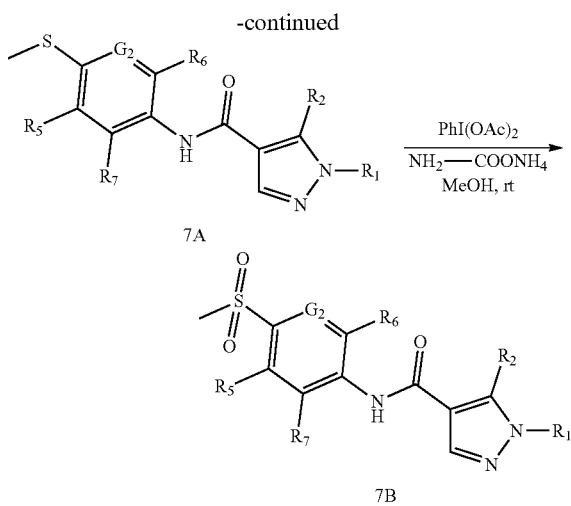

$R_4$ = SMe

Hydrolysis of a compound 1F may be effected via by treatment with aqueous sodium hydroxide in the presence of an alcohol co-solvent, to provide the corresponding carboxylic acid intermediate, which, subsequently, may be converted to a compound 7A upon amide coupling with a compound of formula (1G-2). The amide coupling may be carried out, for example, in the presence of phosphorus oxychloride in pyridine to afford the corresponding acid chloride, followed by treatment with a compound of formula (1G-2), in the presence of a base such as pyridine. A compound 7A may be reacted with ammonium carbamate in the presence of an oxidant, such as PhI(OAc)$_2$, in a suitable solvent such as MeOH to provide a compound 7B.

SPECIFIC EXAMPLES

In the following Examples, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

5-(4-((5-chloro-6-(2H-1,2,3-triazol-2-yl)pyridin-3-yl)carbamoyl)-5-(trifluoromethyl)-1H-pyrazol-1-yl)imidazo[1,2-a]pyridine-8-carboxamide, cpd 1

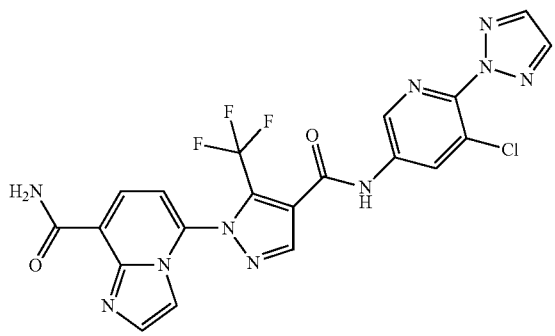 [SMILES: NC(=O)c1ccc(-n2ncc(C(=O)Nc3cnc(-n4nccn4)c(Cl)c3)c2C(F)(F)F)n2ccnc12]

A. 2-amino-6-chloronicotinamide, cpd 1a

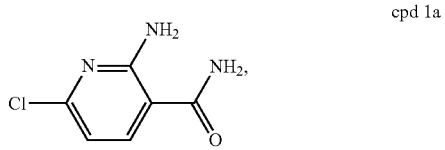 [SMILES: NC(=O)c1ccc(Cl)nc1N]

HATU (1.65 g, 4.35 mmol) was added to a solution of 2-amino-6-chloronicotinic acid (500 mg, 2.90 mmol), ammonium hydrochloride (155 mg, 2.90 mmol), DIEA (1.87 g, 14.49 mmol) in methylene chloride (8 mL). The mixture was stirred at rt for 2 h. The reaction mixture was purified by column chromatography over silica gel (eluent: petroleum ether/ethyl acetate 1:0 to ethyl acetate). The desired fractions were collected and the solvent was concentrated under reduced pressure to give the title compound as a white solid (450 mg, 90.5%).

B. 5-chloroimidazo[1,2-a]pyridine-8-carboxamide, cpd 1b

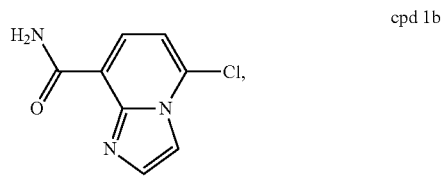 [SMILES: NC(=O)c1ccc(Cl)n2ccnc12]

2-Bromo-1,1-diethoxyethane (1.03 g, 5.25 mmol) was added to a solution of 2-amino-6-chloronicotinamide (540 mg, 2.62 mmol) in HBr (2 mL) and ethanol (20 mL). The mixture was stirred at rt for 2 h. The solvent was concentrated under reduced pressure. Water (20 mL) was added to the mixture. The mixture was extracted with EtOAc (30 mL×3). The combined organic layers were washed with brine, dried with anhydrous MgSO$_4$, then filtered. The filtrates were concentrated under reduced pressure to afford the title compound (460 mg, 89.7% yield).

C. 5-hydrazinylimidazo[1,2-a]pyridine-8-carboxamide, cpd 1c

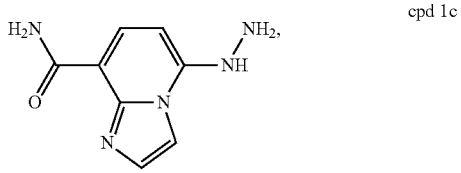 [SMILES: NNc1ccc(C(N)=O)c2nccn12]

Hydrazine (672 mg, 20.96 mmol) was added to a solution of 5-chloroimidazo[1,2-a]pyridine-8-carboxamide (410 mg, 2.10 mmol) in ethanol (20 mL). The reaction mixture was stirred at 80° C. for 16 h. The solvent was concentrated under reduced pressure to afford a crude product, which was used for the next step without further purification.

E. ethyl 1-(8-carbamoylimidazo[1,2-a]pyridin-5-yl)-5-(trifluoromethyl)-1H-pyrazole-4-carboxylate, cpd 1d

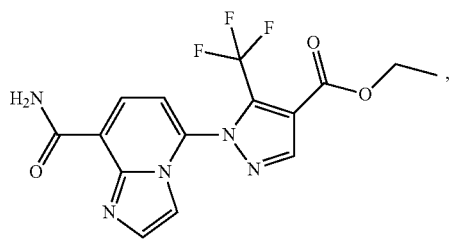

cpd 1d

Ethyl 2-(ethoxymethylene)-4,4,4-trifluoro-3-oxobutanoate (1.51 g, 6.28 mmol) was added to a solution of 5-hydrazinylimidazo[1,2-a]pyridine-8-carboxamide (600 mg, 3.14 mmol) in ethanol (20 mL). The mixture was reacted at 80° C. for 3 h. The solvent was concentrated under reduced pressure to afford a crude product as a brown oil. The crude product was purified by column chromatography over silica gel (petroleum ether to ethyl acetate). The desired fractions were collected and the solvent was concentrated under reduced pressure to afford the product as a yellow solid (180 mg, 14%). LC-MS: (ES, m/z): [M+1]$^+$ 368.0.

F. 1-(8-carbamoylimidazo[1,2-a]pyridin-5-yl)-5-(trifluoromethyl)-1H-pyrazole-4-carboxylic Acid, cpd 1e

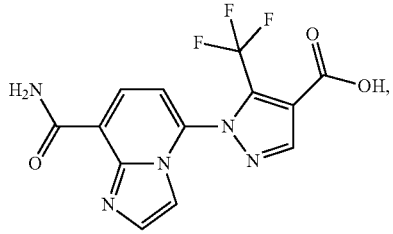

cpd 1e

Lithium hydroxide (9.78 mg, 0.41 mmol) was added to a solution of ethyl 1-(8-carbamoylimidazo[1,2-a]pyridin-5-yl)-5-(trifluoromethyl)-1H-pyrazole-4-carboxylate (100 mg, 0.27 mmol) in THF/water (4 mL, 1:1). The mixture was reacted at room temperature for 72 hours. The solvent was concentrated under reduced pressure and water (10 mL) was added to the mixture. The mixture was made acidic (pH 5) by the addition of 1M hydrochloric acid, then extracted with ethyl acetate (20 mL×3). The combined organic layers were washed with brine, dried over anhydrous MgSO$_4$, filtered, and the filtrates were concentrated under reduced pressure to afford the title compound as a brown oil (90 mg, 69.6%). LC-MS: (ES, m/z): [M+1]$^+$ 340.0

G. 3-Chloro-5-nitro-2-(2H-1,2,3-triazol-2-yl)pyridine, 1g

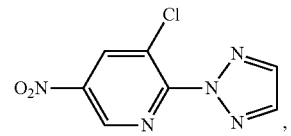

1g

A mixture of 2,3-dichloro-5-nitropyridine (50 g, 259.08 mmol), 1H-1,2,3-triazole (19.683 g, 284.99 mmol), potassium carbonate (46.549 g, 336.81 mmol) and CH$_3$CN (200 mL) was heated to 40° C. and stirred overnight. Ethyl acetate (500 mL) was added. The mixture was washed with water (500 mL×2) and brine (500 mL), dried over anhydrous Na$_2$SO$_4$, filtered, and concentrated to dryness under reduced pressure. The residue was triturated with DCM (100 mL), filtered, and the solid was collected to afford compound 1g (40 g, 68%) as an off-white solid. LC-MS: (ES, m/z): [M+1]$^+$ 225.9. $^1$H NMR (400 MHz, DMSO-d$_6$) δ ppm 9.40 (d, J=2.0 Hz, 1H), 9.15 (d, J=2.0 Hz, 1H), 8.33 (s, 2H).

H. 5-Chloro-6-(2H-1,2,3-triazol-2-yl)pyridin-3-amine, 1h

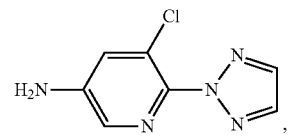

1h

3-Chloro-5-nitro-2-(2H-1,2,3-triazol-2-yl)pyridine (20 g, 88.656 mmol), MeOH (500 mL) and Pt/C (2 g, 5%, 0.513 mmol) were added to a 1000 mL hydrogenation bottle. The resultant mixture was stirred under a H$_2$ atmosphere (30 psi) at 25° C. for 20 h. The suspension was filtered though a pad of diatomaceous earth and the filter cake was washed with ethyl acetate (100 mL). The filtrate was concentrated to dryness under reduced pressure to afford a crude product, which was purified by preparative reverse phase HPLC (0% to 50% (v/v) CH$_3$CN and water with 0.05% NH$_3$), followed by lyophilization to dryness to afford compound 1h (10.4 g, 60%) as an off-white solid. LC-MS: (ES, m/z): [M+1]$^+$ 196.1; $^1$H NMR (400 MHz, DMSO-d$_6$) δ ppm 8.05 (s, 2H), 7.83 (d, J=2.0 Hz, 1H), 7.21 (d, J=2.4 Hz, 1H), 6.19 (s, 2H).

I. 5-(4-((5-Chloro-6-(2H-1,2,3-triazol-2-yl)pyridin-3-yl)carbamoyl)-5-(trifluoromethyl)-1H-pyrazol-1-yl)imidazo[1,2-a]pyridine-8-carboxamide, cpd 1

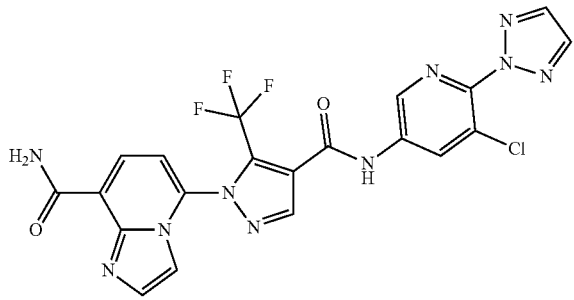 [SMILES: NC(=O)c1ccc(-n2ncc(C(=O)Nc3cnc(-n4nccn4)c(Cl)c3)c2C(F)(F)F)n2ccnc12]

POCl$_3$ (29.08 mg, 0.19 mmol) was added to a mixture of 1-(8-carbamoylimidazo[1,2-a]pyridin-5-yl)-5-(trifluoromethyl)-1H-pyrazole-4-carboxylic acid (90 mg, 0.19 mmol), 5-chloro-6-(2H-1,2,3-triazol-2-yl)pyridin-3-amine (44.51 mg, 0.23 mmol) and pyridine (30.0 mg, 0.38 mmol) in methylene chloride (6 mL). The reaction mixture was stirred at 20° C. for 1 h. Sat. NaHCO$_3$ solution (20 mL) was added to the mixture. The mixture was extracted with CH$_2$Cl$_2$ (20 mL×2). The combined organic layers were washed with brine. The organic layer was concentrated under reduced pressure to afford crude product as a brown oil. The crude product was purified by preparative high-performance liquid chromatography: Column: Phenomenex Gemini 150*25 mm*10 um; Condition: A: water (0.05% ammonia hydroxide v/v); B: MeCN at the beginning: A (85%) and B (15%); at the end: A (55%) and B (45%). Gradient Time(min) 12; 100% B Hold Time(min) 2.2; Flow Rate(ml/min) 25. The pure fractions were collected and the organic solvent was concentrated under reduced pressure. The aqueous layer was lyophilized to dryness to give the product (30 mg, 30.5%) as a white solid. $^1$H NMR (400 MHz, DMSO-d6) δ ppm 7.61-7.67 (2H, m), 7.88 (1H, d, J=1.25 Hz), 8.21 (2H, s), 8.23 (1H, s), 8.27 (1H, br s), 8.69 (1H, d, J=2.26 Hz), 8.76 (1H, s), 8.86 (1H, d, J=2.01 Hz), 9.43 (1H, br s), 11.32 (1H, br s). LC-MS: (ES, m/z): [M+1]$^+$ 517.1

Following the procedures described in Example 1 and selecting and substituting the appropriate reagents, starting materials, and purification methods, and adjusting reaction temperatures, times and other variables or parameters, as needed or desirable, as would be readily recognized by those skilled in the art, the following compounds (2-7) were prepared.

Example 2

N-(5-chloro-6-(2H-1,2,3-triazol-2-yl)pyridin-3-yl)-1-(8-cyanoimidazo[1,2-a]pyridin-5-yl)-5-(trifluoromethyl)-1H-pyrazole-4-carboxamide, cpd 2

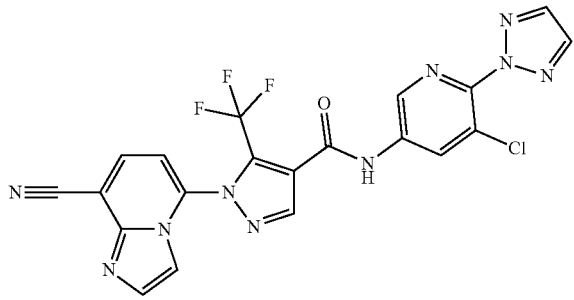 [SMILES: N#Cc1ccc(-n2ncc(C(=O)Nc3cnc(-n4nccn4)c(Cl)c3)c2C(F)(F)F)n2ccnc12]

$^1$H NMR (400 MHz, DMSO-d$_6$) δ ppm 7.70 (1H, d, J=7.53 Hz), 7.74 (1H, d, J=1.00 Hz), 7.92 (1H, s), 8.20 (2H, s), 8.29 (1H, d, J=7.53 Hz), 8.68 (1H, d, J=2.26 Hz), 8.78 (1H, s), 8.86 (1H, d, J=2.26 Hz), 11.32 (1H, br s). LC-MS: (ES, m/z): [M+1]$^+$ 499.1

Example 3

N-(5-chloro-6-(1H-pyrazol-1-yl)pyridin-3-yl)-1-(8-fluoroimidazo[1,2-a]pyridin-5-yl)-5-(trifluoromethyl)-1H-pyrazole-4-carboxamide, cpd 3

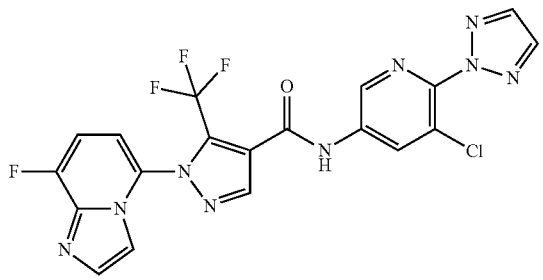 [SMILES: O=C(Nc1cnc(-n2nccn2)c(Cl)c1)c1cnn(-c2ccc(F)c3nccn23)c1C(F)(F)F]

$^1$H NMR (400 MHz, DMSO-d6) δ ppm 6.50-6.61 (m, 1H), 7.42-7.52 (m, 2H), 7.53-7.56 (m, 1H), 7.80 (dd, J=9.0, 1.0 Hz, 2H), 8.25 (d, J=2.4 Hz, 1H), 8.58 (d, J=2.2 Hz, 1H), 8.70 (s, 1H), 8.78 (d, J=2.2 Hz, 1H), 10.78 (dt, J=9.8, 1.8 Hz, 1H). LC-MS: (ES, m/z): [M+1]$^+$ 490.9

Example 4

N-(6-(2H-1,2,3-triazol-2-yl)-5-(trifluoromethyl)pyridin-3-yl)-1-(8-fluoroimidazo[1,2-a]pyridin-5-yl)-5-(trifluoromethyl)-1H-pyrazole-4-carboxamide, cpd 4

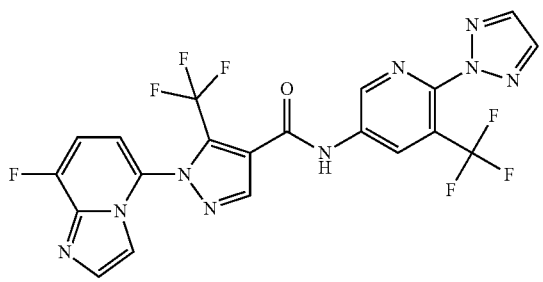 [SMILES: O=C(Nc1cnc(-n2nccn2)c(C(F)(F)F)c1)c1cnn(-c2ccc(F)c3nccn23)c1C(F)(F)F]

$^1$H NMR (400 MHz, DMSO-d6) δ ppm 7.41-7.47 (1H, m), 7.48-7.52 (1H, m), 7.54 (1H, d, J=2.20 Hz), 7.77 (1H, s), 8.20 (2H, s), 8.72 (1H, s), 8.88 (1H, d, J=2.20 Hz), 9.17 (1H, d, J=1.96 Hz), 11.40 (1H, br s). LC-MS: (ES, m/z): [M+1]$^+$ 526.1

Example 5

1-(8-fluoroimidazo[1,2-a]pyridin-5-yl)-N-(6-(methylsulfonyl)-5-(trifluoromethyl)pyridin-3-yl)-5-(trifluoromethyl)-1H-pyrazole-4-carboxamide, cpd 5

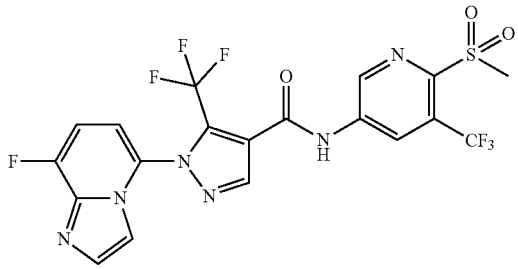 [SMILES: CS(=O)(=O)c1ncc(NC(=O)c2cnn(-c3ccc(F)c4nccn34)c2C(F)(F)F)cc1C(F)(F)F]

$^1$H NMR (400 MHz, DMSO-d6) δ ppm 3.47 (3H, s), 7.43-7.49 (1H, m), 7.50-7.54 (1H, m), 7.54-7.57 (1H, m), 7.79 (1H, d, J=1.25 Hz), 8.71 (1H, s), 8.83 (1H, d, J=2.01 Hz), 9.24 (1H, d, J=2.01 Hz), 11.49 (1H, br s). LC-MS: (ES, m/z): [M+1]$^+$ 537.1

Example 6

N-(5-chloro-6-(oxazol-2-yl)pyridin-3-yl)-1-(8-fluoroimidazo[1,2-a]pyridin-5-yl)-5-(trifluoromethyl)-1H-pyrazole-4-carboxamide, cpd 6

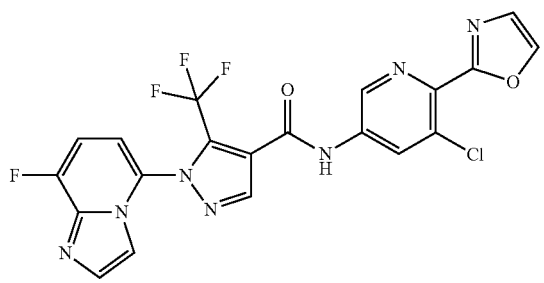 [SMILES: O=C(Nc1cnc(-c2ncco2)c(Cl)c1)c1cnn(-c2ccc(F)c3nccn23)c1C(F)(F)F]

$^1$H NMR (400 MHz, DMSO-d6) δ ppm 7.41-7.56 (m, 4H), 7.78 (s, 1H), 8.34 (s, 1H), 8.56 (d, J=1.7 Hz, 1H), 8.70 (s, 1H), 8.94 (d, J=1.7 Hz, 1H), 11.24 (br s, 1H). LC-MS: (ES, m/z): [M+1]$^+$ 492.1

Example 7

N-(5-chloro-6-(2H-1,2,3-triazol-2-yl)pyridin-3-yl)-1-(8-methylimidazo[1,2-a]pyridin-5-yl)-5-(trifluoromethyl)-1H-pyrazole-4-carboxamide, cpd 7

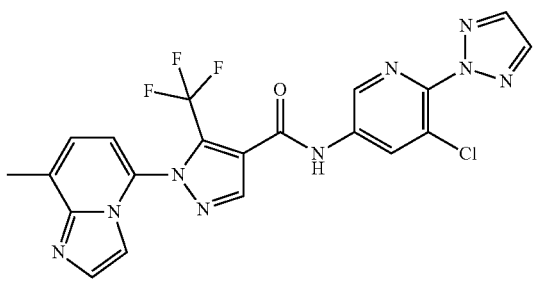 [SMILES: Cc1ccc(-n2ncc(C(=O)Nc3cnc(-n4nccn4)c(Cl)c3)c2C(F)(F)F)n2ccnc12]

$^1$H NMR (400 MHz, DMSO-d6) δ ppm 2.59 (3H, s), 7.30 (2H, d, J=3.67 Hz), 7.32 (1H, s), 7.66 (1H, s), 8.16 (2H, s), 8.64 (1H, d, J=2.20 Hz), 8.66 (1H, s), 8.82 (1H, d, J=2.20 Hz), 11.30 (1H, br s). LC-MS: (ES, m/z): [M+1]$^+$ 488.1

Example 8

N-(5-chloro-6-(2H-1,2,3-triazol-2-yl)pyridin-3-yl)-1-(8-fluoroimidazo[1,2-a]pyridin-5-yl)-5-(methylsulfonyl)-1H-pyrazole-4-carboxamide, cpd 8

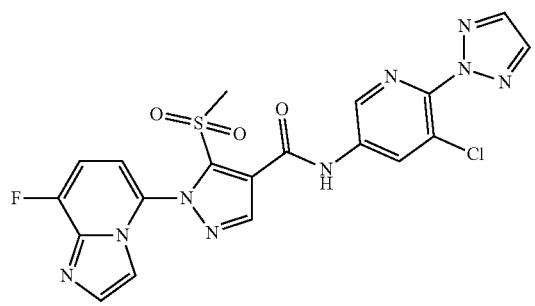 [SMILES: CS(=O)(=O)c1c(C(=O)Nc2cnc(-n3nccn3)c(Cl)c2)cnn1-c1ccc(F)c2nccn12]

A. ethyl 5-amino-1-(6-bromo-5-fluoropyridin-2-yl)-1H-pyrazole-4-carboxylate, cpd 8a

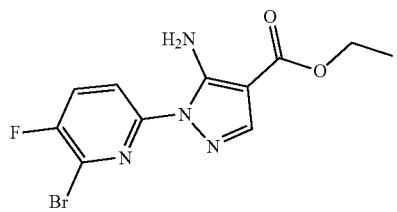

cpd 8a

A solution consisting of 2-bromo-3-fluoro-6-hydrazinylpyridine (3.8 g, 18.45 mmol) and ethyl 2-cyano-3-ethoxyacrylate (4.68 g, 27.67 mmol) in ethanol (50 mL) was stirred at 80° C. for 3 h. The resultant solution was cooled to room temperature and concentrated to dryness under reduced pressure to afford the crude title product. The crude product was purified by flash column chromatography over silica gel (eluent: petroleum ether/ethyl acetate from 100/0 to 30/70). The eluent was collected and the solvent was concentrated under reduced pressure to give the product as a white solid (1.7 g, 25.3%). $^1$H NMR (400 MHz, DMSO-d6) δ ppm 1.14-1.24 (m, 3H), 4.10 (q, J=7.09 Hz, 2H), 6.53-6.72 (m, 1H), 7.58-7.74 (m, 1H), 7.77-8.04 (m, 1H), 9.27-9.56 (m, 1H), 10.11-10.43 (m, 1H). LC-MS: (ES, m/z): [M+1]$^+$ 331.0

B. ethyl 5-amino-1-(6-((tert-butoxycarbonyl)amino)-5-fluoropyridin-2-yl)-1H-pyrazole-4-carboxylate, cpd 8b

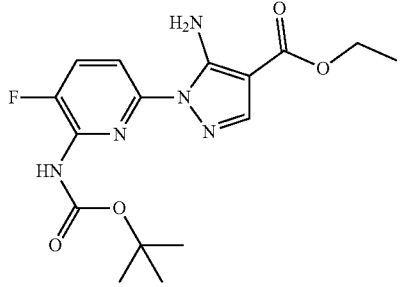

cpd 8b

Palladium diacetate (122.8 mg, 0.55 mmol) and (9,9-dimethyl-9H-xanthene-4,5-diyl)bis(diphenylphosphane) (158.2 mg, 0.27 mmol) were added to a solution of ethyl 5-amino-1-(6-bromo-5-fluoropyridin-2-yl)-1H-pyrazole-4-carboxylate (0.90 g, 2.74 mmol), tert-butyl carbamate (384.4 mg, 3.28 mmol) and cesium carbonate (1782 mg, 5.47 mmol) in dioxane (10 mL) under $N_2$ bubbling. The reaction was stirred at 100° C. for 4 h. The mixture was filtered and the filtrate was concentrated to give a crude product. The crude product was purified by flash column chromatography over silica gel (eluent: petroleum ether/ethyl acetate from 100/0 to 30/70). The eluent was collected and the solvent was concentrated under reduced pressure to afford the product as a yellow solid (0.6 g, 60% yield). $^1$H NMR (400 MHz, CHLOROFORM-d) δ ppm 1.28-1.38 (m, 3H), 1.53 (s, 9H), 4.19-4.30 (m, 2H), 4.39 (br s, 1H), 7.15 (br s, 1H), 7.24 (s, 1H), 7.46 (s, 1H), 7.47 (d, J=4.65 Hz, 1H), 7.72 (s, 1H). LC-MS: (ES, m/z): [M+1]$^+$ 336.2

C. ethyl 5-amino-1-(6-amino-5-fluoropyridin-2-yl)-1H-pyrazole-4-carboxylate, cpd 8c

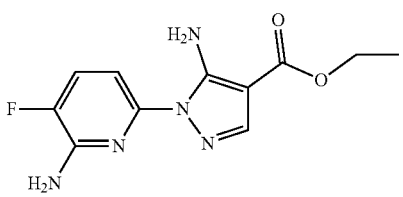

cpd 8c

Ethyl 5-amino-1-(6-((tert-butoxycarbonyl)amino)-5-fluoropyridin-2-yl)-1H-pyrazole-4-carboxylate (600 mg, 1.43 mmol) and HCl in MeOH (15 mL) were stirred at 30° C. for 1 h. The mixture was concentrated to dryness to give the title product as an orange gum (450 mg, 86.4%) which was used in the next step without purification. LC-MS: (ES, m/z): [M+1]$^+$ 266.1

D. ethyl 5-amino-1-(8-fluoroimidazo[1,2-a]pyridin-5-yl)-1H-pyrazole-4-carboxylate, cpd 8d

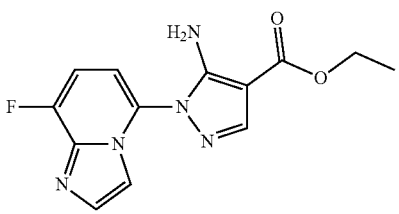

cpd 8d

Ethyl 5-amino-1-(6-amino-5-fluoropyridin-2-yl)-1H-pyrazole-4-carboxylate (450 mg, 1.70 mmol) was dissolved in ethanol (10 mL) under $N_2$. 2-Bromo-1,1-diethoxyethane (668.7 mg, 3.39 mmol) was added to the suspension followed by HBr (1 mL). The resulting mixture was then refluxed for 18 h and cooled down to room temperature. The solvent was removed under reduced pressure. Aqueous 10% $NaHCO_3$ solution (10 mL) was added to the mixture and the mixture was extracted with EtOAc (50 mL×2). The combined organic layers were concentrated to dryness under reduced pressure to afford the crude title product. The crude product was purified by chromatography on silica gel (eluent: petroleum ether/ethyl acetate from 100/0 to 50/50). The pure fractions were collected and the solvent was concentrated under reduced pressure to give the product as a light green solid (190 mg, 38.7% yield). LC-MS: (ES, m/z): [M+1]$^+$ 290.1

E. ethyl 1-(8-fluoroimidazo[1,2-a]pyridin-5-yl)-5-(methylthio)-1H-pyrazole-4-carboxylate, cpd 8e

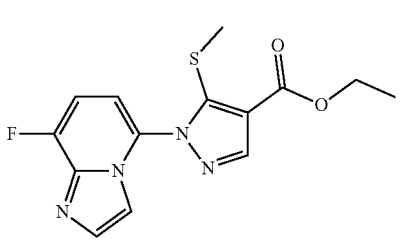

cpd 8e iso-pentyl nitrite (178.2 mg, 1.52 mmol) was added dropwise to a solution of ethyl 5-amino-1-(8-fluoroimidazo[1,2-a]pyridin-5-yl)-1H-pyrazole-4-carboxylate (220 mg, 0.76 mmol) and 1,2-dimethyldisulfane (143.3 mg, 1.52 mmol) in chloroform (10 mL) under $N_2$ at 0° C. The reaction mixture was stirred at rt for 36 h. The mixture was followed by the addition of water (40 mL), and the mixture was extracted with dichloromethane (50 mL×3). The combined organic layers were dried over $MgSO_4$ and concentrated under reduced pressure to give a crude product. The crude product was purified by column chromatography over silica gel (eluent: petroleum ether/ethyl acetate=100:0 to 50:50) to afford the title compound as a yellow oil (160 mg, 60.8% yield). LC-MS: (ES, m/z): [M+1]$^+$ 321.2

F. ethyl 1-(8-fluoroimidazo[1,2-a]pyridin-5-yl)-5-(methylsulfonyl)-1H-pyrazole-4-carboxylate, cpd 8f

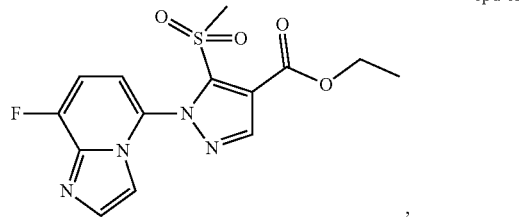

To a solution of ethyl 1-(8-fluoroimidazo[1,2-a]pyridin-5-yl)-5-(methylthio)-1H-pyrazole-4-carboxylate (220 mg, 0.64 mmol) in methylene dichloride (20 mL) was added m-CPBA (331 mg, 1.92 mmol). The mixture was stirred at rt overnight. The reaction mixture was washed with a saturated aqueous solution of sodium bisulfite (20 mL×3) to destroy excess oxidant. The mixture was then twice washed with saturated aqueous sodium hydrogen carbonate (20 mL), and brine (30 mL). The combined organic layer was dried over MgSO$_4$ and concentrated under reduced pressure to give a crude product. The crude product was purified by column chromatography over silica gel (petroleum ether/ethyl acetate=100:0 to 50:50) to afford the title compound as a yellow solid (80 mg, 35.6% yield). $^1$H NMR (400 MHz, DMSO-d6) δ ppm 1.29 (t, J=7.09 Hz, 3H), 3.59 (s, 3H), 4.30 (q, J=7.09 Hz, 2H), 7.43-7.57 (m, 1H), 8.03 (t, J=9.05 Hz, 1H), 8.27 (s, 1H), 8.85-9.25 (m, 1H), 11.06 (br s, 1H). LC-MS: (ES, m/z): [M+1]$^+$ 353.1

G. 1-(8-fluoroimidazo[1,2-a]pyridin-5-yl)-5-(methylsulfonyl)-1H-pyrazole-4-carboxylic Acid, cpd 8g

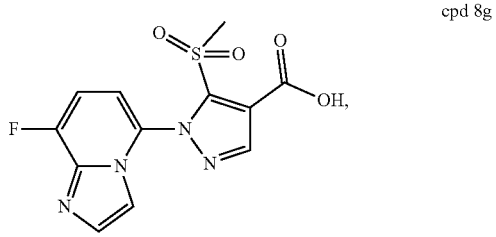 [SMILES: CS(=O)(=O)c1c(C(=O)O)cnn1-c1ccc(F)c2nccn12]

Ethyl 1-(8-fluoroimidazo[1,2-a]pyridin-5-yl)-5-(methylsulfonyl)-1H-pyrazole-4-carboxylate (80 mg, 0.23 mmol) in THF (8 mL) and water (2 mL) was added lithium hydroxide (95.3 mg, 2.27 mmol). The reaction mixture was stirred at rt overnight. To the mixture was added EtOAc (20 mL) and the mixture was adjusted to pH 1 by the addition of 3M HCl. The mixture was then extracted with EtOAc (30 mL×3). The organic layers were dried over MgSO$_4$, filtered, and the filtrate concentrated to give the product as a white solid (60 mg, 81.5% yield). LC-MS: (ES, m/z): [M+1]$^+$ 325.1

H. N-(5-chloro-6-(2H-1,2,3-triazol-2-yl)pyridin-3-yl)-1-(8-fluoroimidazo[1,2-c]pyridin-5-yl)-5-(methylsulfonyl)-1H-pyrazole-4-carboxamide, cpd 8

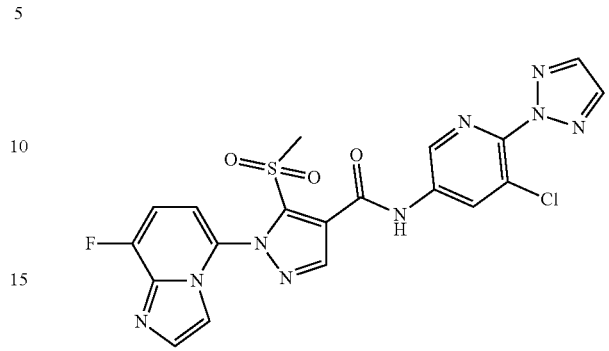

POCl$_3$ (113.5 mg, 0.74 mmol) was added dropwise to a solution of 1-(8-fluoroimidazo[1,2-c]pyridin-5-yl)-5-(methylsulfonyl)-1H-pyrazole-4-carboxylic acid (60 mg, 0.19 mmol), 5-chloro-6-(2H-1,2,3-triazol-2-yl)pyridin-3-amine (43.4 mg, 0.22 mmol) and pyridine (87.8 mg, 1.11 mmol) in dichloromethane (10 mL). The mixture was stirred at rt for 2 h. The mixture was adjusted to pH 9-10 by the addition of sat. NaHCO$_3$. Water (30 mL) was added, and the mixture extracted with dichloromethane (30 mL×3). The combined organic layers were dried over MgSO$_4$, filtered, and the filtrate concentrated under reduced pressure to give the crude product. The crude was purified by preparative high-performance liquid chromatography on a column: Boston Prime C18 150*30 mm Sum. Condition: A: water (0.05% ammonia hydroxide v/v); B: CH$_3$CN; at the beginning: A (69%) and B (31%), at the end: A: (39%) and B (61%). Gradient Time(min) 8; 100% B Hold Time(min) 2; Flow Rate(ml/min) 25. The pure fractions were collected and the organic solvent was concentrated under reduced pressure, then lyophilized to dryness to afford the product as a white solid (13.0 mg, 13.9% yield). $^1$H NMR (400 MHz, DMSO-d6) δ ppm 3.59 (s, 3H), 7.35-7.44 (m, 2H), 7.51 (dd, J=8.07, 3.91 Hz, 1H), 7.71 (d, J=0.98 Hz, 1H), 8.17 (s, 2H), 8.61-8.69 (m, 2H), 8.81 (d, J=2.20 Hz, 1H). LC-MS: (ES, m/z): [M+1]$^+$ 502.1

Example 9

N-(5-chloro-6-(5-methyloxazol-2-yl)pyridin-3-yl)-1-(8-fluoroimidazo[1,2-a]pyridin-5-yl)-5-(trifluoromethyl)-1H-pyrazole-4-carboxamide, cpd 9

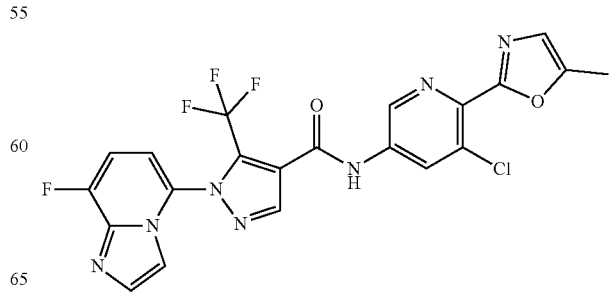

A. 5-Bromo-3-chloro-N-(prop-2-yn-1-yl)picolinamide, cpd 9a

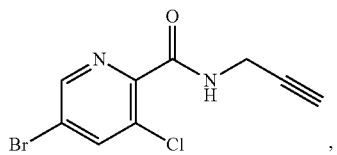

A mixture of 5-bromo-3-chloropicolinic acid (500 mg, 2.12 mmol), HOBT (143 mg, 2.54 mmol), DECI (405 mg, 1.06 mmol) and TEA (428 mg, 4.23 mmol) in DMF (5 mL) was stirred at rt for 0.5 h. Prop-2-yn-1-amine (140 mg, 2.54 mmol) was added to the mixture. The mixture was stirred at rt for 12 h. Water (10 mL) was added to the mixture and the mixture was extracted with EtOAc (20 mL×3). The combined organic layers were dried over $Na_2SO_4$, filtered, and the filtrate concentrated to afford a crude product. The crude product was purified by flash column chromatography over silica gel (eluent: petroleum ether/ethyl acetate from 100/0 to 100/50). The eluent was collected and the solvent was concentrated under reduced pressure to give the title compound (160 mg, 27.7% yield). LC-MS: (ES, m/z): $[M+1]^+$ 274.9

B. 2-(5-bromo-3-chloropyridin-2-yl)-5-methyloxazole, cpd 9b

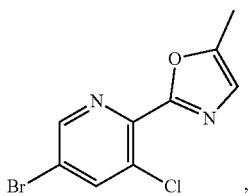

Trifluoromethanesulfonic acid (878 mg, 5.85 mmol) was dropwise added to a solution of 5-bromo-3-chloro-N-(prop-2-yn-1-yl)picolinamide (160 mg, 0.59 mmol) in dichloromethane (3 mL), the mixture was stirred at 90° C. for 14 h. To the mixture was added water (5 mL) and the mixture extracted with EtOAc (10 mL×3). The combined organic layers were dried over $Na_2SO_4$ and concentrated to afford a crude product. The crude product was purified by flash column chromatography over silica gel (eluent: petroleum ether/ethyl acetate from 100/0 to 0/100). The eluent was collected and the solvent was concentrated under reduced pressure to afford the product as a white solid (110 mg, 68.8% yield). $^1$H NMR (400 MHz, DMSO-d6) δ ppm 2.41 (d, J=1.2 Hz, 3H), 7.16 (d, J=1.0 Hz, 1H), 8.53 (d, J=2.0 Hz, 1H), 8.80 (d, J=2.0 Hz, 1H). LC-MS: (ES, m/z): $[M+1]^+$ 274.9

C. 3,6-difluoro-2-hydrazinylpyridine, cpd 9c

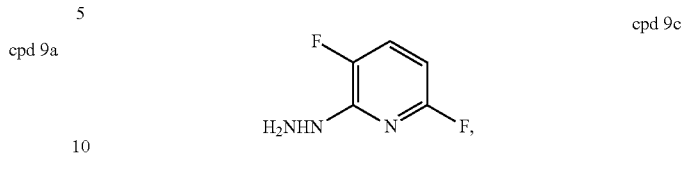

To an ice-cold solution of 2,3,6-trifluoropyridine (4 g, 30.06 mmol) in EtOH (50 mL) was added hydrazine hydrate (3.071 g, 60.12 mmol). The reaction mixture was warmed up to r.t. and then heated at reflux for 2 h. After it was cooled to r.t., the reaction mixture was diluted with water (50 mL) and extracted with $CH_2Cl_2$ (2×100 mL). The combined organic layers were dried over anhydrous $Na_2SO_4$, filtered, and the filtrate concentrated under reduced pressure. The residue was re-crystallized from EtOH to obtain the product as a light yellow solid (3 g, yield: 68.8%).

D. 2-bromo-3,6-difluoropyridine, cpd 9d

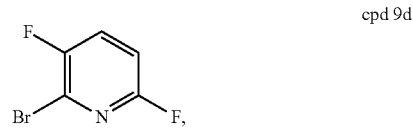

$Br_2$ (2.13 mL, 41.35 mmol) was added dropwise to a stirred solution of 3,6-difluoro-2-hydrazinylpyridine (3 g, 20.67 mmol) in $CHCl_3$ (45 mL) at room temperature. The mixture was stirred at 60° C. for 1 h. The mixture was cooled at 0° C. and a saturated solution of $NaHCO_3$(200 mL) was added dropwise. $CH_2Cl_2$ (200 mL) was added, the organic layer was separated, dried ($Na_2SO_4$), filtered and the solvents concentrated under reduced pressure. The residue was purified by flash column chromatography over silica gel (petroleum ether: EtOAc=1:0~9:1) to yield the product as a yellow oil (1.7 g, yield: 42.4%). $^1$H NMR (400 MHz, DMSO-d6) δ ppm 6.92 (td, J=3.1, 8.7 Hz, 1H), 7.55 (td, J=6.2, 8.6 Hz, 1H).

E. 2-bromo-3-fluoro-6-hydrazinylpyridine, cpd 9e

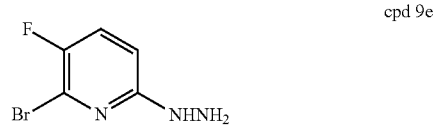

2-Bromo-3,6-difluoropyridine (2.7 g, 13.92 mmol) was dissolved in MeCN (50 mL) and hydrazine hydrate (1.422 g, 27.84 mmol) was added. The reaction mixture was stirred at 80° C. for 16 h. The reaction mixture was concentrated under reduced pressure to afford crude as a yellow solid (2.868 g, yield:100%).

F. ethyl 1-(6-bromo-5-fluoropyridin-2-yl)-5-(trifluoromethyl)-1H-pyrazole-4-carboxylate, cpd 9f

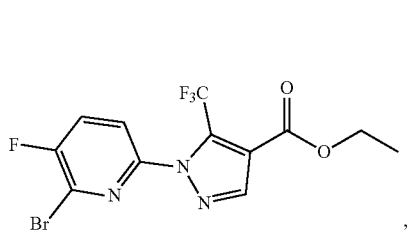

cpd 9f

2-Bromo-3-fluoro-6-hydrazinylpyridine (2.8 g, 13.59 mmol) was dissolved in EtOH (60 mL), ethyl 2-(ethoxymethylene)-4,4,4-trifluoro-3-oxobutanoate (6.529 g, 27.18 mmol) was added and stirred at 60° C. for 2 h. The mixture was concentrated under reduced pressure to afford crude product. The crude product was purified by flash column chromatography over silica gel (eluent: petroleum ether/ethyl acetate from 100/0 to 80/20). The desired fractions were collected and the solvent was concentrated under reduced pressure to afford compound as a yellow solid (2 g, yield: 38.5%). $^1$H NMR (400 MHz, DMSO-d6) δ ppm 1.38-1.41 (m, 3H), 4.37-4.41 (m, 2H), 7.63-7.67 (m, 2H), 8.11 (s, 1H).

G. ethyl 1-(6-((tert-butoxycarbonyl)amino)-5-fluoropyridin-2-yl)-5-(trifluoromethyl)-1H-pyrazole-4-carboxylate, cpd 9g

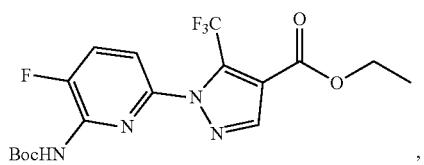

cpd 9g

Pd(OAc)$_2$ (58.755 mg, 0.26 mmol) and Xantphos (151.428 mg, 0.26 mmol) in dioxane (50 mL) were stirred at rt for 10 min under nitrogen. Ethyl 1-(6-bromo-5-fluoropyridin-2-yl)-5-(trifluoromethyl)-1H-pyrazole-4-carboxylate (2 g, 5.23 mmol), Cs$_2$CO$_3$ (5.116 g, 15.70 mmol) and tert-butyl carbamate (0.736 g, 6.28 mmol) were then added at room temperature. The reaction mixture was then allowed to heat at 90° C. overnight and before cooling to rt. The reaction mixture was filtered though a pad of diatomaceous earth. The filtrate was concentrated under reduced pressure, then purified by flash column chromatography over silica gel (eluent: petroleum ether/EtOAc 100/0 to petroleum ether/EtOAc 80/20). The desired fractions were collected and the solvent was concentrated to dryness under reduced pressure to give the desired product as a yellow solid (1800 mg, yield: 82.2%).

H. ethyl 1-(6-amino-5-fluoropyridin-2-yl)-5-(trifluoromethyl)-1H-pyrazole-4-carboxylate, cpd 9h

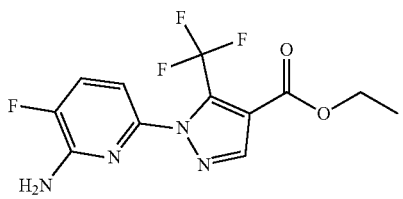

cpd 9h

Ethyl 1-(6-((tert-butoxycarbonyl)amino)-5-fluoropyridin-2-yl)-5-(trifluoromethyl)-1H-pyrazole-4-carboxylate (0.9 g, 2.15 mmol) and HCl/MeOH (18 mL, 4 M) were stirred at 30° C. for 1 h. The mixture was concentrated to dryness. To the residue was added saturated aqueous K$_2$CO$_3$ (50 mL). The mixture was extracted with EtOAc (50 mL×3). The combined organic layers were dried over Na$_2$SO$_4$, filtered and the filtrate was concentrated to dryness to give the product as an orange gum (650 mg, yield: 94.9%).

I. ethyl 1-(8-fluoroimidazo[1,2-a]pyridin-5-yl)-5-(trifluoromethyl)-1H-pyrazole-4-carboxylate, cpd 9i

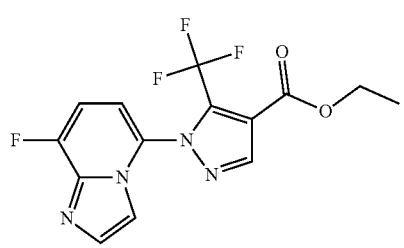

cpd 9i

Ethyl 1-(6-amino-5-fluoropyridin-2-yl)-5-(trifluoromethyl)-1H-pyrazole-4-carboxylate (650 mg, 2.043 mmol) was dissolved in EtOH (20 mL) under N$_2$. 2-Bromo-1,1-diethoxyethane (805.057 mg, 4.085 mmol) was added to the suspension followed by HBr (2 mL, 48% in water). The resulting mixture was then refluxed for 12 h and cooled to room temperature. The solvent was removed under reduced pressure. The residue was purified by flash column chromatography over silica gel (petroleum ether: ethyl acetate=10:1~1:1). The pure fractions were collected and the solvent was concentrated under reduced pressure to afford the product as a light yellow solid (320 mg, yield: 45.8%). $^1$H NMR (400 MHz, CHLOROFORM-d) δ ppm 1.40 (t, J=7.2 Hz, 3H), 4.42 (q, J=7.1 Hz, 2H), 6.91 (dd, J=4.0, 7.9 Hz, 1H), 7.04 (dd, J=8.0, 9.4 Hz, 1H), 7.12 (s, 1H), 7.70 (s, 1H), 8.30 (s, 1H).

J. 1-(8-fluoroimidazo[1,2-a]pyridin-5-yl)-5-(trifluoromethyl)-1H-pyrazole-4-carboxylic Acid, cpd 9j

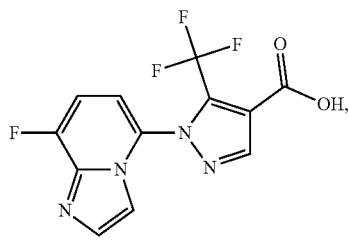

cpd 9j

The mixture of ethyl 1-(8-fluoroimidazo[1,2-a]pyridin-5-yl)-5-(trifluoromethyl)-1H-pyrazole-4-carboxylate (320 mg, 0.935 mmol) in concentrated HCl (6.064 mL) was stirred at 130° C. for 2 h. The solvent was concentrated under reduced pressure to afford the product as a yellow solid (300 mg, crude).

K. N-(5-chloro-6-(5-methyloxazol-2-yl)pyridin-3-yl)-1-(8-fluoroimidazo[1,2-a]pyridin-5-yl)-5-(trifluoromethyl)-1H-pyrazole-4-carboxamide, cpd 9

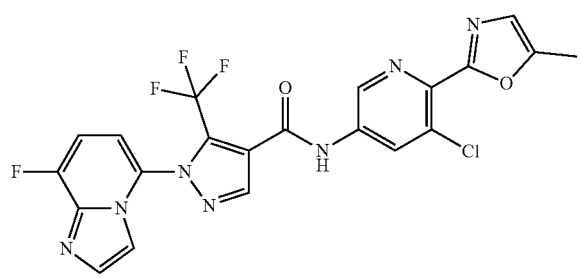 [SMILES: Cc1cnc(-c2ncc(NC(=O)c3cnn(-c4ccc(F)c5nccn45)c3C(F)(F)F)cc2Cl)o1]

Pd$_2$(dba)$_3$ (44 mg, 0.048 mmol) and 4,5-bis(diphenylphosphino)-9,9-dimethylxanthene (140 mg, 0.24 mmol) was added to a solution of 1-(8-fluoroimidazo[1,2-a]pyridin-5-yl)-5-(trifluoromethyl)-1H-pyrazole-4-carboxamide (50 mg, 0.16 mmol), 2-(5-bromo-3-chloropyridin-2-yl)-5-methyloxazole (52 mg, 0.19 mmol) and cesium carbonate (33 mg, 0.24 mmol) in toluene (3 mL). The mixture was stirred at 80° C. for 14 h under N$_2$. To the mixture was added water (5 mL) and the mixture was extracted with EtOAc (10 mL×3). The combined organic layers were dried over Na$_2$SO$_4$, filtered, and the filtrate concentrated to afford a crude product. The crude product was purified by preparative high-performance liquid chromatography. Column: Xtimate C18 10μ 250 mm*50 mm, Condition: A: water (0.04% NH$_3$H$_2$O+10 mM NH$_4$HCO$_3$); B: MeCN at the beginning: A (60%) and B (40%) at the end: A (30%) and B (70%). Gradient Time(min) 8; 100% B Hold Time(min) 2; Flow Rate(ml/min) 25. The pure fractions were collected and the solvent concentrated under reduced pressure, then lyophilized to dryness to afford the title compound (33 mg, 40.7%). $^1$H NMR (400 MHz, DMSO-d$_6$) δ ppm 2.42 (d, J=1.2 Hz, 3H), 7.14 (d, J=1.2 Hz, 1H), 7.41-7.55 (m, 3H), 7.79 (d, J=1.2 Hz, 1H), 8.55 (d, J=2.2 Hz, 1H), 8.70 (s, 1H), 8.92 (d, J=2.2 Hz, 1H), 11.20 (br s, 1H). LC-MS: (ES, m/z): [M+1]$^+$ 506.1

Example 10

N-(5-chloro-6-(4-methyloxazol-2-yl)pyridin-3-yl)-1-(8-fluoroimidazo[1,2-a]pyridin-5-yl)-5-(trifluoromethyl)-1H-pyrazole-4-carboxamide, cpd 10

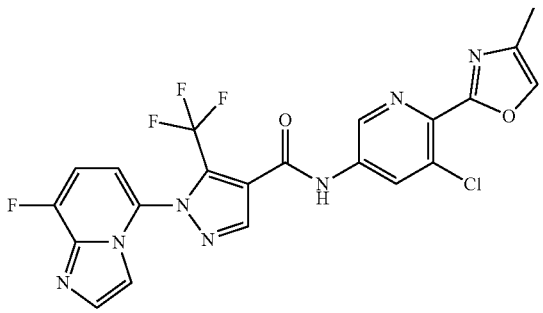 [SMILES: Cc1coc(-c2ncc(NC(=O)c3cnn(-c4ccc(F)c5nccn45)c3C(F)(F)F)cc2Cl)n1]

A. 5-Bromo-3-chloropicolinoyl chloride, cpd 10a

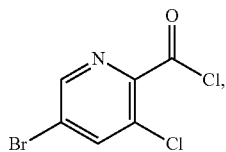

cpd 10a

Oxalyl dichloride (3.60 mL, 42.3 mmol) in DMF (0.05 mL) was added to a solution of 5-bromo-3-chloropicolinic acid (5.0 g, 22.15 mmol) in dichloromethane at 0° C. The mixture was stirred at rt for 2 h. The solvent was concentrated under reduced pressure to give the crude product (5.5 g, 100% yield).

B. (S)-5-bromo-3-chloro-N-(1-(methoxy(methyl)amino)-1-oxopropan-2-yl)picolinamide, cpd 10b

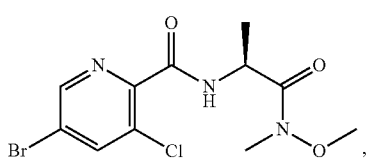

cpd 10b

5-Bromo-3-chloropicolinoyl chloride (200 mg, 0.79 mmol) was added to a solution of (S)-2-amino-N-methoxy-N-methylpropanamide (132 mg, 0.79 mmol) and TEA (397 mg, 3.92 mmol) in dichloromethane (20 mL). The mixture was stirred at rt for 16 h. Brine (30 mL) was added to the mixture, the mixture was extracted with EtOAc (50 mL×2). The combined organic layers were concentrated under reduced pressure. The crude product was purified by column chromatography over silica gel (eluent: petroleum ether/ethyl acetate=1:0 to petroleum ether/ethyl acetate=1:1). The desired fractions were collected and the solvent was concentrated under reduced pressure to afford the product as a yellow solid (180 mg, 65.43% yield). $^1$H NMR (400 MHz, DMSO-d6) δ ppm 1.28 (3H, d, J=7.09 Hz), 3.13 (3H, s), 3.77 (3H, s), 4.89 (1H, br t, J=6.97 Hz), 8.43 (1H, d, J=1.71 Hz), 8.70 (1H, d, J=1.96 zH), 8.84 (1H, br d, J=7.58 Hz). LC-MS: (ES, m/z): [M+1]$^+$ 352.0

C. (S)-5-Bromo-3-chloro-N-(1-oxopropan-2-yl)picolinamide, cpd 10c

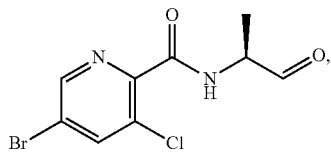

cpd 10c (S)-5-Bromo-3-chloro-N-(1-(methoxy(methyl)amino)-1-oxopropan-2-yl)picolinamide (2.0 g, 5.71 mmol) was dissolved THF (30 mL) and the mixture was stirred at −78° C. for 10 min. Lithium aluminum hydride (238.2 mg, 6.28 mmoL) in THF (30 mL) was added slowly to the mixture. The reaction was stirred for 1 h at 0° C. Water (0.24 mL) was slowly added, followed by 10% NaOH solution (0.24 mL) and additional water (0.72 mL). The mixture was stirred at rt for 1 min, filtered, and the organic phase was concentrated under reduced pressure to afford a yellow oil, which was then purified by column chromatography over silica gel (eluent: petroleum ether to petroleum ether/ethyl acetate=1:1). The desired fractions were collected and the solvent was concentrated under reduced pressure to afford the product as a yellow oil (1.8 g, 50.8% yield). LC-MS: (ES, m/z): [M+1]$^+$ 293.0

D. 2-(5-Bromo-3-chloropyridin-2-yl)-4-methyloxazole, cpd 10d

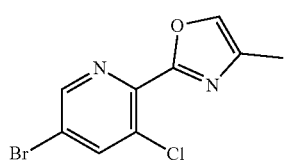

cpd 10d (S)-5-Bromo-3-chloro-N-(1-oxopropan-2-yl)picolinamide (1.7 g, 2.74 mmol) was dissolved in methanesulfonic acid (30 mL) and phosphorus (V) oxide (1.17 g, 8.21 mmol) was added. The reaction mixture was stirred at 140° C. for 1 h. The reaction mixture was slowly poured into water (200 mL) and the mixture extracted with EtOAc (200 mL×3). The combined organic layers were dried over Na$_2$SO$_4$, filtered, and the filtrates were concentrated under reduced pressure to afford the crude product as a black solid. The crude product was purified by flash column chromatography over silica gel (eluent: petroleum ether/ethyl acetate from 100/0 to 50/50). The desired fractions were collected and the solvent was concentrated under reduced pressure to afford the title compound as a white solid (110 mg, 14.1% yield). LC-MS: (ES, m/z): [M+1]$^+$ 275.0

E. N-(5-chloro-6-(4-methyloxazol-2-yl)pyridin-3-yl)-1-(8-fluoroimidazo[1,2-a]pyridin-5-yl)-5-(trifluoromethyl)-1H-pyrazole-4-carboxamide, cpd 10

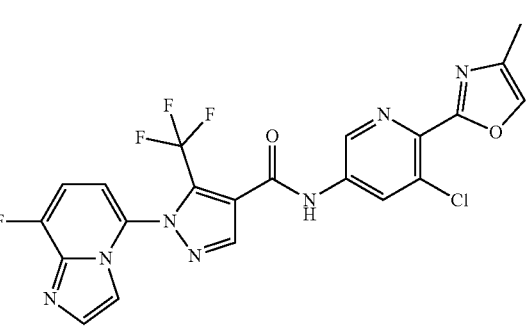

Pd$_2$(dba)$_3$ (22 mg, 0.024 mmol) and 4,5-bis(diphenylphosphino)-9,9-dimethylxanthene (46.5 mg, 0.080 mmol) was added to a solution of 1-(8-fluoroimidazo[1,2-a]pyridin-5-yl)-5-(trifluoromethyl)-1H-pyrazole-4-carboxamide (138 mg, 0.44 mmol), 2-(5-bromo-3-chloropyridin-2-yl)-4-methyloxazole (110 mg, 0.40 mmol) and cesium carbonate (197 mg, 0.60 mmol) in toluene (5 mL). The mixture was stirred at 80° C. for 14 h under N$_2$. To the mixture was added water (5 mL) and the mixture extracted with EtOAc (10 mL×3). The combined organic layers were dried over Na$_2$SO$_4$, filtered, and the filtrate concentrated to afford the crude product. The crude product was purified by preparative high-performance liquid chromatography. Column: Xtimate C18 10µ 250 mm*50 mm, Condition: A: water (0.04% NH$_3$H$_2$O+10 mM NH$_4$HCO$_3$); B: MeCN. at the beginning: A (60%) and B (40%) at the end: A (30%) and B (70%). Gradient Time(min) 8.5; 100% B Hold Time(min) 2; Flow Rate(ml/min) 30. The pure fractions were collected and the solvent was concentrated under reduced pressure, lyophilized to dryness, to afford the title compound as a pale yellow solid (60 mg. 29.2%). $^1$H NMR (400 MHz, DMSO-d6) δ ppm 2.18 (3H, s), 7.39-7.43 (1H, m), 7.44-7.48 (1H, m), 7.50 (1H, d, J=2.93 Hz), 7.75 (1H, s), 8.00 (1H, s), 8.51 (1H, d, J=1.96 Hz), 8.66 (1H, s), 8.90 (1H, d, J=1.96 Hz), 11.17 (1H, br s). LC-MS: (ES, m/z): [M+1]$^+$ 506.0

Example 11

1-(7-cyanopyrazolo[1,5-a]pyridin-4-yl)-5-(trifluoromethyl)-N-(2-(trifluoromethyl)pyridin-4-yl)-1H-pyrazole-4-carboxamide, cpd 11

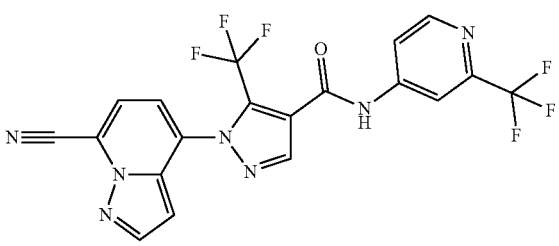 [SMILES: N#Cc1ccc(-n2ncc(C(=O)Nc3ccnc(C(F)(F)F)c3)c2C(F)(F)F)c2ccnn12]

A. 4-Hydrazinylpyrazolo[1,5-a]pyridine-7-carbonitrile, cpd 11a

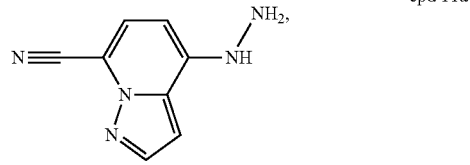

Hydrazine (812 mg, 25.3 mmol) was added to a solution of 4-chloropyrazolo[1,5-a]pyridine-7-carbonitrile (150 mg, 0.85 mmol) in acetonitrile (7.5 mL). The mixture was stirred at 90° C. for 6 h. EtOH (30 mL×2) was added to the mixture. The solvents were concentrated under reduced pressure to afford a crude product as a yellow oil (160 mg) which was used directly for the next step.

B. Ethyl 1-(7-cyanopyrazolo[1,5-a]pyridin-4-yl)-5-(trifluoromethyl)-1H-pyrazole-4-carboxylate, cpd 11b

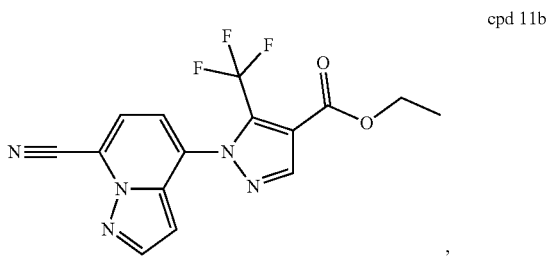 [SMILES: CCOC(=O)c1cnn(-c2ccc(C#N)n3nccc23)c1C(F)(F)F ; ","]

Ethyl 2-(ethoxymethylene)-4,4,4-trifluoro-3-oxobutanoate (222 mg, 0.92 mmol) was added to a solution of 4-hydrazinylpyrazolo[1,5-a]pyridine-7-carbonitrile (160 mg, 0.92 mmol) in ethanol (10 mL). The mixture was stirred at 80° C. for 2 h. The solvent was concentrated under reduced pressure to afford a crude product as a brown oil. The crude product was purified by column chromatography over silica gel (eluent: petroleum ether/ethyl acetate=1:0 to petroleum ether/ethyl acetate=2:1). The desired fractions were collected and the solvent was concentrated under reduced pressure to afford the product as a yellow solid (320 mg). LC-MS: (ES, m/z): [M+1]$^+$ 350.0

C. 1-(7-Cyanopyrazolo[1,5-a]pyridin-4-yl)-5-(trifluoromethyl)-1H-pyrazole-4-carboxylic acid, cpd 11c

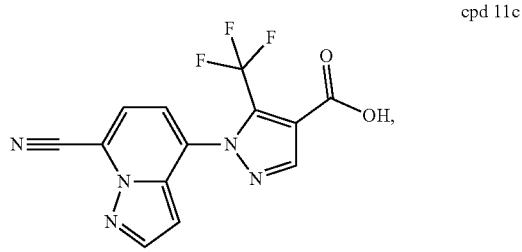 [SMILES: N#Cc1ccc(-n2ncc(C(=O)O)c2C(F)(F)F)c2ccnn12]

Lithium hydroxide (30.9 mg, 1.29 mmol) was added to a solution of ethyl 1-(7-cyanopyrazolo[1,5-a]pyridin-4-yl)-5-(trifluoromethyl)-1H-pyrazole-4-carboxylate (300 mg, 0.86 mmol) in THF/water (1:1, 2.5 mL). The mixture was reacted at room temperature for 3 h. The solvent was removed under reduced pressure and water (20 mL) was added to the mixture. The mixture was adjusted to pH 5 by the addition of 1M hydrochloric acid, then extracted with ethyl acetate (30 mL×3). The combined organic layers were washed with brine, dried over MgSO$_4$, filtered, and the filtrates were concentrated under reduced pressure to afford a mixture of 1-(7-cyanopyrazolo[1,5-a]pyridin-4-yl)-5-(trifluoromethyl)-1H-pyrazole-4-carboxylic acid and 1-(7-carbamoylpyrazolo[1,5-a]pyridin-4-yl)-5-(trifluoromethyl)-1H-pyrazole-4-carboxylic acid. The mixture was then treated with pyridine (80.8 mg, 1.02 mmol) and 2,2,2-trifluoroacetic anhydride (103 mg, 0.49 mmol) in THF (5 mL) at rt for 1 h. The mixture was adjusted to pH 5 by the addition of 1M hydrochloric acid, then extracted with ethyl acetate (30 mL×3). The combined organic layers were washed with brine, dried over MgSO$_4$, filtered, and the filtrates concentrated under reduced pressure to afford the product as a yellow solid (300 mg), which was used directly for the next step. LC-MS: (ES, m/z): [M+1]$^+$ 322.0

D. 1-(7-Cyanopyrazolo[1,5-a]pyridin-4-yl)-5-(trifluoromethyl)-N-(2-(trifluoromethyl)pyridin-4-yl)-1H-pyrazole-4-carboxamide, cpd 11

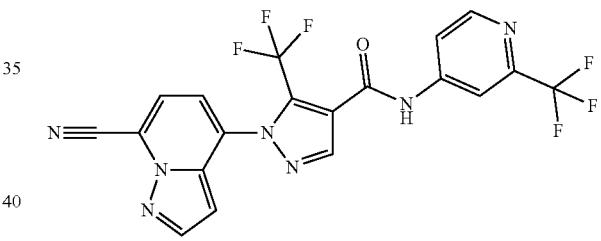

POCl$_3$ (0.13 mL, 1.68 mmol) was added to a mixture of 1-(7-cyanopyrazolo[1,5-a]pyridin-4-yl)-5-(trifluoromethyl)-1H-pyrazole-4-carboxylic acid (300 mg, 0.69 mmol), 2-(trifluoromethyl)pyridin-4-amine (111.6 mg, 0.69 mmol) and pyridine (0.28 mL, 3.44 mmol) in methylene chloride (10 mL). The reaction mixture was stirred at 20° C. for 1 h. Aqueous sat. NaHCO$_3$ solution (20 mL) was added to the mixture. The mixture was extracted with CH$_2$Cl$_2$ (30 mL×2). The combined organic layers were washed with brine, dried over Na$_2$SO$_4$, filtered, and the filtrate concentrated under reduced pressure to afford crude product as a brown oil. The crude product was purified by preparative high-performance liquid chromatography: Column: Phenomenex Gemini 150*25 mm*10 um; Condition: A: water (0.05% ammonia hydroxide v/v); B: MeCN at the beginning: A (50%) and B (50%); at the end: A (20%) and B (80%). Gradient Time(min) 10; 100% B Hold Time(min) 2.2; Flow Rate(ml/min) 25. The pure fractions were collected, the organic solvent concentrated under reduced pressure, then the residue was lyophilized to dryness to give the product (172 mg, 52.2%) as a yellow solid. $^1$H NMR (400 MHz, DMSO-d6) δ ppm 6.69 (1H, d, J=2.51 Hz), 7.79 (1H, d, J=7.78 Hz), 7.98 (1H, dd, J=5.52, 1.76 Hz), 8.06 (1H, d, J=7.78 Hz), 8.24 (1H, d, J=1.76 Hz), 8.36 (1H, d, J=2.26

Hz), 8.63 (1H, s), 8.72 (1H, d, J=5.52 Hz), 11.28 (1H, br s). LC-MS: (ES, m/z): [M+1]⁺ 465.9

Example 12

4-(5-(trifluoromethyl)-4-((2-(trifluoromethyl)pyridin-4-yl)carbamoyl)-1H-pyrazol-1-yl)pyrazolo[1,5-a]pyridine-7-carboxamide, cpd 12

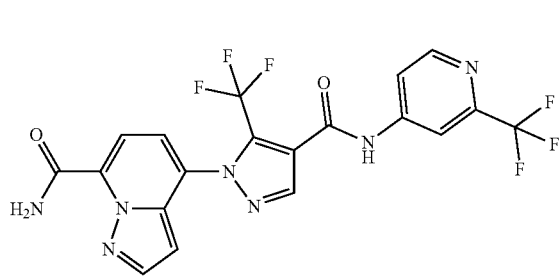 [SMILES: NC(=O)c1ccc(-n2ncc(C(=O)Nc3ccnc(C(F)(F)F)c3)c2C(F)(F)F)c2ccnn12]

A. 1-(7-carbamoylpyrazolo[1,5-a]pyridin-4-yl)-5-(trifluoromethyl)-1H-pyrazole-4-carboxylic Acid, cpd 12a

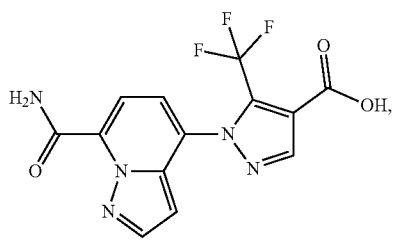

cpd 12a

Lithium hydroxide (60.0 mg, 2.50 mmol) was added to a solution of ethyl 1-(7-cyanopyrazolo[1,5-a]pyridin-4-yl)-5-(trifluoromethyl)-1H-pyrazole-4-carboxylate (500 mg, 1.25 mmol) in THF/water (92:1, 6 mL). The mixture was reacted at room temperature for 16 h. Water (20 mL) was added to the mixture. The mixture was adjusted to pH 5 by the addition of 1M hydrochloric acid, and then extracted with ethyl acetate (30 mL×3). The combined organic layers were washed with brine, dried over MgSO₄, filtered, and the filtrate concentrated under reduced pressure to afford a brown oil, which was purified by preparative high-performance liquid chromatography: Column: Agela ASB 150*25 mm*5 um. Condition: A: water(0.05% HCl), B: MeCN, at the beginning: A (75%) and B (25%), at the end: A (45%) and B (55%). Gradient Time(min) 8; 100% B Hold Time (min) 0; Flow Rate(ml/min) 25. The pure fractions were collected, the organic solvent was concentrated under reduced pressure and the resulting residue lyophilized to dryness to give the product as a white solid (170 mg, 40.2% yield). LC-MS: (ES, m/z): [M+1]⁺ 339.9

B. 4-(5-(trifluoromethyl)-4-((2-(trifluoromethyl)pyridin-4-yl)carbamoyl)-1H-pyrazol-1-yl)pyrazolo[1,5-a]pyridine-7-carboxamide, cpd 12

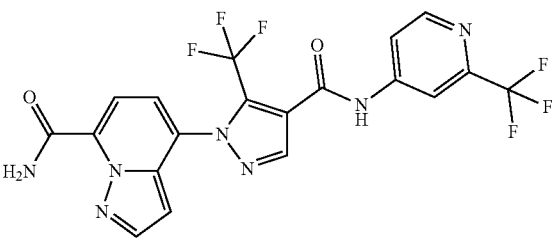 [SMILES: NC(=O)c1ccc(-n2ncc(C(=O)Nc3ccnc(C(F)(F)F)c3)c2C(F)(F)F)c2ccnn12]

POCl₃ (0.13 mL, 1.68 mmol) was added to a mixture of 1-(7-carbamoylpyrazolo[1,5-a]pyridin-4-yl)-5-(trifluoromethyl)-1H-pyrazole-4-carboxylic acid (80 mg, 0.23 mmol), 2-(trifluoromethyl)pyridin-4-amine (38.2 mg, 0.23 mmol) and pyridine (38.3 mg, 0.47 mmol) in methylene chloride (6 mL). The reaction mixture was stirred at 20° C. for 1 h. Aqueous sat. NaHCO₃ solution (20 mL) was added to the mixture. The mixture was extracted with CH₂Cl₂ (30 mL×2). The combined organic layers were washed with brine, dried over Na₂SO₄, filtered, and the filtrate concentrated under reduced pressure to afford crude product as a brown oil. The crude product was purified by preparative high-performance liquid chromatography: Column: Phenomenex Gemini 150*25 mm*10 um; Condition: A: water (0.05% ammonia hydroxide v/v); B: MeCN at the beginning: A (85%) and B (15%); at the end: A (55%) and B (45%). Gradient Time(min) 12; 100% B Hold Time(min) 2.2; Flow Rate(ml/min) 25. The pure fractions were collected, the organic solvent was concentrated under reduced pressure and lyophilized to dryness to give the product (44 mg, 38.6%) as a pale yellow solid. ¹H NMR (400 MHz, DMSO-d6) δ ppm 6.57 (1H, d, J=2.45 Hz), 7.71-7.76 (1H, m), 7.78-7.83 (1H, m), 7.96 (1H, dd, J=5.38, 1.71 Hz), 8.22 (1H, d, J=1.71 Hz), 8.31 (1H, d, J=2.45 Hz), 8.55 (1H, br s), 8.58 (1H, s), 8.70 (1H, d, J=5.38 Hz), 9.48 (1H, br s), 11.27 (1H, br s). LC-MS: (ES, m/z): [M+1]⁺ 483.9

Following the procedures described in Example 12, above, and selecting and substituting the appropriate reagents, starting materials, and purification methods, and adjusting reaction temperatures, times and other variables or parameters, as needed or desirable, as would be readily recognized by those skilled in the art, the following compounds (13-16) were prepared.

Example 13

N-(5-chloro-6-(2H-1,2,3-triazol-2-yl)pyridin-3-yl)-1-(7-cyanopyrazolo[1,5-a]pyridin-4-yl)-5-(trifluoromethyl)-1H-pyrazole-4-carboxamide, cpd 13

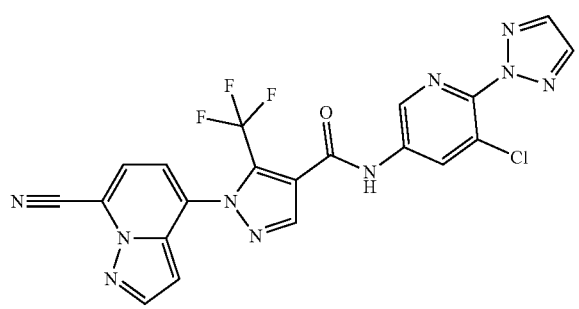 [SMILES: N#Cc1ccc(-n2ncc(C(=O)Nc3cnc(-n4nccn4)c(Cl)c3)c2C(F)(F)F)c2ccnn12]

¹H NMR (400 MHz, DMSO-d6) δ ppm 6.67 (1H, d, J=2.45 Hz), 7.76 (1H, d, J=7.58 Hz), 8.03 (1H, d, J=7.83 Hz), 8.16 (2H, s), 8.33 (1H, d, J=2.20 Hz), 8.56-8.67 (2H, m), 8.81 (1H, d, J=2.20 Hz), 11.20 (1H, br s). LC-MS: (ES, m/z): [M+1]⁺ 499.0

Example 14

1-(7-chloropyrazolo[1,5-a]pyridin-4-yl)-5-(trifluoromethyl)-N-(2-(trifluoromethyl)pyridin-4-yl)-1H-pyrazole-4-carboxamide, cpd 14

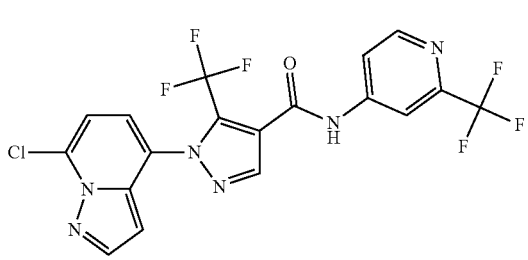 [SMILES: O=C(Nc1ccnc(C(F)(F)F)c1)c1cnn(-c2ccc(Cl)n3nccc23)c1C(F)(F)F]

¹H NMR (400 MHz, DMSO-d6) δ ppm 6.53 (d, J=2.20 Hz, 1H), 7.43 (d, J=7.83 Hz, 1H), 7.65 (d, J=7.83 Hz, 1H), 7.94 (dd, J=5.62, 1.71 Hz, 1H), 8.20 (d, J=1.96 Hz, 1H), 8.26 (d, J=2.20 Hz, 1H), 8.54 (s, 1H), 8.68 (d, J=5.38 Hz, 1H), 11.24 (br s, 1H). LC-MS: (ES, m/z): [M+1]⁺ 475.1

Example 15

N-(5-chloro-6-(2H-1,2,3-triazol-2-yl)pyridin-3-yl)-1-(7-chloropyrazolo[1,5-a]pyridin-4-yl)-5-(trifluoromethyl)-1H-pyrazole-4-carboxamide, cpd 15

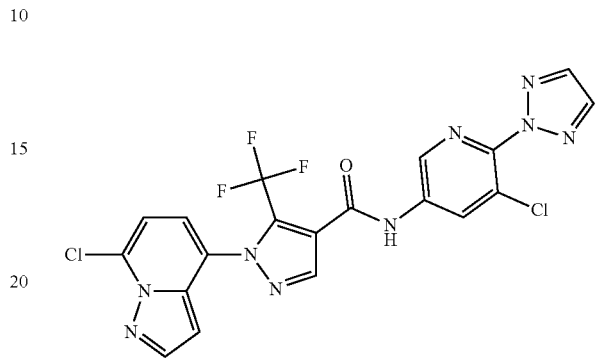

¹H NMR (400 MHz, DMSO-d6) δ ppm 6.54 (d, J=2.20 Hz, 1H), 7.43 (d, J=8.07 Hz, 1H), 7.66 (d, J=7.83 Hz, 1H), 8.16 (s, 2H), 8.26 (d, J=2.20 Hz, 1H), 8.56 (s, 1H), 8.64 (d, J=2.20 Hz, 1H), 8.81 (d, J=2.45 Hz, 1H). LC-MS: (ES, m/z): [M+1]⁺ 508.1

Example 16

4-(4-((5-chloro-6-(2H-1,2,3-triazol-2-yl)pyridin-3-yl)carbamoyl)-5-(trifluoromethyl)-1H-pyrazol-1-yl)pyrazolo[1,5-a]pyridine-7-carboxamide, cpd 16

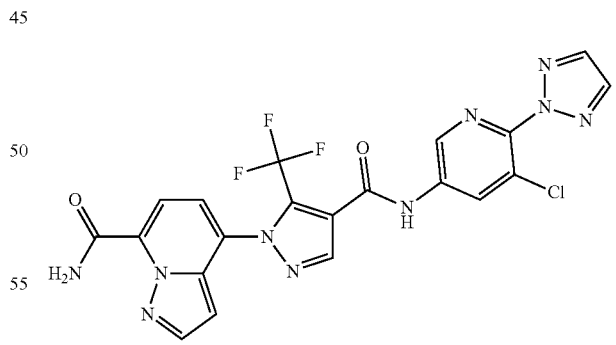

¹H NMR (400 MHz, DMSO-d6) δ ppm 6.58 (1H, d, J=2.45 Hz), 7.71-7.77 (1H, m), 7.78-7.85 (1H, m), 8.18 (2H, s), 8.31 (1H, d, J=2.45 Hz), 8.56 (1H, br s), 8.60 (1H, s), 8.66 (1H, d, J=1.96 Hz), 8.84 (1H, d, J=2.20 Hz), 9.49 (1H, br s), 11.27 (1H, br s). LC-MS: (ES, m/z): [M+1]⁺ 517.1

Example 17

(*S)—N-(5-chloro-6-(1-methoxyethyl)pyridin-3-yl)-1-(8-fluoroimidazo[1,2-a]pyridin-5-yl)-5-(trifluoromethyl)-1H-pyrazole-4-carboxamide, cpd 17

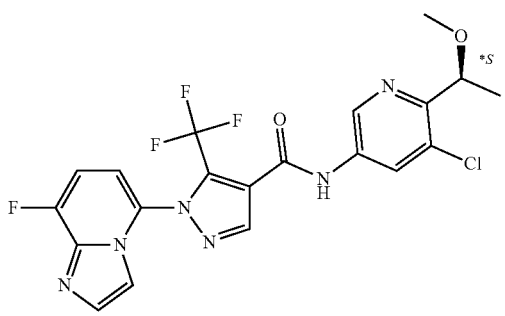 [SMILES: CO[C@@H](C)c1ncc(NC(=O)c2cnn(-c3ccc(F)c4nccn34)c2C(F)(F)F)cc1Cl]

A. 5-bromo-3-chloro-2-(1-methoxyethyl)pyridine, cpd 17a

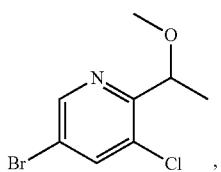

To a mixture of 1-(5-bromo-3-chloropyridin-2-yl)ethan-1-ol (8.7 g, 36.8 mmol) in DMF (8 ml) was added NaH (60%, 2.65 g, 66.2 mmol)) at 0° C. The reaction mixture was stirred at room temperature for 30 min, then CH$_3$I (26.8 g, 188.8 mmol) was added dropwise at 0° C. The mixture was stirred at room temperature for 2 h. Saturated NH$_4$Cl (50 mL) was added and the mixture was extracted with EtOAc (150 mL×2). The combined organic layers were dried over Na$_2$SO$_4$, filtered and the filtrate was concentrated under reduced pressure. The crude product was purified by column chromatography over silica gel (eluent: petroleum ether/ethyl acetate gradient from 100/0 to 85/15). The desired fractions were collected and the solvent was concentrated under reduced pressure to afford the title compound (6.1 g, 61%) as a yellow oil. LC/MS (ESI) mass calc. for C$_8$H$_9$BrClNO 249, m/z found 250.0 [M+H]$^+$

B. tert-butyl (5-chloro-6-(1-methoxyethyl)pyridin-3-yl)carbamate, cpd 17b

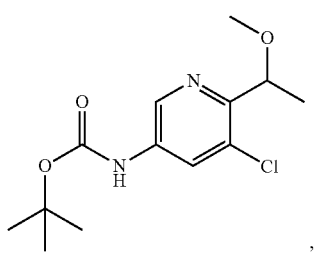

5-Bromo-3-chloro-2-(1-methoxyethyl)pyridine (6.1 g, 22.5 mmol), tert-butyl carbamate (3.1 g, 27 mmol) and Cs$_2$CO$_3$ (14.6 g, 45 mmol) were stirred in dioxane (130 ml) and the mixture was purged with N$_2$ for 5 min. Pd(OAc)$_2$ (505 mg, 2.25 mmol) and 4,5-bis(diphenylphosphino)-9,9-dimethylxanthene (1.3 g, 2.25 mmol) were added and the mixture was purged with N$_2$ for 1 min. The reaction mixture was stirred at 110° C. for 16 h. The mixture was concentrated under reduced pressure. The crude product was purified by column chromatography over silica gel (eluent: petroleum ether/ethyl acetate gradient 100/0 to 50/50). The pure fractions were collected and the organic solvent was concentrated under reduced pressure to afford the title compound (3.65 g, 44%) as a white solid. LC/MS (ESI) mass calc. for C$_{13}$H$_{19}$ClN$_2$O$_3$ 286.1, m/z found 287.1 [M+H]$^+$

C. 5-Chloro-6-(1-methoxyethyl)pyridin-3-amine, cpd 17c

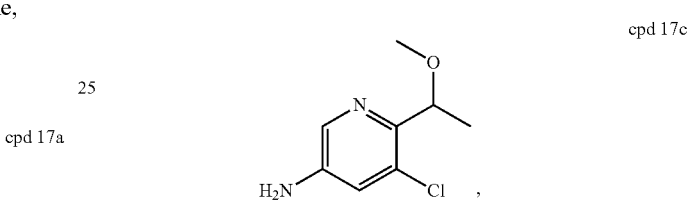

A mixture of tert-butyl (5-chloro-6-(1-methoxyethyl)pyridin-3-yl)carbamate (3.65 g, 9.92 mmol) in HCl 4M in dioxane (40 mL) was stirred at room temperature for 3 h. The solvent was concentrated under reduced pressure. The crude product was purified by column chromatography over silica gel (eluent: petroleum ether/ethyl acetate ratio 100/0 to 25/75). The pure fractions were collected and the organic solvent was concentrated under reduced pressure to yield the title compound (1.64 g, 88.5%) as a white solid. LC/MS (ESI) mass calc. for C$_8$H$_{11}$ClN$_2$O 186.1, m/z found 187.1 [M+H]$^+$

D. (*S)-5-chloro-6-(1-methoxyethyl)pyridin-3-amine, cpd 17c-1 and (*R)-5-chloro-6-(1-methoxyethyl)pyridin-3-amine, cpd 17c-2

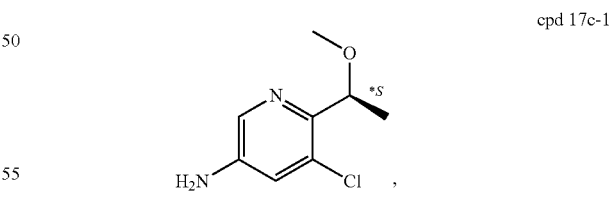

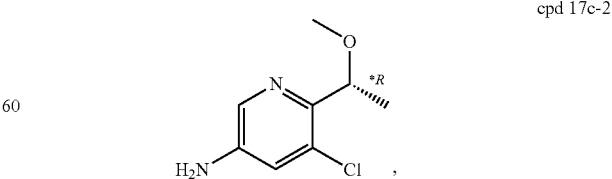

5-Chloro-6-(1-methoxyethyl)pyridin-3-amine mono HCl salt (1.64 g, 7.35 mmol) was separated by supercritical fluid chromatography. Column: DAICEL CHIRALPAK IC (250 mm×30 mm, 10 um) Mobile phase: A: Supercritical CO$_2$; B: 0.1% NH$_4$OH in ETOH; ratio A 55% B 45% at 70 mL/min. The pure fractions were collected and the solvents were concentrated under reduced pressure to yield (*S)-5-chloro-6-(1-methoxyethyl)pyridin-3-amine, cpd 17c-1(604 mg, 44%), LC/MS (ESI) mass calc. for C$_8$H$_{11}$ClN$_2$O 186.1, m/z found 187.1 [M+H]$^+$; and (*R)-5-chloro-6-(1-methoxyethyl)pyridin-3-amine, cpd 17c-2 (554 mg, 40%), LC/MS (ESI) mass calc. for C$_8$H$_{11}$ClN$_2$O 186.1, m/z found 187.1 [M+H]$^+$ E. (*S)—N-(5-chloro-6-(1-methoxyethyl)pyridin-3-yl)-1-(8-fluoroimidazo[1,2-c]pyridin-5-yl)-5-(trifluoromethyl)-1H-pyrazole-4-carboxamide, cpd 17

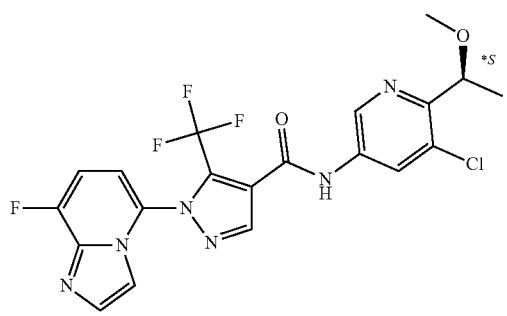 [SMILES: CO[C@@H](C)c1ncc(NC(=O)c2cnn(-c3ccc(F)c4nccn34)c2C(F)(F)F)cc1Cl]

1-(8-Fluoroimidazo[1,2-a]pyridin-5-yl)-5-(trifluoromethyl)-1H-pyrazole-4-carboxylic acid (87 mg, 0.28 mmol), (*S)-5-chloro-6-(1-methoxyethyl)pyridin-3-amine (51.9 mg, 0.28 mmol), POCl$_3$ (51.8 μL, 0.55 mmol) were dissolved in dichloromethane (5 mL), and pyridine (111 μL, 1.64 mmol) was added. The mixture was stirred at 25° C. for 1 h. Aqueous sat. NaHCO$_3$(20 mL) was added and the mixture extracted with CH$_2$Cl$_2$ (50 mL×2). The combined organic layers were dried with Na$_2$SO$_4$, filtered and the filtrates were concentrated under reduced pressure to afford the crude product as a brown oil, which was purified by preparative high-performance liquid chromatography: Column: Phenomenex Gemini 150*25 mm*10 um. Condition: A: water (0.05% ammonia hydroxide v/v)-CAN; B: MeCN, at the beginning: A (60%) and B (40%), at the end: A (30%) and B (70%). Gradient Time(min) 8; 100% B Hold Time (min) 2; Flow Rate(ml/min) 25. The pure fractions were collected, the organic solvent was concentrated under reduced pressure and the residue lyophilized to dryness to give the product as a white solid (44.5 mg, 33.3% yield). $^1$H NMR (400 MHz, DMSO-d6) δ ppm 1.42 (d, J=6.36 Hz, 3H), 3.17 (s, 3H), 4.83 (q, J=6.36 Hz, 1H), 7.40-7.57 (m, 3H), 7.78 (d, J=1.22 Hz, 1H), 8.37 (d, J=2.20 Hz, 1H), 8.66 (s, 1H), 8.80 (d, J=2.20 Hz, 1H). LC/MS (ESI) mass calc. for C$_{20}$H$_{15}$ClF$_4$N$_6$O$_2$ 482.1, m/z found 483.1 [M+H]$^+$ Example 18

(*R)—N-(5-chloro-6-(tetrahydrofuran-2-yl)pyridin-3-yl)-1-(8-chloroimidazo[1,2-a]pyridin-5-yl)-5-(trifluoromethyl)-1H-pyrazole-4-carboxamide, cpd 18

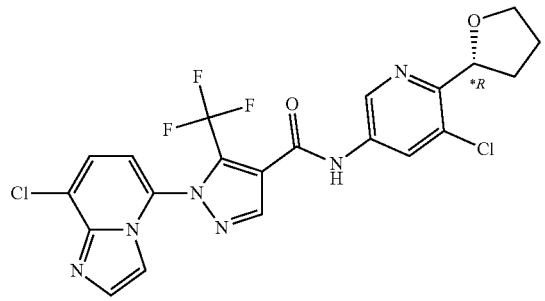 [SMILES: O=C(Nc1cnc([C@H]2CCCO2)c(Cl)c1)c1cnn(-c2ccc(Cl)c3nccn23)c1C(F)(F)F]

A. 3-Di-(tert-butyloxylcarbonyl)amino-5-chloropyridine, cpd 18a cpd 18a

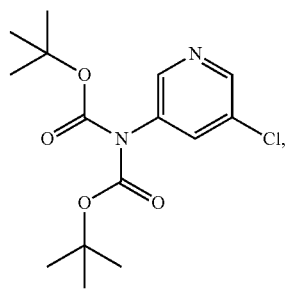

A mixture of 3-chloro-5-amino pyridine (5 g, 38.9 mmol) and DMAP (237.5 mg, 1.95 mmol) was stirred in THF (50 mL) at room temperature. BOC anhydride (21.2 g, 97.2 mmol) dissolved in THF was added dropwise. Stirring was continued for 16 h. Another 1.7 eq of BOC-anhydride was added. Stirring was continued for 16 h. The reaction mixture was concentrated under reduced pressure. The residue was stirred in di-isopropyl ether. The resultant precipitate was removed by filtration and dried to yield the title product (6.1 g, 47.7%). LC/MS (ESI) mass calc. for C$_{15}$H$_{21}$ClN$_2$O$_4$ 328.1, m/z found 329.2 [M+H]$^+$ B. 3-Di-(tert-butyloxylcarbonyl)-5-chloro-6-(tetrahydrofuran-2-yl)pyridine, cpd 18b cpd 18b

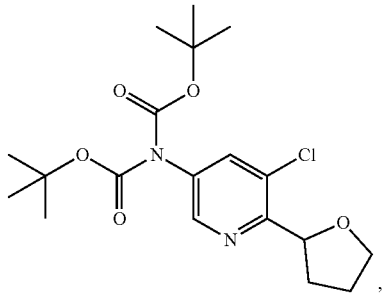

To 3-di-(tert-butyloxylcarbonyl)amino-5-chloropyridine (1 g, 3 mmol) in DMSO (30 mL) was added PTSA (392.8 mg, 2.28 mmol) and the mixture was stirred at room temperature for 15 min. THF (14.8 mL, 182.5 mmol), ammonium persulfate (3.47 g, 15 mmol) and (IR[DF(CF₃)PPY]₂(DTBPY))PF₆ (341.2 mg, 0.3 mmol) were added and the mixture was degassed for 10 min and sealed. The reaction mixture was stirred at room temperature under BLUE LED irradiation for 3 h. Water (50 mL) was added to the reaction mixture, and the aqueous layer was extracted with EtOAc (50 mL×2). The combined organic layers were dried over Na₂SO₄ and filtered. The filtrate was concentrated under reduced pressure. The crude product was purified by flash column chromatography over silica gel (eluent: petroleum ether/ethyl acetate ratio 100/0 to 86/14). The desired fractions were collected and the solvent concentrated under reduced pressure to give the title product (1 g, 83%) as a colorless oil. LC/MS (ESI) mass calc. for $C_{19}H_{27}ClN_2O_5$ 398.1, m/z found 399.0 [M+H]⁺

C.
5-Chloro-6-(tetrahydrofuran-2-yl)pyridin-3-amine, cpd 18c

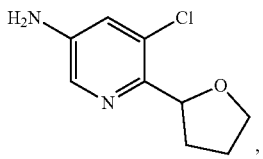

cpd 18c

To a solution of intermediate 3-di-(tert-butyloxylcarbonyl)-5-chloro-6-(tetrahydrofuran-2-yl)pyridine (3 g, 7.5 mmol) in DCM (10 mL) was added TFA (10 mL) at 0° C. The reaction mixture was stirred at 20° C. for 2 h. The mixture was added to aqueous NaHCO₃ (300 mL) solution and the aqueous layer was extracted with DCM (200 mL×3). The combined organic layers were dried over Na₂SO₄, filtered, and the filtrate was concentrated under reduced pressure. The crude product was purified by flash column chromatography over silica gel (eluent: petroleum ether/ethyl acetate gradient 100/0 to 25/75). The desired fractions were collected and the solvent was concentrated under reduced pressure to afford the title compound (1 g, 64.4%) as a white solid. LC/MS (ESI) mass calc. for $C_9H_{11}ClN_2O$ 198.1, m/z found 198.9 [M+H]⁺

D. (*R)-5-chloro-6-(tetrahydrofuran-2-yl)pyridin-3-amine, cpd 18c-1 and (*S)-5-chloro-6-(tetrahydrofuran-2-yl)pyridin-3-amine, cpd 18c-2

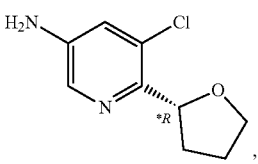

cpd 18c-1

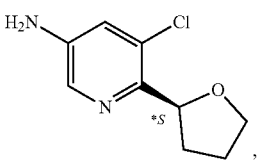

cpd 18c-2

5-Chloro-6-(tetrahydrofuran-2-yl)pyridin-3-amine, 18c (1 g, 4.84 mmol) was purified by SFC. Column: DAICEL CHIRALCEL OJ-H (250 mm×30 mm, 5um) Conditions: A: 0.1% NH₄OH in ETOH; B: EtOH; at the beginning: A (70%) and B (30%); at the end: A (70%) and B (30%). Flow Rate (50 mL/min). The desired fractions were collected and the solvent was concentrated under reduced pressure to yield (*R)-5-chloro-6-(tetrahydrofuran-2-yl)pyridin-3-amine, cpd 18c-1 (450 mg, 45.7%), LC/MS (ESI) mass calc. for $C_9H_{11}ClN_2O$ 198.1, m/z found 198.8 [M+H]⁺ and (*S)-5-chloro-6-(tetrahydrofuran-2-yl)pyridin-3-amine, cpd 18c-2 (450 mg, 45.7%), LC/MS (ESI) mass calc. for $C_9H_{11}ClN_2O$ 198.1, m/z found 198.8 [M+H]⁺ as white solids.

E. (*R)—N-(5-chloro-6-(tetrahydrofuran-2-yl)pyridin-3-yl)-1-(8-chloroimidazo[1,2-c]pyridin-5-yl)-5-(trifluoromethyl)-1H-pyrazole-4-carboxamide, cpd 18

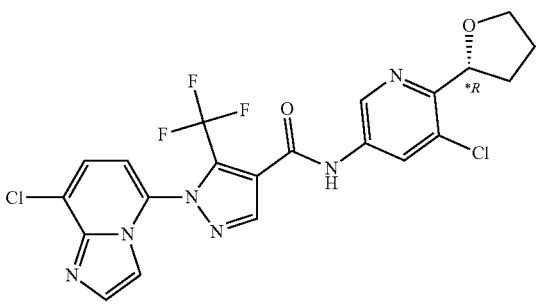 [SMILES: O=C(Nc1cnc([C@H]2CCCO2)c(Cl)c1)c1cnn(-c2ccc(Cl)c3nccn23)c1C(F)(F)F]

To a solution of 1-(8-chloroimidazo[1,2-a]pyridin-5-yl)-5-(trifluoromethyl)-1H-pyrazole-4-carboxylic acid (100 mg, 0.29 mmol) and pyridine (115.7 μL, 1.44 mmol) in DCM (4 mL) was added POCl₃ (54 μL, 0.58 mmol) at 20° C. The reaction mixture was stirred at 20° C. for 5 min. At this time, a solution of (*R)-5-chloro-6-(tetrahydrofuran-2-yl)pyridin-3-amine (58.65 mg, 0.29 mmol) in dichloromethane (2 mL) was added. The reaction mixture was stirred at 20° C. for 1 h. The reaction mixture was poured into sat. NaHCO₃ solution (20 mL). The reaction mixture was extracted with dichloromethane (50 mL×3). The combined organic layers were washed with brine, dried over Na₂SO₄ and filtered. The filtrate was concentrated under reduced pressure. The crude product was purified by preparative high-performance liquid chromatography. Column: Phenomenex Gemini 150×25 mm, 10 um; Conditions: A: (0.05% NH₄OH in CH₃CN; B: CH₃CN; at the beginning: A (60%) and B (40%); at the end: A (30%) and B (70%); Flow Rate (25 mL/min). The pure fractions were collected, the organic solvent was concentrated under reduced pressure and the residue lyophilized to dryness to give the title compound (98.6 mg, 66.8%) as a white solid. ¹H NMR (400 MHz, DMSO-d6) δ ppm 1.87-2.12 (m, 2H), 2.14-2.26 (m, 2H), 3.82 (br d, J=6.36 Hz, 1H), 3.89-3.98 (m, 1H), 5.26 (br t, J=6.72 Hz, 1H), 7.49 (br d, J=7.58 Hz, 1H), 7.54 (s, 1H), 7.74 (br d, J=7.58 Hz, 1H), 7.80 (s, 1H), 8.35 (br s, 1H), 8.68 (s, 1H), 8.76 (br s, 1H), 11.00 (br s, 1H). LC/MS (ESI) mass calc. for $C_{21}H_{15}Cl_2F_3N_6O_2$ 510.1, m/z found 511.1 [M+H]⁺

Following the procedures described in Examples 17 and 18, above, and selecting and substituting the appropriate reagents, starting materials, and purification methods, and adjusting reaction temperatures, times and other variables or parameters, as needed or desirable, as would be readily recognized by those skilled in the art, the following compounds (19-28) were prepared.

Example 19

(*R)—N-(5-chloro-6-(1-methoxyethyl)pyridin-3-yl)-1-(8-fluoroimidazo[1,2-a]pyridin-5-yl)-5-(trifluoromethyl)-1H-pyrazole-4-carboxamide, cpd 19

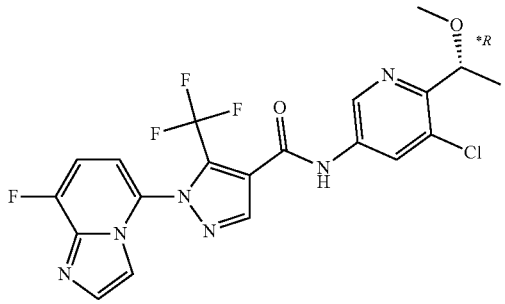 [SMILES: CO[C@H](C)c1ncc(NC(=O)c2cnn(-c3ccc(F)c4nccn34)c2C(F)(F)F)cc1Cl]

$^1$H NMR (400 MHz, DMSO-d6) δ ppm 1.42 (d, J=6.36 Hz, 3H), 3.17 (s, 3H), 4.83 (q, J=6.19 Hz, 1H), 7.39-7.57 (m, 3H), 7.78 (s, 1H), 8.37 (s, 1H), 8.66 (s, 1H), 8.80 (s, 1H), 11.00 (br s, 1H). LC/MS (ESI) mass calc. for $C_{20}H_{15}ClF_4N_6O_2$ 482.1, m/z found 483.1 [M+H]$^+$

Example 20

(*S)—N-(5-chloro-6-(tetrahydrofuran-2-yl)pyridin-3-yl)-1-(8-chloroimidazo[1,2-a]pyridin-5-yl)-5-(trifluoromethyl)-1H-pyrazole-4-carboxamide, cpd 20

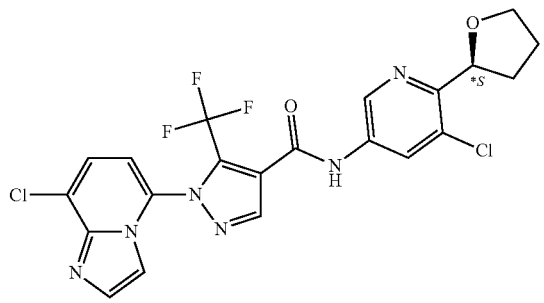 [SMILES: O=C(Nc1cnc([C@@H]2CCCO2)c(Cl)c1)c1cnn(-c2ccc(Cl)c3nccn23)c1C(F)(F)F]

$^1$H NMR (400 MHz, DMSO-d6) δ ppm 1.92-2.11 (m, 2H), 2.14-2.27 (m, 2H), 3.78-3.85 (m, 1H), 3.93 (q, J=7.11 Hz, 1H), 5.26 (t, J=6.90 Hz, 1H), 7.49 (d, J=7.78 Hz, 1H), 7.54 (d, J=1.00 Hz, 1H), 7.75 (d, J=7.78 Hz, 1H), 7.80 (d, J=1.00 Hz, 1H), 8.35 (d, J=2.01 Hz, 1H), 8.68 (s, 1H), 8.76 (d, J=2.26 Hz, 1H), 11.00 (br s, 1H). LC/MS (ESI) mass calc. for $C_{21}H_{15}Cl_2F_3N_6O_2$ 510.1, m/z found 511.1 [M+H]$^+$

Example 21

(*S)—N-(5-chloro-6-(tetrahydrofuran-2-yl)pyridin-3-yl)-1-(7-chloropyrazolo[1,5-a]pyridin-4-yl)-5-(trifluoromethyl)-1H-pyrazole-4-carboxamide, cpd 21

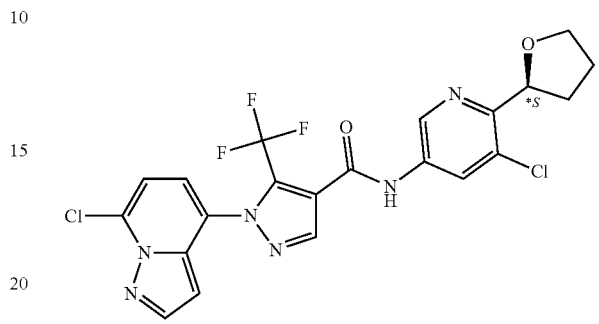

$^1$H NMR (400 MHz, DMSO-d6) δ ppm 1.87-1.97 (m, 1H), 1.99-2.07 (m, 1H), 2.12-2.22 (m, 2H), 3.75-3.82 (m, 1H), 3.89 (q, J=7.09 Hz, 1H), 5.23 (t, J=6.85 Hz, 1H), 6.53 (d, J=2.45 Hz, 1H), 7.42 (d, J=7.83 Hz, 1H), 7.63 (d, J=7.83 Hz, 1H), 8.26 (d, J=2.20 Hz, 1H), 8.31 (d, J=2.20 Hz, 1H), 8.50 (s, 1H), 8.72 (d, J=2.20 Hz, 1H), 10.96 (br s, 1H). LC/MS (ESI) mass calc. for $C_{21}H_{15}Cl_2F_3N_6O_2$ 510.1, m/z found 511.1 [M+H]$^+$

Example 22

(*R)—N-(5-chloro-6-(tetrahydrofuran-2-yl)pyridin-3-yl)-1-(7-chloropyrazolo[1,5-a]pyridin-4-yl)-5-(trifluoromethyl)-1H-pyrazole-4-carboxamide, cpd 22

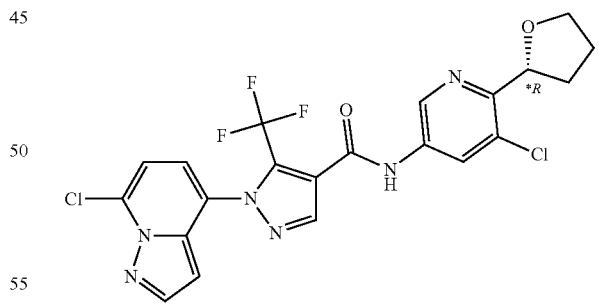

1H NMR (400 MHz, DMSO-d6) δ ppm 1.87-1.96 (m, 1H), 1.98-2.04 (m, 1H), 2.11-2.21 (m, 2H), 3.74-3.82 (m, 1H), 3.89 (q, J=7.17 Hz, 1H), 5.23 (t, J=6.85 Hz, 1H), 6.53 (d, J=2.20 Hz, 1H), 7.42 (d, J=7.83 Hz, 1H), 7.63 (d, J=7.83 Hz, 1H), 8.26 (d, J=2.20 Hz, 1H), 8.31 (d, J=1.96 Hz, 1H), 8.50 (s, 1H), 8.72 (d, J=1.96 Hz, 1H), 10.96 (s, 1H). LC/MS (ESI) mass calc. for $C_{21}H_{15}Cl_2F_3N_6O_2$ 510.1, m/z found 511.1 [M+H]$^+$

Example 23

(*S)—N-(5-chloro-6-(tetrahydrofuran-2-yl)pyridin-3-yl)-1-(7-cyanopyrazolo[1,5-a]pyridin-4-yl)-5-(trifluoromethyl)-1H-pyrazole-4-carboxamide, cpd 23

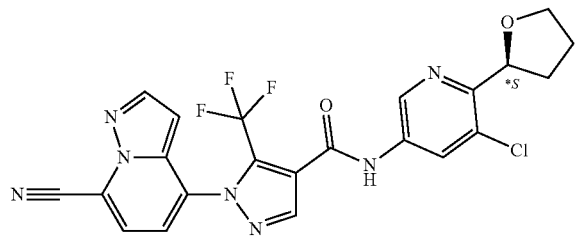 [SMILES: N#Cc1ccc(-n2ncc(C(=O)Nc3cnc([C@@H]4CCCO4)c(Cl)c3)c2C(F)(F)F)c2ccnn12]

$^1$H NMR (400 MHz, DMSO-d6) δ ppm 1.90-2.00 (1H, m), 2.02-2.11 (1H, m), 2.14-2.26 (2H, m), 3.77-3.86 (1H, m), 3.93 (1H, q, J=7.03 Hz), 5.27 (1H, t, J=6.90 Hz), 6.69 (1H, d, J=2.51 Hz), 7.77 (1H, d, J=7.53 Hz), 8.06 (1H, d, J=7.53 Hz), 8.35 (2H, t, J=2.51 Hz), 8.60 (1H, s), 8.76 (1H, d, J=2.26 Hz), 11.03 (1H, br s). LC/MS (ESI) mass calc. for $C_{22}H_{15}ClF_3N_7O_2$ 501.1, m/z found 502.1 [M+H]$^+$

Example 24

(*R)—N-(5-chloro-6-(tetrahydrofuran-2-yl)pyridin-3-yl)-1-(7-cyanopyrazolo[1,5-a]pyridin-4-yl)-5-(trifluoromethyl)-1H-pyrazole-4-carboxamide, cpd 24

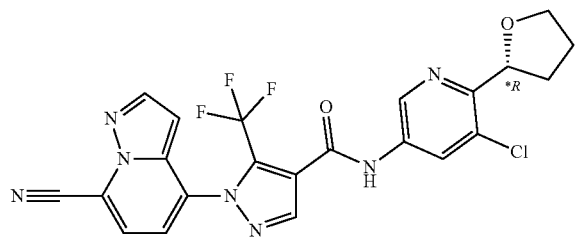

$^1$H NMR (400 MHz, DMSO-d6) δ ppm 1.87-1.97 (1H, m), 1.98-2.09 (1H, m), 2.11-2.23 (2H, m), 3.74-3.83 (1H, m), 3.90 (1H, q, J=7.25 Hz), 5.23 (1H, t, J=6.97 Hz), 6.65 (1H, d, J=2.45 Hz), 7.73 (1H, d, J=7.58 Hz), 8.02 (1H, d, J=7.83 Hz), 8.31 (2H, t, J=2.81 Hz), 8.55 (1H, s), 8.72 (1H, d, J=2.20 Hz), 10.99 (1H, br s). LC/MS (ESI) mass calc. for $C_{22}H_{15}ClF_3N_7O_2$ 501.1, m/z found 502.1 [M+H]$^+$

Example 25

(*S)—N-(5-chloro-6-(1-methoxyethyl)pyridin-3-yl)-1-(7-cyanopyrazolo[1,5-a]pyridin-4-yl)-5-(trifluoromethyl)-1H-pyrazole-4-carboxamide, cpd 25

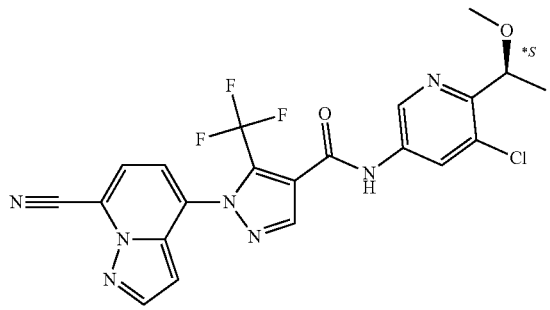 [SMILES: CO[C@@H](C)c1ncc(NC(=O)c2cnn(-c3ccc(C#N)n4nccc34)c2C(F)(F)F)cc1Cl]

$^1$H NMR (400 MHz, DMSO-d6) δ ppm 1.42 (3H, d, J=6.27 Hz), 3.17 (3H, s), 4.83 (1H, q, J=6.44 Hz), 6.69 (1H, d, J=2.26 Hz), 7.77 (1H, d, J=7.78 Hz), 8.06 (1H, d, J=7.53 Hz), 8.36 (2H, d, J=1.76 Hz), 8.59 (1H, s), 8.80 (1H, d, J=2.26 Hz), 11.03 (1H, br s). LC/MS (ESI) mass calc. for $C_{21}H_{15}ClF_3N_7O_2$ 489.1, m/z found 490.1 [M+H]$^+$

Example 26

(*R)—N-(5-chloro-6-(1-methoxyethyl)pyridin-3-yl)-1-(7-cyanopyrazolo[1,5-c]pyridin-4-yl)-5-(trifluoromethyl)-1H-pyrazole-4-carboxamide, cpd 26

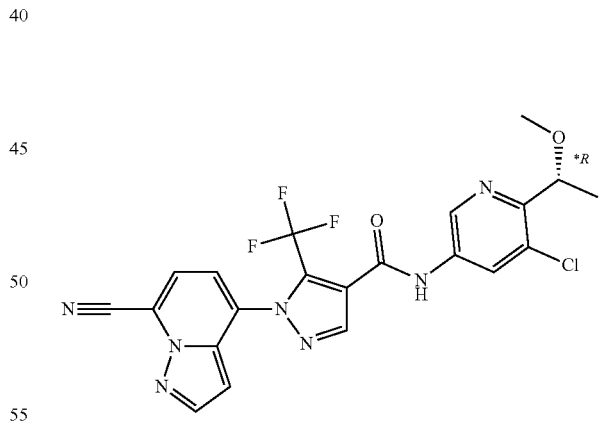

$^1$H NMR (400 MHz, DMSO-d6) δ ppm 1.39 (3H, d, J=6.36 Hz), 3.14 (3H, s), 4.79 (1H, q, J=6.52 Hz), 6.66 (1H, d, J=1.96 Hz), 7.74 (1H, d, J=7.83 Hz), 8.02 (1H, d, J=7.58 Hz), 8.32 (2H, s) 8.55 (1H, s), 8.77 (1H, s), 10.98 (1H, br s). LC/MS (ESI) mass calc. for $C_{21}H_{15}ClF_3N_7O_2$ 489.1, m/z found 490.1 [M+H]$^+$

Example 27

(*S)—N-(5-chloro-6-(1-methoxyethyl)pyridin-3-yl)-1-(7-chloropyrazolo[1,5-a]pyridin-4-yl)-5-(trifluoromethyl)-1H-pyrazole-4-carboxamide, cpd 27

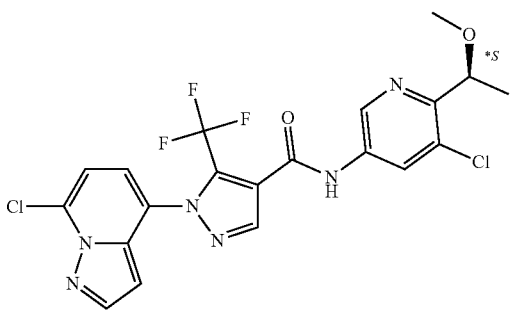 [SMILES: CO[C@@H](C)c1ncc(NC(=O)c2cnn(-c3ccc(Cl)n4nccc34)c2C(F)(F)F)cc1Cl]

$^1$H NMR (400 MHz, DMSO-d6) δ ppm 1.33-1.44 (m, 1H), 1.38 (d, J=6.36 Hz, 2H), 3.13 (s, 3H), 4.79 (q, J=6.52 Hz, 1H), 6.53 (s, 1H), 7.42 (d, J=7.83 Hz, 1H), 7.63 (d, J=7.83 Hz, 1H), 8.26 (s, 1H), 8.33 (s, 1H), 8.51 (s, 1H), 8.78 (s, 1H), 11.01 (br s, 1H). LC/MS (ESI) mass calc. for $C_{20}H_{15}Cl_2F_3N_6O_2$ 498.1, m/z found 499.0 [M+H]$^+$

Example 28

(*R)—N-(5-chloro-6-(1-methoxyethyl)pyridin-3-yl)-1-(7-chloropyrazolo[1,5-a]pyridin-4-yl)-5-(trifluoromethyl)-1H-pyrazole-4-carboxamide, cpd 28

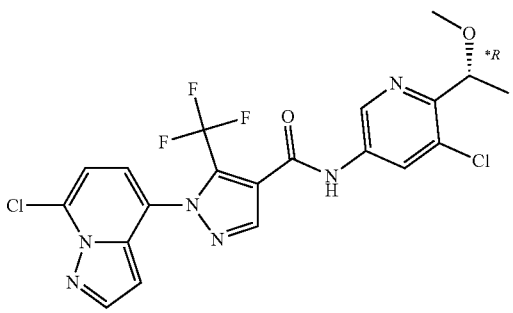 [SMILES: CO[C@H](C)c1ncc(NC(=O)c2cnn(-c3ccc(Cl)n4nccc34)c2C(F)(F)F)cc1Cl]

$^1$H NMR (400 MHz, DMSO-d6) δ ppm 1.38 (br d, J=6.36 Hz, 3H), 3.13 (s, 2H), 3.11-3.17 (m, 1H), 4.79 (br d, J=5.62 Hz, 1H), 6.53 (s, 1H), 7.42 (d, J=7.34 Hz, 1H), 7.63 (d, J=8.07 Hz, 1H), 8.26 (s, 1H), 8.33 (s, 1H), 8.52 (s, 1H), 8.78 (s, 1H), 11.01 (br s, 1H). LC/MS (ESI) mass calc. for $C_{20}H_{15}Cl_2F_3N_6O_2$ 498.1, m/z found 499.1 [M+H]$^+$

Example 29

N-(6-((dimethyl(oxo)-$\lambda^6$-sulfanylidene)amino)-5-methylpyridin-3-yl)-1-(8-fluoroimidazo[1,2-a]pyridin-5-yl)-5-(trifluoromethyl)-1H-pyrazole-4-carboxamide, cpd 29

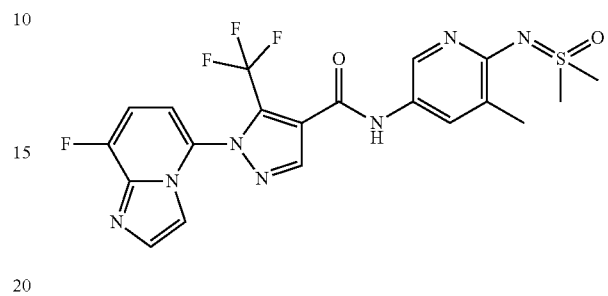

A. 3,6-difluoro-2-hydrazinylpyridine, cpd 29a

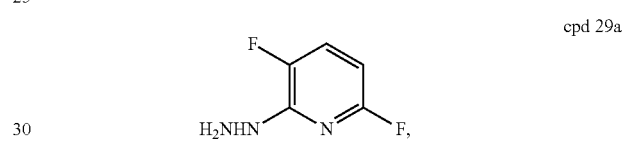

To an ice-cold solution of 2,3,6-trifluoropyridine (4 g, 30.06 mmol) in EtOH (50 mL) was added hydrazine hydrate (3.071 g, 60.12 mmol). The reaction mixture was warmed up to r.t. and then heated at reflux for 2 h. After it was cooled to r.t., the reaction mixture was diluted with water (50 mL) and extracted with CH$_2$Cl$_2$ (2×100 mL). The combined organic layers were dried over anhydrous Na$_2$SO$_4$, filtered, and the filtrate concentrated under reduced pressure. The residue was recrystallized from EtOH to obtain the product as a light yellow solid (3 g, yield: 68.8%).

B. 2-bromo-3,6-difluoropyridine, cpd 29b

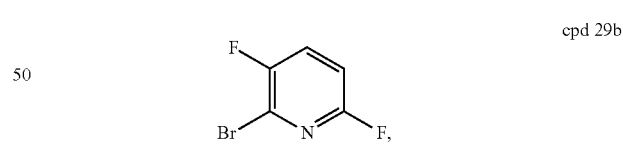

Br$_2$ (2.13 mL, 41.35 mmol) was added dropwise to a stirred solution of 3,6-difluoro-2-hydrazinylpyridine (3 g, 20.67 mmol) in CHCl$_3$ (45 mL) at room temperature. The mixture was stirred at 60° C. for 1 h. The mixture was cooled at 0° C. and a saturated solution of NaHCO$_3$(200 mL) was added dropwise. CH$_2$Cl$_2$ (200 mL) was added, the organic layer was separated, dried (Na$_2$SO$_4$), filtered and the solvents concentrated under reduced pressure. The residue was purified by flash column chromatography over silica gel (petroleum ether: EtOAc=1:0~9:1) to yield the product as a yellow oil (1.7 g, yield: 42.4%). $^1$H NMR (400 MHz, DMSO-d6) δ ppm 6.92 (td, J=3.1, 8.7 Hz, 1H), 7.55 (td, J=6.2, 8.6 Hz, 1H).

C. 2-Bromo-3-fluoro-6-hydrazinylpyridine, cpd 29c

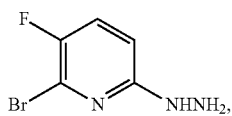

cpd 29c

2-Bromo-3,6-difluoropyridine (2.7 g, 13.92 mmol) was dissolved in MeCN (50 mL) and hydrazine hydrate (1.422 g, 27.84 mmol) was added. The reaction mixture was stirred at 80° C. for 16 h. The reaction mixture was concentrated under reduced pressure to afford crude as a yellow solid (2.868 g, yield:100%).

D. Ethyl 1-(6-bromo-5-fluoropyridin-2-yl)-5-(trifluoromethyl)-1H-pyrazole-4-carboxylate, cpd 29d

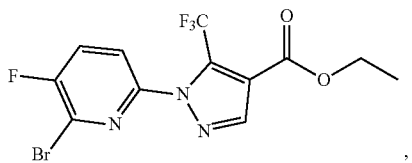

cpd 29d

2-Bromo-3-fluoro-6-hydrazinylpyridine (2.8 g, 13.59 mmol) was dissolved in EtOH (60 mL), ethyl 2-(ethoxymethylene)-4,4,4-trifluoro-3-oxobutanoate (6.529 g, 27.18 mmol) was added and stirred at 60° C. for 2 h. The mixture was concentrated under reduced pressure to afford crude product. The crude product was purified by flash column chromatography over silica gel (eluent: petroleum ether/ethyl acetate from 100/0 to 80/20). The desired fractions were collected and the solvent was concentrated under reduced pressure to afford compound as a yellow solid (2 g, yield: 38.5%). $^1$H NMR (400 MHz, DMSO-d6) δ ppm 1.38-1.41 (m, 3H), 4.37-4.41 (m, 2H), 7.63-7.67 (m, 2H), 8.11 (s, 1H).

E. Ethyl 1-(6-((tert-butoxycarbonyl)amino)-5-fluoropyridin-2-yl)-5-(trifluoromethyl)-1H-pyrazole-4-carboxylate, cpd 29e

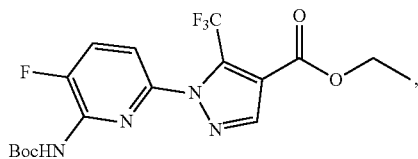

cpd 29e

Pd(OAc)$_2$ (58.755 mg, 0.26 mmol) and 4,5-bis(diphenylphosphino)-9,9-dimethylxanthene (151.428 mg, 0.26 mmol) in dioxane (50 mL) were stirred at rt for 10 min under nitrogen. Ethyl 1-(6-bromo-5-fluoropyridin-2-yl)-5-(trifluoromethyl)-1H-pyrazole-4-carboxylate (2 g, 5.23 mmol), Cs$_2$CO$_3$ (5.116 g, 15.70 mmol) and tert-butyl carbamate (0.736 g, 6.28 mmol) were then added at room temperature. The reaction mixture was then allowed to heat at 90° C. overnight and before cooling to rt. The reaction mixture was filtered through a pad of diatomaceous earth. The filtrate was concentrated under reduced pressure, then purified by flash column chromatography over silica gel (eluent: petroleum ether/EtOAc 100/0 to petroleum ether/EtOAc 80/20). The desired fractions were collected and the solvent was concentrated to dryness under reduced pressure to give the desired product as a yellow solid (1800 mg, yield: 82.2%).

F. ethyl 1-(6-amino-5-fluoropyridin-2-yl)-5-(trifluoromethyl)-1H-pyrazole-4-carboxylate, cpd 29f

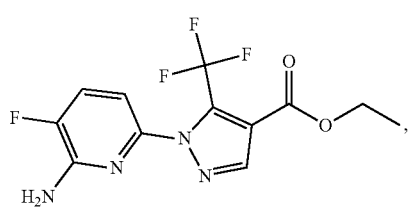

cpd 29f

Ethyl 1-(6-((tert-butoxycarbonyl)amino)-5-fluoropyridin-2-yl)-5-(trifluoromethyl)-1H-pyrazole-4-carboxylate (0.9 g, 2.15 mmol) and HCl/MeOH (18 mL, 4 M) were stirred at 30° C. for 1 h. The mixture was concentrated to dryness. To the residue was added saturated aqueous K$_2$CO$_3$ (50 mL). The mixture was extracted with EtOAc (50 mL×3). The combined organic layers were dried over Na$_2$SO$_4$, filtered and the filtrate was concentrated to dryness to give the product as an orange gum (650 mg, yield: 94.9%).

G. Ethyl 1-(8-fluoroimidazo[1,2-a]pyridin-5-yl)-5-(trifluoromethyl)-1H-pyrazole-4-carboxylate, cpd 29g

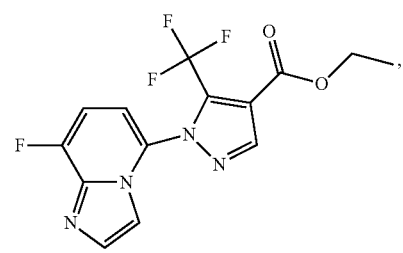

cpd 29g

Ethyl 1-(6-amino-5-fluoropyridin-2-yl)-5-(trifluoromethyl)-1H-pyrazole-4-carboxylate (650 mg, 2.043 mmol) was dissolved in EtOH (20 mL) under N$_2$. 2-Bromo-1,1-diethoxyethane (805.057 mg, 4.085 mmol) was added to the suspension followed by HBr (2 mL, 48% in water). The resulting mixture was then refluxed for 12 h and cooled to room temperature. The solvent was removed under reduced pressure. The residue was purified by flash column chromatography over silica gel (petroleum ether: ethyl acetate=10: 1~1:1). The pure fractions were collected and the solvent was concentrated under reduced pressure to afford the product as a light yellow solid (320 mg, yield: 45.8%). $^1$H NMR (400 MHz, CHLOROFORM-d) δ ppm 1.40 (t, J=7.2 Hz, 3H), 4.42 (q, J=7.1 Hz, 2H), 6.91 (dd, J=4.0, 7.9 Hz, 1H), 7.04 (dd, J=8.0, 9.4 Hz, 1H), 7.12 (s, 1H), 7.70 (s, 1H), 8.30 (s, 1H).

H. 1-(8-Fluoroimidazo[1,2-a]pyridin-5-yl)-5-(trifluoromethyl)-1H-pyrazole-4-carboxylic acid, cpd 29h

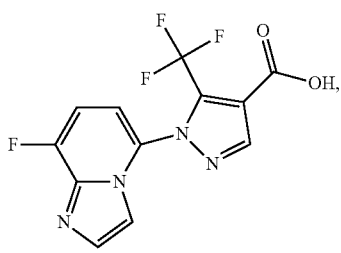

cpd 29h

The mixture of ethyl 1-(8-fluoroimidazo[1,2-a]pyridin-5-yl)-5-(trifluoromethyl)-1H-pyrazole-4-carboxylate (320 mg, 0.935 mmol) in concentrated HCl (6.064 mL) was stirred at 130° C. for 2 h. The solvent was concentrated under reduced pressure to afford the product as a yellow solid (300 mg, crude).

I. N-(6-bromo-5-methylpyridin-3-yl)acetamide, cpd 29i

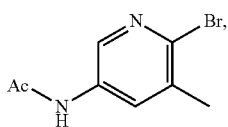

cpd 29i

A solution of 5-amino-2-bromo-3-methylpyridine (1 g, 5.35 mmol) in acetic anhydride (8 mL) was heated at 100° C. for 12h. The solution was evaporated until dryness. The residue was taken up in DCM. The organic layer was washed with a 10% aqueous solution of $K_2CO_3$, separated, dried over $MgSO_4$, filtered and evaporated to give a crude product (1.26 g, 100%). This compound was used directly in the next step without further purification.

J. N-(6-((dimethyl(oxo)-$\lambda^6$-sulfanylidene)amino)-5-methylpyridin-3-yl)acetamide, cpd 29j

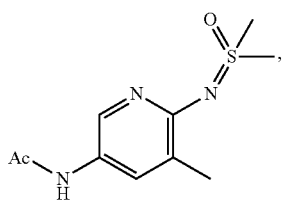

cpd 29j

A mixture of N-(6-bromo-5-methylpyridin-3-yl)acetamide (0.7 g, 3.06 mmol), S,S-dimethylsulfoximine (0.28 g, 3.06 mmol), Xantphos (0.19 g, 0.33 mmol) and cesium carbonate (2.98 g, 9.17 mmol) in F (5 mL) was degassed with a stream of $N_2$ for 30 min. $Pd_2(dba)_3$ (0.14 g, 0.15 mmol) was added and the mixture was heated at 100° C. overnight in a sealed tube. The mixture was poured out into water and filtered through a Celite® layer. The organic layer was extracted with $CH_2Cl_2$, separated, dried over $MgSO_4$, filtered and concentrated to dryness to afford crude product as a brown oil. The crude product was purified via preparative LC (Stationary phase: regular SiOH 15 µm 25 g Interchim, Mobile phase: gradient from 100% DCM to 95/5 DCM/MeOH). The pure fractions were collected and solvent evaporated until dryness to give the product (0.56 g, 76%). LC-MS: (ES, m/z): $[M+1]^+$ 242.3

K. ((5-Amino-3-methylpyridin-2-yl)imino)dimethyl-$\lambda^6$-sulfanone, cpd 29k

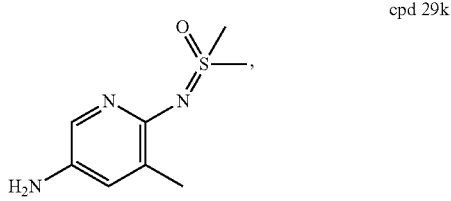

cpd 29k

A mixture of N-(6-((dimethyl(oxo)-$\lambda^6$-sulfanylidene)amino)-5-methylpyridin-3-yl)acetamide (0.56 g, 2.32 mmol) and potassium hydroxide (0.45 g, 6.96 mmol) in EtOH (10 mL) was refluxed for 6h. The solution was poured into cooled water and the product was extracted with $CH_2Cl_2$. The organic layer was washed with an aqueous solution of $K_2CO_3$ 10%, separated, dried over $MgSO_4$ and filtered. The solvent was evaporated to dryness to give the compound which was used in the next step without purification.

L. N-(6-((dimethyl(oxo)-$\lambda^6$-sulfanylidene)amino)-5-methylpyridin-3-yl)-1-(8-fluoroimidazo[1,2-a]pyridin-5-yl)-5-(trifluoromethyl)-1H-pyrazole-4-carboxamide, cpd 29

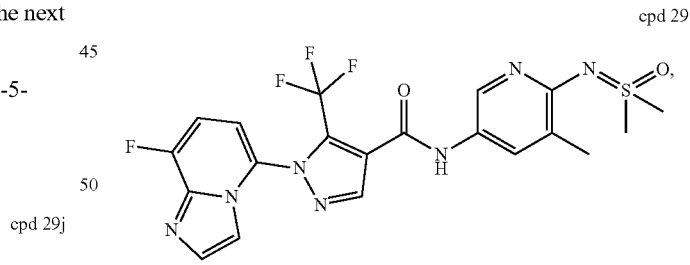

cpd 29

A solution of 1-(8-fluoroimidazo[1,2-a]pyridin-5-yl)-5-(trifluoromethyl)-1H-pyrazole-4-carboxylic acid (0.1 g, 0.32 mmol), ((5-amino-3-methylpyridin-2-yl)imino)dimethyl-$\lambda^6$-sulfanone (0.06 g, 0.32 mmol), HATU (0.14 g, 0.38 mmol) and DIPEA (0.08 mL, 0.48 mmol) in DMF (6 mL) was stirred at room temperature for 12h. The mixture was poured out into iced water. EtOAc was added and the organic layer was separated, washed with a 10% aqueous solution of $K_2CO_3$, dried over $MgSO_4$ and filtered. The solvent was evaporated to give a crude product as a brown oil. This crude was purified via preparative LC (Stationary phase: regular SiOH 15 µm 25 g Interchim, Mobile phase: gradient from 100% DCM to 95/5 DCM/MeOH). The pure fractions were collected and solvent evaporated until dryness. The residue was taken up in DIPE. The solid was filtered and dried to afford the product (91 mg, 57.7%). $^1$H NMR (400 MHz, DMSO-d6) δ ppm 2.15 (s, 3H), 3.37 (s, 6H), 7.41-7.46 (m, 2H), 7.47-7.49 (m, 1H), 7.76 (d, J=2.21 Hz, 1H), 7.77-7.78 (m, 1H), 8.23 (d, J=2.21 Hz, 1H), 10.38 (s, 1H). LC-MS: (ES, m/z): [M+1]$^+$ 496.2

Example 30

N-(6-(((dimethyl(oxo)-λ$^6$-sulfanylidene)amino)-5-(trifluoromethyl)pyridin-3-yl)-1-(8-fluoroimidazo[1,2-a]pyridin-5-yl)-5-(trifluoromethyl)-1H-pyrazole-4-carb oxamide, cpd 30

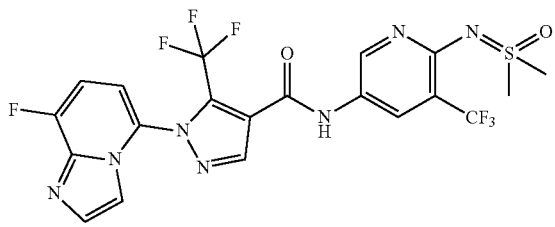 [SMILES: CS(C)(=O)=Nc1ncc(NC(=O)c2cnn(-c3ccc(F)c4nccn34)c2C(F)(F)F)cc1C(F)(F)F]

A. N-(6-chloro-5-(trifluoromethyl)-3-pyridyl)acetamide, cpd 30a

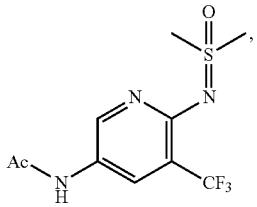

A solution of 6-chloro-5-(trifluoromethyl)pyridin-3-amine (0.35 g, 1.78 mmol) in acetic anhydride (6 mL) was heated at 100° C. for 12h. The solution was evaporated until dryness. The residue was taken up in DCM. The organic layer was washed with a 10% aqueous solution of K$_2$CO$_3$, separated, dried over MgSO$_4$, filtered and evaporated to give a crude product (0.44 g, 100%). This compound was used directly in the next step without further purification.

B. N-(6-(((dimethyl(oxo)-λ$^6$-sulfanylidene)amino)-5-(trifluoromethyl)-3-pyridyl)acetamide, cpd 30b

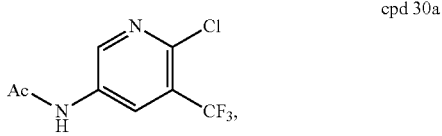 [SMILES: CC(=O)Nc1cnc(Cl)c(C(F)(F)F)c1]

A mixture of N-(6-chloro-5-(trifluoromethyl)-3-pyridyl) acetamide (0.4 g, 1.68 mmol), S,S-dimethylsulfoximine (0.156 g, 1.68 mmol), Xantphos (0.107 g, 0.18 mmol) and cesium carbonate (1.6 g, 5.03 mmol) in dioxane (6 mL) was degassed with a stream of N$_2$ for 30 min. Pd$_2$(dba)$_3$ (0.08 g, 0.08 mmol) was added and the mixture was heated at 100° C. overnight in a sealed tube. The mixture was poured out into water and filtered through a Celite® layer. The organic layer was extracted with CH$_2$Cl$_2$, separated, dried over MgSO$_4$, filtered and concentrated to dryness to afford crude product as a brown oil. The crude product was purified via preparative LC (Stationary phase: regular SiOH 15 μm 25 g Interchim, Mobile phase: gradient from 100% DCM to 95/5 DCM/MeOH). The pure fractions were collected and solvent evaporated until dryness to give the product (0.21 g, 42%). $^1$H NMR (400 MHz, DMSO-d6) δ ppm 2.04 (s, 3H), 3.32 (s, 6H), 8.19 (d, J=2.6 Hz, 1H), 8.43 (d, J=2.5 Hz, 1H), 10.07 (s, 1H).

C. ((5-amino-3-methylpyridin-2-yl)imino)dimethyl-λ$^6$-sulfanone, cpd 30c

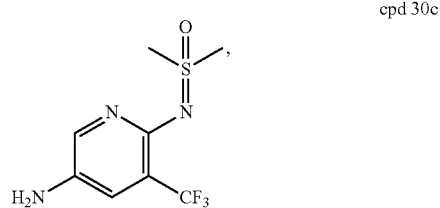

A mixture of N-(6-(((dimethyl(oxo)-λ$^6$-sulfanylidene) amino)-5-(trifluoromethyl)-3-pyridyl)acetamide (0.2 g, 0.7 mmol) and potassium hydroxide (0.14 g, 2.1 mmol) in EtOH (8 mL) was heated to reflux for 6h. The solution was poured into cooled water and the product was extracted with CH$_2$Cl$_2$. The organic layer was washed with an aqueous solution of K$_2$CO$_3$ 10%, separated, dried over MgSO$_4$ and filtered. The solvent was evaporated to dryness to give a crude product (0.18 g, 100%). $^1$H NMR (400 MHz, DMSO-d6) δ ppm 3.31 (s, 6H), 5.00 (s, 2H), 7.19 (d, J=2.8 Hz, 1H), 7.76 (d, J=2.5 Hz, 1H).

D. N-(6-(((dimethyl(oxo)-λ$^6$-sulfanylidene)amino)-5-(trifluoromethyl)pyridin-3-yl)-1-(8-fluoroimidazo[1,2-a]pyridin-5-yl)-5-(trifluoromethyl)-1H-pyrazole-4-carboxamide, cpd 30

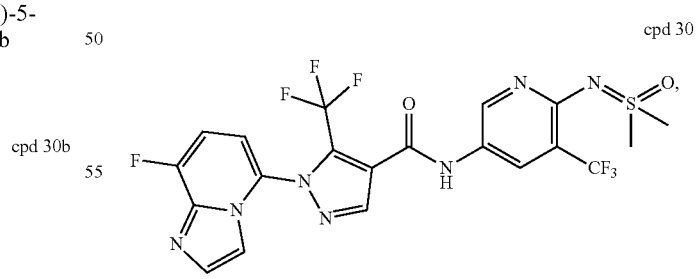

A solution of 1-(8-Fluoroimidazo[1,2-a]pyridin-5-yl)-5-(trifluoromethyl)-1H-pyrazole-4-carboxylic acid (0.15 g, 0.47 mmol), ((5-amino-3-methylpyridin-2-yl)imino)dimethyl-λ$^6$-sulfanone (0.12 g, 0.47 mmol), HATU (0.21 g, 0.56 mmol) and DIPEA (0.12 mL, 0.71 mmol) in DMF (5 mL) was stirred at room temperature for 12h. The mixture was poured out into iced water. EtOAc was added and the organic layer was separated, washed with a 10% aqueous solution of $K_2CO_3$, dried over $MgSO_4$ and filtered. The solvent was evaporated to give a crude product as a brown oil. This crude was purified via preparative LC (Stationary phase: regular SiOH 15 μm 25 g Interchim, Mobile phase: gradient from 100% DCM to 95/5 DCM/MeOH). The pure fractions were collected and solvent evaporated until dryness. The residue (0.2 g) was taken up in DIPE. The solid was filtered and dried to afford a product (150 mg). This product was taken up in DCM. The solution was washed with a 10% aqueous solution of $K_2CO_3$. The organic layer was separated, dried over $MgSO_4$, filtered and the solvent was evaporated to dryness. The residue was taken up in DIPE. The solid was filtered and dried to give expected compound (0.092 g, 36%). 41 NMR (400 MHz, DMSO-$d_6$) δ ppm 3.44 (s, 6H), 7.42-7.54 (m, 3H), 7.78 (s, 1H), 8.30 (d, J=2.2 Hz, 1H), 8.64 (br s, 2H), 10.73 (s, 1H). LC-MS: (ES, m/z): [M+1]$^+$ 550.3

Example 31

1-(8-fluoroimidazo[1,2-a]pyridin-5-yl)-N-(6-(S-methylsulfonimidoyl)-5-(trifluoromethyl)pyridin-3-yl)-5-(trifluoromethyl)-1H-pyrazole-4-carboxamide, cpd 31

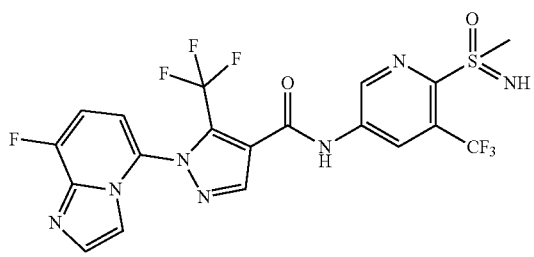 [SMILES: CS(=N)(=O)c1ncc(NC(=O)c2cnn(-c3ccc(F)c4nccn34)c2C(F)(F)F)cc1C(F)(F)F]

A. 2-methylsulfanyl-5-nitro-3-(trifluoromethyl)pyridine, cpd 31a

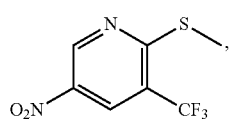

A solution of 2-chloro-5-nitro-3-(trifluoromethyl)pyridine (1 g, 4.41 mmol) and sodiumthiomethoxide (0.31 g, 4.41 mmol) in DMF (10 mL) was stirred at room temperature for 12h. The mixture was poured into water. The organic layer was extracted with $CH_2Cl_2$, separated, dried over $MgSO_4$, filtered and concentrated to dryness to give the compound (1.1 g, 100%). This compound was used directly in the next step without any further purification.

B. 6-methylsulfanyl-5-(trifluoromethyl)pyridin-3-amine, cpd 31b

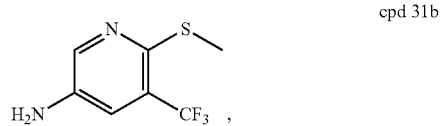

A mixture of 2-methylsulfanyl-5-nitro-3-(trifluoromethyl)pyridine (0.5 g, 2.1 mmol) and Raney Nickel (0.5 g) in EtOH (15 mL) was hydrogenated in a Parr reactor (3 atmospheres) for 3h at room temperature. The catalyst was filtered off on a pad of Celite®, washed with $CH_2Cl_2$ and the filtrate was concentrated to dryness. The residue was purified via preparative LC (Stationary phase: regular SiOH 15 μm 25 g Interchim, Mobile phase:gradient from 100% DCM to 95/5 DCM/MeOH). The fraction was collected and solvent evaporated until dryness to give the compound (0.18, 41%). LC-MS: (ES, m/z): [M+1]$^+$ 209.2

C. 1-(8-fluoroimidazo[1,2-a]pyridin-5-yl)-N-[6-methylsulfanyl-5-(trifluoromethyl)-3-pyridyl]-5-(trifluoromethyl)pyrazole-4-carboxamide, cpd 31c

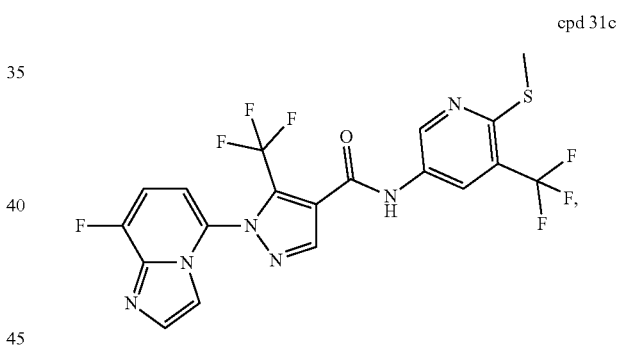

A solution of 1-(8-Fluoroimidazo[1,2-a]pyridin-5-yl)-5-(trifluoromethyl)-1H-pyrazole-4-carboxylic acid (0.245 g, 0.768 mmol), 6-methylsulfanyl-5-(trifluoromethyl)pyridin-3-amine (0.16 g, 0.768 mmol), HATU (0.35 g, 0.922 mmol) and DIPEA (0.2 mL, 1.15 mmol) in DMF (8 mL) was stirred at room temperature for 12h. The mixture was poured out into ice water. EtOAc was added and the organic layer was separated, washed with a 10% aqueous solution of $K_2CO_3$, dried over $MgSO_4$, filtered and the solvent was evaporated to dryness. The residue was purified via preparative LC (Stationary phase: regular SiOH 15 μm 25 g Interchim, Mobile phase:gradient from 100% DCM to 95/5 DCM/MeOH). The fraction was collected and solvent evaporated until dryness to give the compound (0.27 g, 70%). $^1$H NMR (500 MHz, DMSO-$d_6$) δ ppm 2.61 (s, 3H), 7.26-7.56 (m, 3H), 7.78 (s, 1H), 8.48 (d, J=1.6 Hz, 1H), 8.66 (s, 1H), 9.03 (s, 1H), 10.98 (s, 1H). LC-MS: (ES, m/z): [M+1]$^+$ 505.5

107

D. 1-(8-fluoroimidazo[1,2-a]pyridin-5-yl)-N-(6-(S-methylsulfonimidoyl)-5-(trifluoromethyl)pyridin-3-yl)-5-(trifluoromethyl)-1H-pyrazole-4-carboxamide, cpd 31

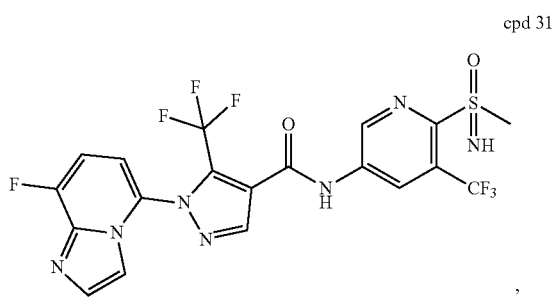 [SMILES: CS(=N)(=O)c1ncc(NC(=O)c2cnn(-c3ccc(F)c4nccn34)c2C(F)(F)F)cc1C(F)(F)F]

cpd 31

A solution of 1-(8-fluoroimidazo[1,2-a]pyridin-5-yl)-N-[6-methylsulfanyl-5-(trifluoromethyl)-3-pyridyl]-5-(trifluoromethyl)pyrazole-4-carboxamide (0.27 g, 0.535 mmol), iodobenzenediacetate (0.43 g, 1.34 mmol) and ammonium carbamate (0.167 g, 2.14 mmol) in MeOH (7 mL) was stirring at room temperature for 12h. The organic layer was extracted with AcOEt, separated, dried over MgSO$_4$, filtered and evaporated until dryness. The residue was purified via preparative LC (Stationary phase: regular SiOH 15 μm 25 g Interchim, Mobile phase:gradient from 100% DCM to 95/5 DCM/MeOH). The fraction was collected and solvent evaporated until dryness. The residue (0.2 g) was taken up in DIPE. The solid was filtered and dried to give the compound (0.1 g, 35%). $^1$H NMR (400 MHz, DMSO-d$_6$) δ 4.57 (s, 1H), 7.43-7.58 (m, 3H), 7.79 (s, 1H), 8.71 (s, 1H), 8.76 (s, 1H), 9.18 (s, 1H), 11.38 (s, 1H). LC-MS: (ES, m/z): [M+1]$^+$ 536.5

Example 32

N-(6-((dimethyl(oxo)-λ$^6$-sulfanylidene)amino)-5-fluoropyridin-3-yl)-1-(8-fluoroimidazo[1,2-a]pyridin-5-yl)-5-(trifluoromethyl)-1H-pyrazole-4-carboxamide, cpd 32

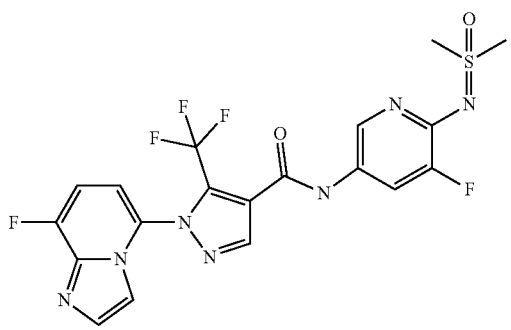 [SMILES: CS(C)(=O)=Nc1ncc(NC(=O)c2cnn(-c3ccc(F)c4nccn34)c2C(F)(F)F)cc1F]

108

A. tert-butyl N-(6-chloro-5-fluoro-3-pyridyl)carbamate, cpd 32a

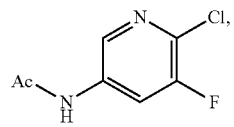

cpd 32a

A solution of 6-chloro-5-fluoropyridin-3-amine (0.8 g, 5.46 mmol) in acetic anhydride (7 mL) was heated at 100° C. for 12 h. The solution was evaporated until dryness. The residue was taken up in DCM. The organic layer was washed with a 10% aqueous solution of K$_2$CO$_3$, separated, dried over MgSO$_4$, filtered and evaporated under vacuo. The residue was purified via preparative LC (Stationary phase: regular SiOH 15 μm 25 g Interchim, Mobile phase: gradient from 100% DCM to 95/5 DCM/MeOH). The fraction was collected and solvent evaporated until dryness to give the product (0.44 g, 43%). $^1$H NMR (500 MHz, DMSO-d$_6$) δ ppm 2.10 (s, 3H), 8.19 (dd, J=10.72, 2.21 Hz, 1H), 8.37 (d, J=2.21 Hz, 1H), 10.51 (br s, 1H)

B. N-(6-((dimethyl(oxo)-λ$^6$-sulfaneylidene)amino)-5-fluoro-3-pyridyl)acetamide, cpd 32b

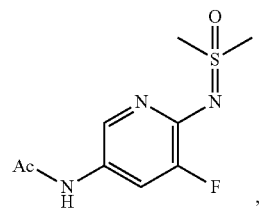

cpd 32b

A mixture of tert-butyl N-(6-chloro-5-fluoro-3-pyridyl)carbamate (0.44 g, 2.34 mmol), S,S-dimethylsulfoximine (0.22 g, 2.34 mmol), Xantphos (0.15 g, 0.26 mmol) and cesium carbonate (2.3 g, 7.02 mmol) in dioxane (5 mL) was degassed with a stream of N$_2$ for 30 min. Pd$_2$(dba)$_3$ (0.11 g, 0.12 mmol) was added and the mixture was heated at 100° C. overnight in a sealed tube. The mixture was poured out into water and filtered through a Celite® layer. The organic layer was extracted with CH$_2$Cl$_2$, separated, dried over MgSO$_4$, filtered and concentrated to dryness to afford crude product as a brown oil. The crude product was purified via preparative LC (Stationary phase: regular SiOH 15 μm 25 g Interchim, Mobile phase: gradient from 100% DCM to 95/5 DCM/MeOH). The pure fractions were collected and solvent evaporated until dryness to give the product (0.35 g, 61%). $^1$H NMR (500 MHz, DMSO-d$_6$) δ ppm 1.99-2.05 (m, 3H), 3.24-3.30 (m, 6H), 7.79 (dd, J=12.45, 2.05 Hz, 1H), 8.04 (d, J=1.89 Hz, 1H), 9.98 (s, 1H)

E. 6-[[dimethyl(oxo)-λ⁶-sulfanylidene]amino]-5-fluoro-pyridin-3-amine, cpd 32c

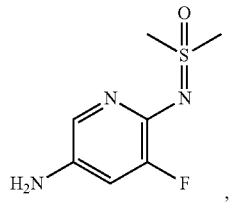

cpd 32c

A mixture of N-(6-((dimethyl(oxo)-λ⁶-sulfaneylidene) amino)-5-fluoro-3-pyridyl)acetamide (0.35 g, 1.43 mmol) and potassium hydroxide (0.28 g, 4.3 mmol) in EtOH (10 mL) was refluxed for 6 h. The solution was poured into cooled water and the product was extracted with $CH_2Cl_2$. The organic layer was washed with a 10% aqueous solution of $K_2CO_3$, separated, dried over $MgSO_4$ and filtered. The solvent was evaporated to dryness to give a crude product (0.2 g, 69%). This compound was used directly in the next step without any further purification. a N-(6-((dimethyl(oxo)-λ⁶-sulfanylidene)amino)-5-fluoropyridin-3-yl)-1-(8-fluoroimidazo[1,2-a]pyridin-5-yl)-5-(trifluoromethyl)-1H-pyrazole-4-carboxamide, cpd 32

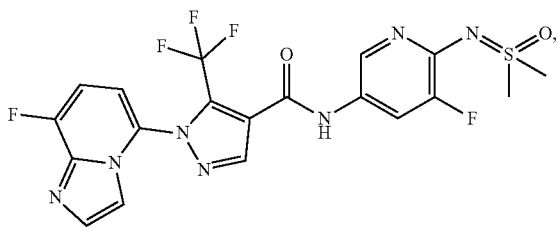

cpd 32

A solution of 1-(8-Fluoroimidazo[1,2-a]pyridin-5-yl)-5-(trifluoromethyl)-1H-pyrazole-4-carboxylic acid (0.14 g, 0.42 mmol), 6-[[dimethyl(oxo)-λ⁶-sulfanylidene]amino]-5-fluoro-pyridin-3-amine (0.09 g, 0.42 mmol), HATU (0.19 g, 0.51 mmol) and DIPEA (0.11 mL, 0.63 mmol) in DMF (6 mL) was stirred at room temperature for 12 h. The mixture was poured out into iced water. EtOAc was added and the organic layer was separated, washed with a 10% aqueous solution of $K_2CO_3$, dried over $MgSO_4$ and filtered. The solvent was evaporated to give a crude product as a brown oil. This crude was purified via preparative LC (Stationary phase: regular SiOH 15 µm 25 g Interchim, Mobile phase: gradient from 100% DCM to 95/5 DCM/MeOH). The pure fractions were collected and solvent evaporated until dryness. The residue was taken up in DIPE. The solid was filtered and dried to afford a product (58 mg, 27%). ¹H NMR (500 MHz, DMSO-d₆) δ ppm 3.43 (s, 6H), 7.41-7.50 (m, 3H), 7.77 (s, 1H), 7.89 (dd, J=11.98, 1.89 Hz, 1H), 8.23 (d, J=1.89 Hz, 1H), 8.61 (s, 1H), 10.65 (s, 1H). LC-MS: (ES, m/z): [M+1]⁺ 500.2

Example 33

N-(5-chloro-6-((dimethyl(oxo)-λ⁶-sulfanylidene) amino)pyridin-3-yl)-1-(8-fluoroimidazo[1,2-a]pyridin-5-yl)-5-(trifluoromethyl)-1H-pyrazole-4-carboxamide, cpd 33

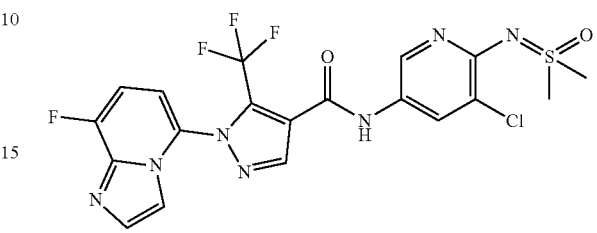

A. N-(5,6-dichloro-3-pyridyl)acetamide, cpd 33a

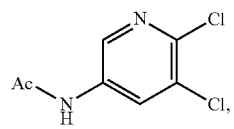

cpd 33a

A solution of 3-amino-5,6-dichloropyridine (1 g, 6.1 mmol) in acetic anhydride (8 mL) was heated at 100° C. for 12h. The solution was evaporated until dryness. The residue was taken up in DCM. The organic layer was washed with a 10% aqueous solution of $K_2CO_3$, separated, dried over $MgSO_4$, filtered and evaporated to give a crude product (1.3 g). This compound was used directly in the next step without further purification.

B. N-[5-chloro-6-[[dimethyl(oxo)-λ⁶-sulfanylidene]amino]-3-pyridyl]acetamide, cpd 33b

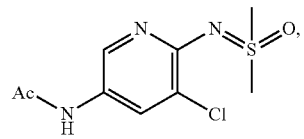

cpd 33b

A mixture of N-(5,6-dichloro-3-pyridyl)acetamide (0.7 g, 3.41 mmol), S,S-dimethylsulfoximine (0.32 g, 3.4 mmol), Xantphos (0.22 g, 0.38 mmol) and cesium carbonate (3.3 g, 10.2 mmol) in dioxane (10 mL) was degassed with a stream of $N_2$ for 30 min. $Pd_2(dba)_3$ (0.08 g, 0.08 mmol) was added and the mixture was heated at 100° C. overnight in a sealed tube. The mixture was poured out into water and filtered through a Celite® layer. The organic layer was extracted with $CH_2Cl_2$, separated, dried over $MgSO_4$, filtered and concentrated to dryness to afford crude product as a brown oil. The crude product was purified via preparative LC (Stationary phase: regular SiOH 15 µm 25 g Interchim, Mobile phase: gradient from 100% DCM to 95/5 DCM/MeOH). The pure fractions were collected and solvent evaporated until dryness to give the product (0.56 g, 63%).

¹H NMR (500 MHz, DMSO-d₆) δ 2.02 (s, 3H), 3.38 (s, 6H), 8.01 (d, J=2.52 Hz, 1H), 8.16 (d, J=2.52 Hz, 1H), 9.94 (s, 1H).

C. 5-chloro-6-[[dimethyl(oxo)-λ⁶-sulfanylidene]amino]pyridin-3-amine, cpd 33c

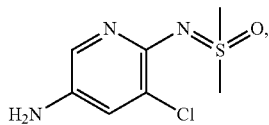

cpd 33c

A mixture of N-[5-chloro-6-[[dimethyl(oxo)-λ⁶-sulfanylidene]amino]-3-pyridyl]acetamide (0.56 g, 2.14 mmol) and potassium hydroxide (0.423 g, 6.4 mmol) in EtOH (10 mL) was heated to reflux for 6 h. The solution was poured into cooled water and the product was extracted with CH₂Cl₂. The organic layer was washed with an aqueous solution of K₂CO₃ 10%, separated, dried over MgSO₄ and filtered. The solvent was evaporated to dryness to give a crude product (0.44 g). This compound was used directly in the next step without further purification.

D. N-(5-chloro-6-((dimethyl(oxo)-λ⁶-sulfanylidene)amino)pyridin-3-yl)-1-(8-fluoroimidazo[1,2-a]pyridin-5-yl)-5-(trifluoromethyl)-1H-pyrazole-4-carboxamide, cpd 33

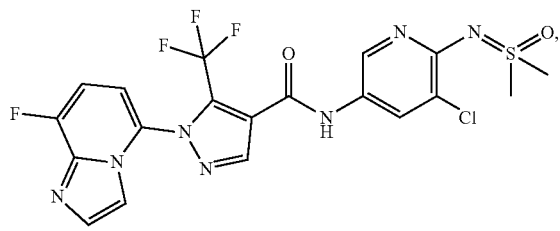

cpd 33

A solution of 1-(8-fluoroimidazo[1,2-a]pyridin-5-yl)-5-(trifluoromethyl)-1H-pyrazole-4-carboxylic acid (0.12 g, 0.37 mmol), 5-chloro-6-[[dimethyl(oxo)-λ⁶-sulfanylidene]amino]pyridin-3-amine (0.083 g, 0.37 mmol), HATU (0.17 g, 0.45 mmol) and DIPEA (0.097 mL, 0.56 mmol) in DMF (6 mL) was stirred at room temperature for 12h. The mixture was poured out into iced water. EtOAc was added and the organic layer was separated, washed with a 10% aqueous solution of K₂CO₃, dried over MgSO₄ and filtered. The solvent was evaporated to give a crude product as a brown oil. This crude was purified via preparative LC (Stationary phase: regular SiOH 15 μm 25 g Interchim, Mobile phase: gradient from 100% DCM to 95/5 DCM/MeOH). The pure fractions were collected and solvent evaporated until dryness. The residue was purified via Reverse phase (Stationary phase: YMC-actus Triart C18 10 μm 30*150 mm, Mobile phase: Gradient from 75% NH₄HCO₃ 0.2%, 25% ACN to 35% NH₄HCO₃ 0.2%, 65% ACN). The fraction was collected and solvent evaporated until dryness. The residue was taken up in DIPE. The solid was filtered and dried to give the compound (0.053 g, 27%). ¹H NMR (500 MHz, DMSO-d₆) δ 3.43 (br s, 6H), 7.36-7.56 (m, 3H), 7.77 (br s, 1H), 8.13 (br s, 1H), 8.35 (br s, 1H), 8.61 (br s, 1H), 10.61 (br s, 1H). LC-MS: (ES, m/z): [M+1]⁺ 516.2

BIOLOGICAL EXAMPLES

In vitro assays include assays that determine cell morphology, protein expression, and/or the cytotoxicity, enzyme inhibitory activity, and/or the subsequent functional consequences of treatment of cells with compounds of the invention. Alternate or additional in vitro assays may be used to quantitate the ability of the inhibitor to bind to protein or nucleic acid molecules within the cell.

Inhibitor binding may be measured by radiolabelling the inhibitor prior to binding, isolating the inhibitor/target molecule complex and determining the amount of radiolabel bound. Alternatively or additionally, inhibitor binding may be determined by running a competition experiment where new inhibitors are incubated with purified proteins or nucleic acids bound to known radioligands. Detailed conditions of exemplary systems for assaying a compound of Formula (I) of the present invention as MALT1 inhibitors are set forth in the Biological Examples below.

Such assays are exemplary and not intended to limit the scope of the invention. The skilled practitioner can appreciate that modifications can be made to conventional assays to develop equivalent or other assays that can be employed to comparably assess activity or otherwise characterize compounds and/or compositions as described herein.

In Vitro Assays

Biological Example 1

MALT1 Biochemical Protease Assay

MALT1 protease activity was assessed in an in vitro assay using a tetrapeptide as substrate and full-length MALT1 protein (Strep-MALT1(1-824)-His) purified from baculovirus-infected insect cells. The tetrapeptide LRSR is coupled to AMC (7-amino-4-methylcoumarin) and provides a quenched, fluorescent substrate for the MALT1 protease (SM Biochemicals). Cleavage of AMC from the Arginine residue results in an increase in coumarin fluorescence measured at 460 nm (excitation 355 nm). The final assay buffer consisted of 10 nM FL MALT1 protein, 200 μM Ac-LRSR-AMC, 50 mM Tris pH 7.5, 0.6 M Citrate, 1 mM DTT, 1 mM EDTA, 0.05% BSA and 1.5% DMSO. Test compounds were spotted at 50 nL in 100% DMSO per well of a black 384-Proxiplate (Perkin Elmer). Test compound concentrations ranged from 30 μM to 0.5 nM using 11 dilution steps (1:3). Background signal was measured from control wells containing assay buffer without enzyme which functions as low control (LC). High control (HC) values were generated using the reaction with enzyme but no compound treatment. Compounds were pre-incubated with MALT1 enzyme for 50 minutes at RT. Substrate was added subsequently and fluorescence was measured in Labsystems fluoroskan at excitation 355 nm and emission 460 nm to determine time 0. The reaction was subsequently incubated for 4 h at RT and fluorescence was measured. For IC₅₀ calculations, timepoint 0 was subtracted from the 4 h timepoint to correct for any potential autofluorescence of the compounds. The enzyme reaction was linear during the 4 h incubation period. Characterization of the substrate Ac-LRSR-AMC determined the Michaelis constant KM at 200 μM.

IC$_{50}$ values were calculated using the following formula (Z prime should be >0.5):

LC  = Median of the low control values
    = Low control: Reaction without enzyme
HC  = Median of the high control values
    = High control: Reaction without enzyme % Effect    = 100 − [(sample-LC)/(HC-LC) × 100]
% Control   = (sample/HC) × 100
% Controlmin = (sample-LC)/(HC-LC) × 100

A best-fit curve was fitted by a minimum sum of squares method to the plot of % Controlmin vs. compound concentration. From this an IC$_{50}$ value (inhibitory concentration causing 50% inhibition) can be obtained. An estimate of the slope of the plot in terms of the Hill coefficient was also obtained.

IC$_{50}$ Calculation:

$$y = LB + \frac{UB - LB}{1 + 10^{(h(pConc - pIC50))}}$$

With
y=estimated response
UB=upper bound
LB=lower bound
h=hill

Used in "Lexis Dose Response Curve Fitting" Version 1.0. Resultant data are shown in Table 2.

TABLE 2

| Cpd No. | MALT1_Biochemical activity (Ac-LRSR-amc) IC50 (μM) |
|---|---|
| 1 | 0.049 |
| 2 | 0.038 |
| 3 | 0.251 |
| 4 | 0.050 |
| 5 | 0.372 |
| 6 | 0.030 |
| 7 | 0.120 |
| 8 | 0.457 |
| 9 | 0.081 |
| 10 | 0.026 |
| 11 | 0.089 |
| 12 | 0.219 |
| 13 | 0.019 |
| 14 | 0.209 |
| 15 | 0.033 |
| 16 | 0.025 |
| 17 | 2.344 |
| 18 | 2.188 |
| 19 | 2.818 |
| 20 | 0.355 |
| 21 | 0.087 |
| 22 | 0.977 |
| 23 | 0.036 |
| 24 | 0.251 |
| 25 | 0.457 |
| 26 | 0.562 |
| 27 | 1.023 |
| 28 | 1.318 |
| 29 | 6.0 |
| 30 | 0.83 |
| 31 | 3.16 |

TABLE 2-continued

| Cpd No. | MALT1_Biochemical activity (Ac-LRSR-amc) IC50 (μM) |
|---|---|
| 32 | 8.13 |
| 33 | 0.98 |

Biological Example 2

PMA Induced IL2 Production in Jurkat Cells

Jurkat cells were maintained in complete RPMI 1640 media containing 10% fetal bovine serum, 10 mM HEPES, 100 units/mL of penicillin and 100 μg/mL of streptomycin. Prior to the assay, compounds were made 2- to 4-fold serial dilutions in DMSO. A volume of 10 μL of DMSO-diluted compound in each well were further diluted into 240 RPMI1640 complete media. Jurkat cells were harvested by centrifuge at 1200 RPM for 5 min, washed one time with RPMI 1640 media, and suspended in fresh complete RPMI 1640 media at concentration of $1.25 \times 10^6$ cell/mL. A volume of 160 μL of Jurkat cells ($2 \times 10^5$ cells) were seeded in each well of 96 well plate-bottom plates. A volume of 20 μL of diluted compound in RMPI 1640 complete media were added to each well and incubated with Jurkat cells for 30 min at 37° C. in a 5% $CO_2$ incubator. A volume 20 μL of diluted PMA/Ionomycin (81 nM/1.3 uM respectively, ebioscience, catalog number 00-4970-93) in RMPI 1640 complete media were added to each well. After incubation at 37° C. in 5% $CO_2$ incubator for 20 h, supernatants were harvested. IL-2 concentration were assessed by ELISA (IL2 Duoset, R&D Systems, catalog number DY202). Colorimetric intensity at 450 nm was read by Spectramax plate reader and analyzed with Softmax Pro software. Cell viability was assessed by Cell Titer Glo kit (Promega, catalog number G7571) using Victor Luminescence reader (Victor 3V 4202938 by Perkin Elmer). Resultant data are shown in Table 3.

Biological Example 3

Human IL6/1L10 Mesoscale Assay

NF$_κ$B signaling regulates the secretion of multiple cytokines, including IL6 and IL10. Secretion of the cytokines IL6 and IL10 by TMD8 ABC-DLBCL cells was measured using a mesoscale assay. Inhibition of NF$_κ$B signaling by MALT1 or BTK inhibitors results in a decrease of IL6/10 secretion.

TMD8 cells were propagated in RPMI-1640 (Sigma Aldrich) supplemented with 10% fetal bovine serum (HyClone), 1 mM sodium pyruvate (Invitrogen), 2 mM L-glutamine (Sigma Aldrich) and 1% PenStrep (Sigma Aldrich). Cell passage number should not exceed 30. Cells should be kept between 0.5-2.5 million cells per mL during culturing and cells should be supplemented every 2-3 days with fresh 50 μM beta-mercaptoenthanol. No beta-mercaptoethanol was used during the mesoscale assay.

For the Mesoscale assay, 100,000 TMD8 cells were seeded per well into black-colored 96-well plates with clear bottom (Corning #3904) and test compounds were added in 9 dilution steps (1:2) ranging from 15 μM to 58.6 nM (final DMSO concentration 0.3%). DMSO control wells were used to determine the maximum signal (High Control (HC)). Treatment with the BTK inhibitor RN486 in a dose range from 30 nM to 131 pM (9 dilutions of 1:2) served as a positive control for NF$_K$B pathway inhibition and was used to determine the maximum inhibition (Low Control (LC)). Compounds and cells were incubated for 24 h at 37° C. and 5% CO$_2$ (assay volume is 150 μL). After 24 h of incubation 50 μL of the supernatant was transferred to a MSD plate (V-Plex Proinflammation Panel 1 (human) kit, Mesoscale (MSD)) and incubated for 2 h with vigorous shaking (600 rpm) at room temperature. Following incubation, plates were washed 3× with PBS+0.05% Tween-20 and 25 μL detection antibody solution (IL6 & IL10 antibodies in diluent 3 (MSD)) was added per well followed by 2 h of incubation with vigorous shaking (600 rpm) at room temperature. After 3× washes with PBS+0.05% Tween-20, plates were incubated with 150 μL 2× Read Buffer T and read on SECTOR imager.

IC$_{50}$ values were calculated using the following formula (Z prime should be >0.5):

$$
\begin{aligned}
LC(BTK\ inhibitor) &= \text{median of the low control values} \\
&= \text{Low control: Reaction with 100 nM} \\
&\quad \text{final concentration} \\
HC &= \text{mean of the High Control values} \\
&= \text{High control: Reaction without DMSO, no compound} \\
&\quad (DMSO\ 0.3\%\ \text{final}) \\
\%\ Effect &= 100 - (sample\text{-}LC)/(HC\text{-}LC) \times 100 \\
\%\ Control &= (sample/HC) \times 100 \\
\%\ Controlmin &= (sample\text{-}LC)/(HC\text{-}LC) \times 100
\end{aligned}
$$

A best-fit curve was fitted by a minimum sum of squares method to the plot of % Control vs. compound concentration. From this an IC$_{50}$ value (inhibitory concentration causing 50% signal decrease) can be obtained. An estimate of the slope of the plot in terms of the Hill coefficient was also obtained.

IC$_{50}$ values were calculated using the following formula (Z prime should be >0.5):

$$
\begin{aligned}
LC(ATP\text{-}GLO) &= \text{median of the low control values} \\
&= \text{Low control: Reaction without cells, only medium} \\
HC(ATP\text{-}GLO) &= \text{Median of the high control values} \\
&= \text{High control: Reaction with cells without compound, with DMSO} \\
\%\ Effect &= 100 - (sample\text{-}LC)/(HC\text{-}LC) \times 100 \\
\%\ Control &= (sample/HC) \times 100 \\
\%\ Controlmin &= (sample\text{-}LC)/(HC\text{-}LC) \times 100
\end{aligned}
$$

A best-fit curve was fitted by a minimum sum of squares method to the plot of % Control vs. compound concentration. From this an IC$_{50}$ value (inhibitory concentration causing 50% cytotoxicity) can be obtained. An estimate of the slope of the plot in terms of the Hill coefficient was also obtained. Resultant data are shown in Table 3.

TABLE 3

| Cpd No. | Human IL6 Mesoscale assay (TMD-8) IC50 (μM) | Human IL10 Mesoscale assay (TMD-8) IC50 (μM) | Human IL6 Mesoscale assay (OCI-LY3) IC50 (μM) | Human IL10 Mesoscale assay (OCI-LY3) IC50 (μM) | IL-2 prod h Jurkat PMA IC50 (μM) |
|---|---|---|---|---|---|
| 1 | | | 0.091 | 0.087 | |
| 2 | | | 0.083 | 0.047 | |
| 3 | | | 0.151 | 0.114 | |
| 4 | | | 0.047 | 0.031 | |
| 5 | | | 0.281 | 0.371 | |
| 6 | | | 0.257 | 0.105 | |
| 7 | | | 0.219 | 0.065 | |
| 9 | | | 0.240 | 0.129 | |
| 10 | | | 0.123 | 0.023 | |
| 11 | | | 0.138 | 0.065 | |
| 12 | | | 0.288 | 0.155 | |
| 13 | | | 0.022 | 0.019 | |
| 14 | | | 0.115 | 0.501 | |
| 15 | | | 0.047 | 0.031 | |
| 16 | | | 0.042 | 0.041 | |
| 21 | | | 0.245 | 0.200 | |
| 23 | | | 0.200 | 0.115 | |

Biological Example 4

Proliferation Assays

To assess anti-proliferative effects, MALT1 inhibitor test compounds may be tested in 4-day proliferation assays using three different DLBCL cell lines. Two ABC-DLBCL cell lines with activating mutations in the classical NF$_K$B pathway may be evaluated (OCI-Ly3 (CARD11, MYD88 & A20 mutations), TMD8 (CD79B & MYD88 mutations), which are generally sensitive to NF$_K$B pathway inhibition. A GCB-DLBCL cell line (OCI-Ly7), which has not been shown to have active NF$_K$B signaling, may serve as a negative control to exclude compounds with general cytotoxic effects.

OCI-Ly3 cells may be propagated in RPMI-1640 (Sigma Aldrich) supplemented with 10% fetal bovine serum (HyClone), 2 mM L-glutamine (Sigma Aldrich) and 1% PenStrep (Sigma Aldrich). TMD8 cells may be propagated in RPMI-1640 (Sigma Aldrich) supplemented with 10% fetal bovine serum (HyClone), 1 mM sodium pyruvate (Invitrogen), 2 mM L-glutamine (Sigma Aldrich) and 1% PenStrep (Sigma Aldrich). Cells should be kept between 0.5-2.5 million cells per mL during culturing and cells should be supplemented every 2-3 days with fresh 50 μM beta-mercaptoenthanol. No beta-mercaptoethanol is used during the proliferation assay. OCI-Ly7 cells may be propagated in IMDM (ThermoFisher) supplemented with 10% fetal bovine serum (HyClone), 2 mM L-glutamine (Sigma Aldrich) and 50 μg/mL Gentamycin. Cell passage numbers should not exceed 30.

To assess anti-proliferative effects, 400 nL of test compounds may be spotted per well of 96-well plates (Costar, catalogue number 3904). 10,000 TMD8, 10,000 OCI-Ly3 or 2,000 OCI-Ly7 cells may be seeded in 100 μL media per well and incubated for 4 days at 37° C. and 5% CO$_2$. Cell plating numbers may be chosen based on growth curves to ensure linear cell growth. After 4 days of incubation 50 μL CellTiterGLO reagent (Promega) may be added to each well and luminescence may be measured on the Envision after 10 min of incubation at room temperature.

IC$_{50}$ values may be calculated using the following formula (Z prime should be >0.5):

LC = median of the low control values
= Low control: Reaction without cells
HC = Median of the high control values
= High control: Reaction with cells without compound % Effect = 100 − (sample−LC)/(HC−LC) × 100
% Control = (sample/HC) × 100
% Controlmin = (sample−LC)/(HC−LC) × 100

A best-fit curve may be fitted by a minimum sum of squares method to the plot of % Control vs. compound concentration. From this an IC50 value (inhibitory concentration causing 50% cytotoxicity) can be obtained. An estimate of the slope of the plot in terms of the Hill coefficient can also be obtained.

Biological Example 5

Tumor Efficacy Studies

The OCI-Ly3 (DSMZ, catalog number ACC 761) human diffuse large B-cell lymphoma tumor cells may be maintained in vitro in RPMI medium supplemented with heat inactivated fetal bovine serum (10% v/v) and 2 mM L-Glutamine 200 mM at 37° C. in an atmosphere of 5% $CO_2$ in air. The cells may be routinely subcultured once weekly. The cells growing in an exponential growth phase may be harvested and counted, and cell suspension diluted 1:1 in Matrigel™ (Corning Matrigel™ Matrix Basement Membrane Growth Factor Reduced) for tumor cell inoculation.

Male NSG (NOD.Cg-Prkdc$^{scid}$ Il2 rg$^{tm1Wjl}$/SzJ) mice may be subcutaneously inoculated with OCI-Ly3 cells ($10 \times 10^6$ cells in 1:1 medium:Matrigel™ in a volume of 200 μL) in the inguinal region of each animal. The day of tumor cell inoculation may be denoted as day 0. Tumor measurements may be monitored twice weekly beginning seven days post-implantation, until the mean tumor volume is 169±42 mm$^3$, at which point mice may be randomized by tumor volume into treatment groups. Compound or vehicle may be orally administered according to body weight (5 mL/kg) once or twice daily until study termination. Tumor measurements and body weights may be recorded twice weekly.

The endpoints of the studies are tumor growth inhibition, maximal tumor burden (individual tumor size equaling 10% of body weight), and body weight loss greater than 20% treatment initiation body weight. Percent body weight change may be calculated using the formula: Body weight change=[(C−I)/I]*100 where C is the current body weight and I is the body weight at the initiation of treatment. Tumor size may be measured twice weekly in two dimensions using a caliper and the volume may be expressed in mm$^3$ using the formula: $V=0.5 \times a \times b^2$ where and b are the long and short diameters of the tumor, respectively. Complete tumor regression (CR) is defined as tumors that are reduced to below the limit of palpation (20 mm$^3$). Partial tumor regression (PR) is defined as tumors that are reduced by at least half from initial tumor volume. A minimum duration of CR or PR in three or more successive tumor measurements is required for a CR or PR to be considered durable.

Summary statistics, including mean and the standard error of the mean (SEM), are provided for the tumor volume of difference in tumor volume among each group at each time-point are shown in corresponding study tables. Statistical analysis of difference in tumor volume among the groups may be evaluated using a two-way ANOVA repeated measures test, followed by Tukey post-test, using GraphPad Prism version 6.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound independently selected from the group consisting of:
   5-(4-((5-chloro-6-(2H-1,2,3-triazol-2-yl)pyridin-3-yl)carbamoyl)-5-(trifluoromethyl)-1H-pyrazol-1-yl)imidazo[1,2-a]pyridine-8-carboxamide;
   N-(5-chloro-6-(2H-1,2,3-triazol-2-yl)pyridin-3-yl)-1-(8-cyanoimidazo[1,2-a]pyridin-5-yl)-5-(trifluoromethyl)-1H-pyrazole-4-carboxamide;
   N-(5-chloro-6-(1H-pyrazol-1-yl)pyridin-3-yl)-1-(8-fluoroimidazo[1,2-a]pyridin-5-yl)-5-(trifluoromethyl)-1H-pyrazole-4-carboxamide;
   N-(6-(2H-1,2,3-triazol-2-yl)-5-(trifluoromethyl)pyridin-3-yl)-1-(8-fluoroimidazo[1,2-a]pyridin-5-yl)-5-(trifluoromethyl)-1H-pyrazole-4-carboxamide;
   1-(8-fluoroimidazo[1,2-a]pyridin-5-yl)-N-(6-(methylsulfonyl)-5-(trifluoromethyl)pyridin-3-yl)-5-(trifluoromethyl)-1H-pyrazole-4-carboxamide;
   N-(5-chloro-6-(oxazol-2-yl)pyridin-3-yl)-1-(8-fluoroimidazo[1,2-a]pyridin-5-yl)-5-(trifluoromethyl)-1H-pyrazole-4-carboxamide;
   N-(5-chloro-6-(2H-1,2,3-triazol-2-yl)pyridin-3-yl)-1-(8-methylimidazo[1,2-a]pyridin-5-yl)-5-(trifluoromethyl)-1H-pyrazole-4-carboxamide;
   N-(5-chloro-6-(2H-1,2,3-triazol-2-yl)pyridin-3-yl)-1-(8-fluoroimidazo[1,2-a]pyridin-5-yl)-5-(methylsulfonyl)-1H-pyrazole-4-carboxamide;
   N-(5-chloro-6-(5-methyloxazol-2-yl)pyridin-3-yl)-1-(8-fluoroimidazo[1,2-a]pyridin-5-yl)-5-(trifluoromethyl)-1H-pyrazole-4-carboxamide;
   N-(5-chloro-6-(4-methyloxazol-2-yl)pyridin-3-yl)-1-(8-fluoroimidazo[1,2-a]pyridin-5-yl)-5-(trifluoromethyl)-1H-pyrazole-4-carboxamide;
   1-(7-cyanopyrazolo[1,5-a]pyridin-4-yl)-5-(trifluoromethyl)-N-(2-(trifluoromethyl)pyridin-4-yl)-1H-pyrazole-4-carboxamide;
   4-(5-(trifluoromethyl)-4-((2-(trifluoromethyl)pyridin-4-yl)carbamoyl)-1H-pyrazol-1-yl)pyrazolo[1,5-a]pyridine-7-carboxamide;
   N-(5-chloro-6-(2H-1,2,3-triazol-2-yl)pyridin-3-yl)-1-(7-cyanopyrazolo[1,5-a]pyridin-4-yl)-5-(trifluoromethyl)-1H-pyrazole-4-carboxamide;
   1-(7-chloropyrazolo[1,5-a]pyridin-4-yl)-5-(trifluoromethyl)-N-(2-(trifluoromethyl)pyridin-4-yl)-1H-pyrazole-4-carboxamide;
   N-(5-chloro-6-(2H-1,2,3-triazol-2-yl)pyridin-3-yl)-1-(7-chloropyrazolo[1,5-a]pyridin-4-yl)-5-(trifluoromethyl)-1H-pyrazole-4-carboxamide
   4-(4-((5-chloro-6-(2H-1,2,3-triazol-2-yl)pyridin-3-yl)carbamoyl)-5-(trifluoromethyl)-1H-pyrazol-1-yl)pyrazolo[1,5-a]pyridine-7-carboxamide;
   (*S)—N-(5-chloro-6-(1-methoxyethyl)pyridin-3-yl)-1-(8-fluoroimidazo[1,2-a]pyridin-5-yl)-5-(trifluoromethyl)-1H-pyrazole-4-carboxamide;
   (*R)—N-(5-chloro-6-(tetrahydrofuran-2-yl)pyridin-3-yl)-1-(8-chloroimidazo[1,2-a]pyridin-5-yl)-5-(trifluoromethyl)-1H-pyrazole-4-carboxamide;

(*R)—N-(5-chloro-6-(1-methoxyethyl)pyridin-3-yl)-1-(8-fluoroimidazo[1,2-a]pyridin-5-yl)-5-(trifluoromethyl)-1H-pyrazole-4-carboxamide;

(*S)—N-(5-chloro-6-(tetrahydrofuran-2-yl)pyridin-3-yl)-1-(8-chloroimidazo[1,2-a]pyridin-5-yl)-5-(trifluoromethyl)-1H-pyrazole-4-carboxamide;

(*S)—N-(5-chloro-6-(tetrahydrofuran-2-yl)pyridin-3-yl)-1-(7-chloropyrazolo[1,5-a]pyridin-4-yl)-5-(trifluoromethyl)-1H-pyrazole-4-carboxamide;

(*R)—N-(5-chloro-6-(tetrahydrofuran-2-yl)pyridin-3-yl)-1-(7-chloropyrazolo[1,5-a]pyridin-4-yl)-5-(trifluoromethyl)-1H-pyrazole-4-carboxamide;

(*S)—N-(5-chloro-6-(tetrahydrofuran-2-yl)pyridin-3-yl)-1-(7-cyanopyrazolo[1,5-a]pyridin-4-yl)-5-(trifluoromethyl)-1H-pyrazole-4-carboxamide;

(*R)—N-(5-chloro-6-(tetrahydrofuran-2-yl)pyridin-3-yl)-1-(7-cyanopyrazolo[1,5-a]pyridin-4-yl)-5-(trifluoromethyl)-1H-pyrazole-4-carboxamide;

(*S)—N-(5-chloro-6-(1-methoxyethyl)pyridin-3-yl)-1-(7-cyanopyrazolo[1,5-a]pyridin-4-yl)-5-(trifluoromethyl)-1H-pyrazole-4-carboxamide;

(*R)—N-(5-chloro-6-(1-methoxyethyl)pyridin-3-yl)-1-(7-cyanopyrazolo[1,5-a]pyridin-4-yl)-5-(trifluoromethyl)-1H-pyrazole-4-carboxamide;

(*S)—N-(5-chloro-6-(1-methoxyethyl)pyridin-3-yl)-1-(7-chloropyrazolo[1,5-a]pyridin-4-yl)-5-(trifluoromethyl)-1H-pyrazole-4-carboxamide;

(*R)—N-(5-chloro-6-(1-methoxyethyl)pyridin-3-yl)-1-(7-chloropyrazolo[1,5-a]pyridin-4-yl)-5-(trifluoromethyl)-1H-pyrazole-4-carboxamide;

N-(6-((dimethyl(oxo)-$\lambda^6$-sulfanylidene)amino)-5-methylpyridin-3-yl)-1-(8-fluoroimidazo[1,2-a]pyridin-5-yl)-5-(trifluoromethyl)-1H-pyrazole-4-carboxamide;

N-(6-((dimethyl(oxo)-$\lambda^6$-sulfanylidene)amino)-5-(trifluoromethyl)pyridin-3-yl)-1-(8-fluoroimidazo[1,2-a]pyridin-5-yl)-5-(trifluoromethyl)-1H-pyrazole-4-carboxamide;

1-(8-fluoroimidazo[1,2-a]pyridin-5-yl)-N-(6-(S-methylsulfonimidoyl)-5-(trifluoromethyl)pyridin-3-yl)-5-(trifluoromethyl)-1H-pyrazole-4-carboxamide;

N-(6-((dimethyl(oxo)-$\lambda^6$-sulfanylidene)amino)-5-fluoropyridin-3-yl)-1-(8-fluoroimidazo[1,2-a]pyridin-5-yl)-5-(trifluoromethyl)-1H-pyrazole-4-carboxamide; and N-(5-chloro-6-((dimethyl(oxo)-$\lambda^6$-sulfanylidene)amino)pyridin-3-yl)-1-(8-fluoroimidazo[1,2-a]pyridin-5-yl)-5-(trifluoromethyl)-1H-pyrazole-4-carboxamide or an enantiomer, diastereomer, or a pharmaceutically acceptable salt form thereof.

2. A pharmaceutical composition comprising a compound of claim 1 and at least one of a pharmaceutically acceptable carrier, a pharmaceutically acceptable excipient, and a pharmaceutically acceptable diluent.

3. The pharmaceutical composition of claim 2, wherein the composition is a solid oral dosage form.

4. The pharmaceutical composition of claim 2, wherein the composition is a syrup, an elixir or a suspension.

5. A method of treating a disease, syndrome, condition, or disorder, wherein said disease, syndrome, condition, or disorder is affected by the inhibition of MALT1, comprising administering to a subject in need thereof a therapeutically effective amount of the compound of claim 1.

6. The method of claim 5 wherein said disease, syndrome, condition, or disorder is selected from the group consisting of diffuse large B-cell lymphoma (DLBCL), mantle cell lymphoma (MCL), follicular lymphoma (FL), and mucosa-associated lymphoid tissue (MALT) lymphoma rheumatoid arthritis (RA), psoritic arthritis (PsA), psorisis (Pso), ulcerative colitis (UC), Crohn's disease, systemic lupus erythematosus (SLE), asthma, and chronic obstructive pulmonary disease (COPD).

7. A method of treating a disease, syndrome, condition, or disorder, wherein said disease, syndrome, condition, or disorder is affected by the inhibition of MALT1, comprising administering to a subject in need thereof a therapeutically effective amount of (a) a MALT1 inhibitor, and (b) a pharmaceutical agent selected from the group consisting of a BTK inhibitor, a SYK inhibitor, a PKC inhibitor, a PI3K pathway inhibitor, a BCL family inhibitor, a JAK inhibitor, a PIM kinase inhibitor, a B cell antigen-binding antibody, an immune cell redirection agent, an immunomodulatory agent, an anti-PD1 antibody, and an anti-PD-L1 antibody;

wherein said MALT1 inhibitor is a compound of claim 1 or an enantiomer, diastereomer, or pharmaceutically acceptable salt form thereof.

8. The method of claim 7 wherein the BTK inhibitor is ibrutinib.

9. The method of claim 7 wherein the B cell antigen-binding antibody is rituximab.

10. The method of claim 7 wherein the immunomodulatory agent is daratumumab.

* * * * *